United States Patent [19]

Midoux et al.

[11] Patent Number: 5,733,762
[45] Date of Patent: Mar. 31, 1998

[54] COMPLEXES OF NUCLEIC ACID AND POLYMER, THEIR PROCESS OF PREPARATION AND THEIR USE FOR THE TRANSFECTION OF CELLS

[75] Inventors: Patrick Midoux; Patrick Erbacher, both of Orleans; Annie-Claude Roche-Degremont, Sandillon; Michel Monsigny, Saint-Cyr-En-Val, all of France

[73] Assignee: I.D.M. Immuno-Designed Molecules, France

[21] Appl. No.: 741,678

[22] Filed: Oct. 31, 1996

Related U.S. Application Data

[63] Continuation-in-part of Ser. No. 505,068, Jul. 21, 1995, abandoned, which is a continuation-in-part of Ser. No. 288,681, Aug. 10, 1994, Pat. No. 5,595,897.

[30] Foreign Application Priority Data

Apr. 28, 1994 [FR] France ................. 94 05174

[51] Int. Cl.$^6$ ............... C07K 1/00; C07K 1/107; C12N 15/00; C12N 15/88
[52] U.S. Cl. ............ 435/172.3; 435/325; 514/44; 530/300; 530/345; 530/350; 530/395; 530/402; 536/23.2; 536/23.5; 536/24.5; 536/23.7
[58] Field of Search ................. 435/6, 69.1, 91.1, 435/172.3, 172.1, 240.2, 183, 189, 193, 194, 207, 325, 375, 91.3, 91.31, 320.1; 530/345, 395, 402, 300, 350; 536/23.1, 23.2, 23.5, 23.7, 23.72, 23.74, 24.5; 514/44

[56] References Cited

U.S. PATENT DOCUMENTS 5,595,897  1/1997  Midoux et al. ............ 435/172.3

OTHER PUBLICATIONS

Crystal. "Transfer of Genes to Humans: Early Lessons and Obstacles to Success" Science 270: 404–410, Oct. 1995.

Gura. "Antisense has Growing Pains" Science 270: 575–677, Oct. 1995.

Stull et al. Antigene, Ribozyme, and Aptamer Nucleic Acid Drugs: Prospect and Progress Pharm. Rev. 12: 465–483, Apr. 1995.

*Primary Examiner*—George C. Elliott
*Assistant Examiner*—Thomas G. Larson
*Attorney, Agent, or Firm*—Bierman, Muserlian and Lucas

[57] ABSTRACT

A compound consisting essentially of polylysine conjugated to non-charged residues and recognition signals wherein the free amino functions of said polylysine are substituted with non-charged residues and said recognition signals, which non-charged residues consist of gluconalactone and which recognition signals are at least one member of the group consisting of galactoside, mannoside, fucoside, Lewis$^x$, Lewis$^b$, oligomannoside, oligolactosamine saccharides and peptide ANP and said conjugated polylysine contains at least 30% unsubstituted free amino functions and a method of transfecting cultured cells.

15 Claims, 28 Drawing Sheets

$R = NH_3^+$ or $R = NH - CO - (CHOH)_m - R_1$

000# COMPLEXES OF NUCLEIC ACID AND POLYMER, THEIR PROCESS OF PREPARATION AND THEIR USE FOR THE TRANSFECTION OF CELLS

This application is a Continuation-in-Part of U.S. patent application Ser. No. 505,068, filed Jul. 21, 1995, now abandoned, which is a Continuation-in-Part of U.S. patent application Ser. No. 288,681 filed Aug. 10, 1994, now U.S. Pat. No. 5,595,897, issued Jan. 21, 1997.

STATE OF THE ART

The introduction of a foreign gene in a cell is of great interest for gene therapy. While in in vitro experiments, general methods using calcium phosphate precipitation, DEAE dextran, or cationic lipids are suitable, more selective methods are required to specifically transfer a gene into a given cell population with the aim of developing gene therapy. Amongst these selective methods, gene transfer may be achieved by making use either of modified virus material starting with vaccinia virus or retrovirus, or of targeted liposomes, or of targeted macromolecule gene complexes. DNA/carrier complexes such as polylysine substituted with asialoorosomucoide, insulin or transferrin have been proposed as targeted carriers of plasmid allowing cell transfection upon an endocytotic process induced by the corresponding receptors: the galactose specific receptor (lectin) with the asialoorosomucoide, the insulin receptor and the transferrin receptor.

It has been established that numerous animal cells possess membrane lectins (Monsigny M., Roche A. C., Kieda C., Midoux P., Obrenovitch A. Characterization and biological implications of membrane lectins in tumor, lymphoid and myeloid cells. Biochemie, 1988: 70: 1633–49; Varki A. Selectin and other mammalian sialic acid binding lectins. Curr. Op. in Cell. Biol., 1992, 4: 257–66] which specifically recognize the osides of various structures. In particular, the membrane lectin of cells of the hepatic parenchyma cells recognize oligosaccharides with a galactose residue in terminal non-reducing position, which means that all galactose has alcohol functions free, as is the case of asiologlycoproteins [Ashwell G., Harford J. Carbohydrate-specific receptors of the liver. Ann. Rev. Biochem., 1982, 51: 531–54].

The specificity of these lectins depends on the cell type, and therefore membrane lectins are good candidates for gene transfer by glycoconjugate/DNA complexes as specific carriers. Soluble glycoconjugates bearing defined sugar moieties have been used to efficiently target drugs, including cytotoxic drugs, toxins, immunomodulators, antiviral drugs [see, Monsigny M., Roche A. C., Kieda C., Midoux P. and Obrenovitch A. Biochemie, 1988: 70 1633–49 2; Roche A. C., Midoux P., Pimpaneau V., Nègre E., Mayer R. and Monsigny M. Res. Virol., 1990: 141 243–249] and oligonucleotides [Bonfins E., Depierreux C., Midoux P., Thuong N. T., Monsigny M., Roche A. C. Drug targeting: synthesis and endocytosis of oligonucleotide-neoglycoprotein conjugates. Nucleic Acids Res., 1992, 20: 4621–9; Bonfils E. Mèndes C., Roche A. C., Monsigny M., Midoux P. Uptake by macrophages of a biotinylated oligo-a-deoxythymidylate by using mannosylated streptavidin. Bioconjugate Chem., 1992, 3: 277–84].

Plasmid associated macromolecules capable of being specifically recognized by plasma membrane components of cell targets enter cells by a process mimicking the mechanism of entry of viral genetic material into cells. In every case described up to now, the macromolecular plasmid-carrier complex is specifically recognized by a membrane receptor which pulls the complex into intracellular vesicle endosomes by endocytosis, and probably into other deeper intracellular compartments, far from the plasma membrane. Moreover, the transmembrane passage of plasmid DNA is a critical process for its delivery into the cytosol and/or the nucleus, where the gene will be expressed.

OBJECTS OF THE INVENTION

It is an object of the invention to provide a compound consisting essentially of polylysine conjugated with non-charged residues in which at least 30% of the free amino functions ar unsubstituted.

It is another object of the invention to provide a novel method of transfecting cultured cells using the novel compounds in combination with a nucleic acid.

These and other objects and advantages of the invention will become obvious from the following detailed description.

THE INVENTION

The invention is of new stable complexes of nucleic acid and of substituted polymer.

The invention also is of new complexes of nucleic acid and substituted polymers which are able, upon dissociation, to release nucleic acid, in order to allow an effective expression of transfected nucleic acid into the cells.

The invention is of new nucleic acid complexes and substituted polymer which do not contain any recognition signals and which are able to transfect several types of cells.

The invention is of new nucleic acid complexes and substituted polymer which contain recognition signals recognized by membrane receptors, making the transfection selective for different types of cells.

The invention is of a method of specific cell transfection in vitro or in vivo.

The invention also is of new conjugates of polylysine capable of being linked to a nucleic acid in preparation for the selective transfection of a cell.

The invention also includes a compound consisting essentially of polylysine conjugated to non-charged residues wherein the free amino functions of said polylysine are substituted with said non-charged residues, which non-charged residues are at least one member of the group consisting of gluconolactone, galactoside, mannoside, fucoside, Lewis$^x$, Lewis$^b$, oligomannoside, oligolactosamine saccharides and peptide ANP and said conjugated polylysine contains at least 30% unsubstituted free amino functions.

The invention is also of new pharmaceutical compositions containing, as an active component, a complex of DNA and substituted polymers, particularly of substituted polylysine.

The invention is also of new complexes of nucleic acid and of substituted polymer possessing a high solubility in physiologic serum and divers culture mediums, capable of being administered in vivo at very high dosage levels.

The invention, in one of its most general definitions, concerns a complex between at least one negatively charged nucleic acid and at least one positively charged polymeric conjugate, the association between the nucleic acid and the polymeric conjugate being electrostatic in nature, the polymeric conjugate containing monomeric components harboring $NH_3^+$ free functions of the above-mentioned components, and being as follows:

the free $NH_3^+$ functions of the aforementioned components are substituted in a ratio of at least 10%, advantageously from 45% to 70%, particularly by 60%, this ratio being determined by a colorimetric method (Fields R. (1971). The measurement of amino groups on proteins and peptides. Biochem. J., 124: 581–590) or advantageously from 35% to 70%, particularly by 40%, this ratio being determined by nuclear magnetic resonance (NMR), by non-charged residues leading to a reduction of the number of positive charges in comparison with the same non-substituted polymeric conjugate, facilitating the release of nucleic acid by the dissociation of the complex, the aforementioned residues possess in addition the following properties:
→they contain at least one hydroxyl group,
→they do not correspond to a recognition signal recognized by a cellular membrane receptor, the free $NH_3^+$ functions of the aforementioned components and/or the hydroxyl groups from the aforementioned residues are also able to be substituted by a molecule which constitutes a recognition signal recognized by a cellular membrane receptor, under the condition that the polymeric conjugate, after substitution by the aforementioned residues and by the aforementioned recognition signals, contains at least 30% free $NH_3^+$ functions.

The originality of the invention is based on the use of a substituted polymer by a sufficient quantity of residues, allowing, i) the formation of stable complexes with a nucleic acid, polynucleotides RNA or DNA, particularly DNA, by electrostatic interactions between the negative charges of the nucleic acid, particularly DNA, and the remaining positive charges of the partially substituted polymer with the aforementioned resides, and ii) the facilitation of the dissociation of the complex and the release of the nucleic acid in order to allow an efficient expression of the gene in the transfected cells.

Indeed, the aforementioned substituted polymer allows a condensation of the DNA which remains very strong as a result of a cooperative phenomenon between the positive charges of the polymer and the negative charges of the DNA. For example, the substituted polymer at 58% with an aforementioned residue possesses less positive charges, which thus reduces the interaction cooperativity and facilitates the dissociation between the DNA and the polymer.

The dissociation of the complex can be measured under the conditions described under FIG. 6.

Taken by itself, the polymeric conjugate contains monomers which harbor $NH_2$ free functions which are capable of becoming $NH_3^+$ under appropriate pH conditions (pH<10).

Furthermore, the presence of a cellular membrane recognition signal is not required.

The expression according to which "the residues substituting $NH_2$ do not correspond to any cellular membrane recognition signal" means that they do not correspond to any signal according to what is known today in the literature.

By recognition signal recognized by a cellular membrane receptor, we generally mean a molecule or a molecular complex able to selectively recognize a ligand (signal-receptor affinity$\geq 10^3$ l/mole).

The number of recognition signals which substitute the free $NH_3^+$ of the aforementioned components and/or the hydroxyl groups of the aforementioned residues varies from 0 to 40%.

Given that the number of free $NH_3^+$ on the polymeric conjugate must be at least 30%, while the $NH_3^+$ of the aforementioned components are substituted by 10% of non-charged residues, particularly gluconoyle, the number of recognition signals may be up to 40% of the 90% non-engaged $NH_3^+$ with non-charged residues and/or on the hydroxyl groups of the aforementioned residues. While 45% of the $NH_3^+$ of the aforementioned components are substituted by 45% with non-charged residues, the recognition signals are able to be on 25 of the 55% of $NH_3^+$ which are not substituted with the non-charged residues and/or on the hydroxyls of the aforementioned residues. On the other hand, while the number of $NH_3^+$ engaged in links with the residues increases up to 70%, with the result that the polymeric conjugate keeps at least 30% of free $NH_3^+$, the recognition signals are no longer able to exist except when they substitute the hydroxyls of the aforementioned residues.

The substitution level of free $NH_3^+$ functions of the aforementioned components by non-charged residues may be determined by 2 methods:

1) a colorimetric method after reaction of the 2,4,6 trinitobenzene sulfonic acid (TNBS) (Fields R. (1971). The measurement of amino groups on proteins and peptides. Biochem. J., 124: 581–590) with the ε-amino groups of free lysine residues of the gluconoylated polylysine. The average number of gluconoyle residues bound per polylysine molecule was obtained from the difference between the absorbance obtained with the non-substituted polylysine, and that obtained with the gluconoylated polymer;

2) a physical method using the nuclear magnetic resonance (NMR); the NMR spectrums are recorded at 300 MHz from 4 mg of gluconoylated polylysine in $D_2O$ and dissolved in 0.5 ml of $D_2$) (FIGS. 9 and 10);

the average number, x, of gluconoyle residues bound per molecule of polylysine is determined by the relation:

$$x = {}^3\!/_2 \cdot (h_{GlcA}/h_{Lys}) \cdot DP$$

where $h_{Lys}$ is the value of the integration around 1.7 ppm corresponding to 6 protons from carbons 3, 4 and 5 (FIG. 1) of a lysine residue of the polylysine, $h_{GlcA}$ is the value of the integration around 3.8 ppm corresponding to 4 protons of a gluconoyle group (FIGS. 9 and 10) and DP is the degree of polymerization of the polylysine;

the relation above has to be adapted according to the nature of the residue.

It should be noted that the number of non-charged residues on the polymeric conjugate depends on the method used. This number was overestimated when the colorimetric assay was used to calculate by difference the relative number of non-charged residue on the polymeric conjugate. In contrast, NMR allows to calculate directly the number of amino acid residues in the polymer.

Throughout this paper, unless otherwise stated, the substitution level of free $NH_3^+$ functions was determined by using the colorimetric assay.

The invention particularly concerns a complex between at least one negatively charged nucleic acid and at least one positively charged polymeric conjugate, the association between the nucleic acid and the polymeric conjugate being electrostatic in nature, the polymeric conjugate containing a polymer formed by monomeric components harboring free $NH_3^+$ functions of the aforementioned components, and being as follows:

the free $NH_3^+$ functions of the aforementioned components are substituted in a ratio of at least 10%, advantageously from 45% to 70%, particularly 60%, with non-charged residues leading to a reduction of positive charges in comparison with the same non-substituted polymeric conjugate, facilitating the release of the nucleic acid by dissociation from the complex;

the aforementioned residues possess, in addition, the following properties:
→they contain at least one hydroxyl group,
→they do not correspond to a recognition signal recognized by a cellular membrane receptor, the free $NH_3^+$ functions of the aforementioned components of the said residues are also able to be substituted with at least one molecule which constitutes a recognition signal recognized by a cellular membrane receptor, under the condition that the polymeric conjugate contains at least 30% free $NH_3^+$ functions.

The invention particularly concerns a complex between at least one negatively charged nucleic acid and at least one positively charged polymeric conjugate, the association between the nucleic acid and the polymeric conjugate being electrostatic in nature, the polymeric conjugate containing a polymer formed by monomeric components harboring free $NH_3^+$ functions of the aforementioned components and being as follows:

the free $NH_3^+$ functions of the aforementioned components are substituted in a ratio of at least 10%, more effectively from 45% to 70%, particularly 60%, by non-charged residues leading to a reduction of positive charges in comparison with the same non-substituted polymeric conjugate, facilitating the release of the nucleic acid by dissociation from the complex, the aforementioned residues possess, in addition, the following properties:
→they contain at least one hydroxyl group,
→they do not correspond to a recognition signal recognized by a cellular membrane receptor, the hydroxyl groups of the aforementioned residues are able to be substituted with at least one molecule which constitutes a recognition signal recognized by a cell membrane receptor, under the condition that the polymeric conjugate contains at least 30% free $NH_3^+$ functions.

In accordance with an advantageous embodiment, the invention concerns a complex between at least one negatively charged nucleic acid and at least one positively charged polymeric conjugate, the association between the nucleic acid and the polymeric conjugate being electrostatic in nature, the polymeric conjugate containing a polymer formed from monomeric components which possess free $NH_3^+$ functions, in particular residues of lysine, and being as follows:

the free $NH_3^+$ functions of the aforementioned components are substituted in a ratio of at least 10%, advantageously from 45% to 70%, particularly by approximately 60%, with non-charged residues leading to a reduction of positive charges in comparison with the same non-substituted polymeric conjugate, thus facilitating the dissociation of the complex and the release of the nucleic acid, the aforementioned residues possess, in addition, the following properties:
→they contain at least one hydroxyl group,
→they do not correspond to a cell recognition signal, 0 to 40% of the number of free $NH_3^+$ functions of the above-mentioned components being also substituted by a molecule which constitutes a recognition signal recognized by a cellular membrane receptor, this recognition signal having a molecular mass less than 5,000, under the condition that the polymeric conjugate contains at least 30% free $NH_3^+$ functions, and when it is present, this recognition signal can exist at the ratio of one molecule for approximately 10,000 components of the polymeric conjugate or approximately 60 molecules for approximately 10,000 components of the polymeric conjugate.

The invention concerns more particularly a complex between at least one negatively charged nucleic acid and at least one positively charged polymeric conjugate, the association between the nucleic acid and the polymeric conjugate being electrostatic in nature, the polymeric conjugate containing a polymer formed by monomeric components which have free $NH_3^+$ functions, in particular residues of lysine and being as follows:

the free $NH_3^+$ functions of the aforementioned components are substituted in a ratio of at least 10%, advantageously from 45% to 70%, particularly by approximately 60%, with non-charged residues leading to a reduction of positive charges in comparison with the same non-substituted polymeric conjugate, thus facilitating the dissociation of the complex and the release of the nucleic acid, the aforementioned residues possess, in addition, the following properties:
→they contain at least one hydroxyl group,
→they do not correspond to a cellular membrane recognition signal, the free $NH_3^+$ functions of the aforementioned components are able to be equally substituted by one molecule which constitutes a cellular recognition signal, this recognition signal being of molecular mass less than 5,000, and when it is present, this recognition signal can exist at the ratio of one molecule for approximately 10,000 components of the polymeric conjugate or approximately 60 molecules for approximately 10,000 components of the polymeric conjugate.

Under these conditions, taking into account the low number of recognition signals, at least 30% of the $NH_3^+$ of the polymeric conjugate are free.

When they are present, the purpose of the recognition signals is to render selective the transfection with regards to the nature of different types of cells and to make the transfection effective in vivo.

The recognition signals, taking into account the fact they generally are neutral, also have the effect of leading to a decrease of positive charges in the polymeric conjugate.

The recognition signals are molecules of low molecular mass (<5,000 daltons).

The number of recognition signal molecules fixed on the modified polymer can be, for a signal molecule with a very high affinity in relation to its receptor, from 0.5 to 5, advantageously 1 molecule for approximately 10,000 monomeric components of substituted polymer, thus being 1 molecule for approximately 50 molecules of substituted polymer;

for a signal molecule with medium affinity in relation to its receptor, approximately 10 to 100, advantageously 50 molecules for approximately 10,000 monomeric components of substituted polymer.

A signal molecule of very high affinity corresponds to a Ka value of at least $10^6$ l/mole.

A signal molecule of medium affinity corresponds to a Ka value of at least $10^4$ l/mole.

In accordance with an advantageous embodiment, in the complexes of the invention, the polymer contains a polymeric group of the following formula (I):

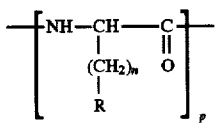

in which p is an integer varying from 2 to 500, preferably from 150 to 200, n is an integer varying from 1 to 5 and being preferably 4, this polymeric group contains a number of p of R residues among which:

10% to 70% of the number of R residues represents a NH—CO—(CHOH)$_m$—R$_1$ group, particularly a dihydroxylpropionoyle, erythrononoyle, threonoyle, ribonoyle, arabinoyle, xylonoyle, lyxonoyle, gluconoyle, galactonoyle, mannonoyle, glycoheptonoyle, glycooctonoyle residue, m is an integer from 2 to 15, preferably from 2 to 7, —R$_1$ represents H or an alkyl residue from 1 to 15 carbon atoms, particularly CH$_3$, the remaining residues, which are the 30% to 90% of the number of R residues, represent NH$_3^+$, R, moreover, having the ability to be constituted in 0 to 25% of the cases by a molecule which constitutes a recognition signal, under the condition that the polymeric conjugate contains at least 30% free NH$_3^+$ functions, and particularly at the ratio of 0.5 to 5, advantageously at 1 molecule for approximately 10,000 components, or at the ratio of 10 to 100, advantageously at 60 molecules for approximately 10,000 components.

In accordance with an advantageous embodiment, the invention concerns a complex as defined previously, in which the polymer includes a polymeric group of formula (II):

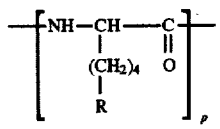

in which:

p has the meanings indicated above,

10% to 70% of the number of R residues represents a NH—CO—(CHOH)$_m$—R$_1$ group, m and R$_1$ having the meanings indicated above, the remaining residues, which are the 30% to 90% of the number of R residues, represent NH$_3^+$, and between 0 to 25% of the R residues are able to be substituted by a molecule which constitutes a recognition signal recognized by a cellular membrane receptor, under the condition that the polymeric conjugate contains at least 30% free NH$_3^+$ functions.

According to another embodiment, in the complexes of the invention, the polymer includes a polymeric group of formula (II):

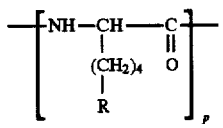

in which:

p has the meanings indicated above,

10% to 70% of the number of R residues represent a NH—CO—(CHOH)$_m$—R$_1$ having the meanings indicated above, the remaining residues, which are the 30% to 90% of the number of R residues, represent NH$_3^+$.

In this class of complexes of the invention, the polymer is a polylysine.

As demonstrated in the examples, HepG2 (human hepatocarcinoma) cells are efficiently transfected by the substituted polylysine containing 58±12% (110±22 residues) gluconoyle residues with an efficiency approximately 300 times higher than with the plasmid alone. The polylysines substituted by a few gluconoyle residues are not effective for obtaining a good transfection; those substituted by too many residues are slightly effective for obtaining a good transfection.

The polylysine substituted with 58±12% gluconoyle residues has the ability to transfect different cells adhering or in suspension (from humans, mice, rats, rabbits, monkeys, etc.) with a great efficacy, modulated according to the cell type and the promoter used.

According to another advantageous embodiment in the complexes of the invention, the polymer comprises a polymeric group of formula (II):

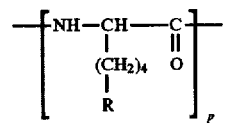

in which:

p has the meanings indicated above, this polymer contains a number p of R residues among which:

10% to 70% of the number of R residues represents a NH—CO—(CHOH)$_m$—R$_1$ group, m and R$_1$ having the meanings indicated above, the remaining residues, which are the 30% to 90% of R residues, represent in one part NH$_3^+$ and, in another part, represent a molecule which constitutes a recognition signal at the ratio of 0.5 to 5, advantageously at 1 molecule for 10,000 components.

According to another embodiment, in the complexes of the invention, the polymer comprises a polymeric group of formula (II):

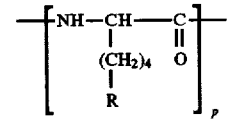

in which:

p has the meanings indicated above, this polymer contains a number p of R residues among which:

10% to 70% of the number of R residues represents a NH—CO—(CHOH)$_m$—R$_1$ group, m and R$_1$ having the meanings indicated above, the remaining residues, which are the 30% to 90% of the number of R residues, represent in one part $NH_3^+$ and, in another part, represent a molecule which constitutes a recognition signal at the ratio of 10 to 100, advantageously at 60 molecules for approximately 10,000 components.

In the complexes of the invention, the recognition signal could be chosen from the following:

A) from simple or complex osides recognized by membrane lectins, and chosen among the following items:

a. Asialo-oligoside of triantennary lactosamin type: asialoglycoprotein receptor

```
Galβ 4GlcNAcβ 2   Manα 6
Galβ 4GlcNAcβ 4        Manβ 4GlcNAcβ 2 4GlcNAcβ ──>
                Manα 3
Galβ 4GlcNAcβ 2
``` b. Asialo oligoside of tetraantennary lactosamin type: asialoglycoprotein receptor

```
Galβ 4GlcNAcβ 6
              Manα 6
Galβ 4GlcNAcβ 2
                    Manβ 4GlcNAcβ 4GlcNAcβ ──>
Galβ 4GlcNAcβ 4
              Manα 3
Galβ 4GlcNAcβ 2
``` c. Lewis x: LECAM 2/3

```
Galβ 4
      GlcNacβ 3Galβ ──>
Fucα 3
``` d. Sialyl Lewis x: LECAM 3/2

```
Neu5Acα3Galβ 4
              GlcNacβ 3Galβ ──>
Fucα 3
``` e. Sulfated Lewis x (HNK1): LECAM 1

```
(SO3⁻)3Glc UAβ 3Galβ 4
                      GlcNAcβ 3Galβ 4Glc ──>
Fucα 3
``` f. Oligomannoside: mannose receptor

```
Manα 2Manα 6
             Manα 6
Manα 3              Manβ 4GlcNAcβ 4GlcNAcβ ──>
Manα 2Manα   Manα 3
``` g. Phosphorylated oligomannoside: mannose 6 phosphate receptor

```
(HPO3⁻)6
        Manα 6
Manα 2        Manα 6
(HPO3⁻)6 Manα 3      Manβ 4GlcNAcβ 4GlcNAcβ ──>
         Manα 2 ─Manα 3
Manα 2
``` h. Sulfated oligosaccharide of lactosamin type: sulfated GalNAc 4 receptor

```
(SO3⁻) 4GlcNAcβ 4GlcNacβ 2Manα 6
                                Manβ 4GlcNAcβ 4GlcNAcβ ──>──>
(SO3⁻) 4GlcNAcβ 4GlcNacβ 2Manα 3
```

B) from peptides
a) anti-inflammatory peptides or certain of their fragments recognized by the vascular cells, such as for example:
intestinal vasodilator polypeptide (IPV) HSDAVFTDNYTRLRKQMAVKKYLNSILN-NH₂ (SEQ. ID. NO.: 1)
natriuretic atrial polypeptide (NAP) SLRRSSCFG-GRMDRIGAQSGLGCNSFRY (SEQ. ID. NO.: 2)
lipocortine HDMNKVLDL (SEQ. ID. NO.: 3)
bradykinin RPPGFSPFR (SEQ. ID. NO.: 4);
b) peptide ligands of various integrines, such as peptides containing the sequence RGD (SEQ. ID. NO.: 5) recognized by the receptor of the fibronectine, for instance;
c) chemotactic factors, such as formyl peptides and antagonists: FMLP, (N-formyl-Met-Leu-Phe) (SEQ. ID. NO.: 6);
d) peptide hormones such as α-MSH: Ac-SYSMEHFRWGKPV-NH₂ (SEQ. ID. NO.: 7), for instance,
c) Natural metabolites such as
biotin,
tetrahydrofolate,
folic acid,
carnitin.

In the complexes of the invention, the nucleic acid can be chosen among the following items:
a) gene markers, such as
luciferase gene, β-galactosidase gene,
chloramphenicol acetyl transferase gene,
genes bestowing the resistance to an antibiotic, such as hygromycin or neomycin, b) genes for therapeutic purposes, such as gene encoding
low density lipoprotein receptors, deficient in the case of hypercholesterolomia (liver),
coagulation factors: factors VIII and IX,
phenylalanine-hydroxylase (phenylcetonuria)
adenosine desaminase (ADA immunodeficiency)
lysosomic enzymes, such as b-glucosidase in the case of Gaucher's disease,
dystrophine and minidistriphine (myopathy)
tyrosine hydroxylase (Parkinson),
neuron growth factors (Alzheimer),
CFTR cystic fibrosis transmembrane conductance regulator (mucoviscidose),
alpha1-antitrypsin,
nuclear factors: NF-KB, CII TA, . . .
cytokines and interleukines, TNF: tumor necrosis factor,
thymidine kinase of the Herpes simplex virus,
NO synthase,
angiotensin II receptors,
gene suppressers of tumors, such as the gene for the p53 protein,
MHC proteins, major histocompatibility system, in particular HLA-B7,
antioncogenes: p53, RB
cytosine desaminase,
sense and anti-sense RNA,
ribozymes, c) genes with vaccine purposes: genes encoding
viral antigens, for example, the nucleoprotein of the influenza virus.

One advantageous class of complexes in the invention consists of complexes in which:

the polymer, particularly polylysine, presents a degree of polymerization of approximately 100 to approximately 500, preferably 190, the free $NH_3^+$ functions of the lysine components are substituted up to 60% with gluconoyle groups and possibly by a molecule constituting a recognition signal for 10,000 lysine residues when the said recognition signal possesses an affinity equal or higher than $10^6$ l mole$^{-1}$ in relation to the receptor of the cell which the complex should target, or possibly by 60 recognition signal molecules for 10,000 lysine residues when the said recognition signal possesses an affinity of less than at least $10^4$ l mole$^{-1}$ in relation to the aforementioned receptor, the nucleic acid has a molecular mass of approximately $6.10^5$ to approximately $25.10^6$, and the ratio between the mean number of base pairs of nucleic acid to the number of monomeric components of the polymer, particularly the lysine, is approximately 0.9 to approximately 1.1, preferably approximately 0.9 to approximately 1.05.

The invention also concerns a positively charged polymeric conjugate, the association between the nucleic acid and the polymeric conjugate being electrostatic in nature, the polymeric conjugate containing a polymer formed by monomeric components having free $NH_3^+$ functions of the aforementioned components and being as follows:

the free $NH_3^+$ functions of the aforementioned components are substituted in a ratio of at least 10%, advantageously by 45% to 70%, particularly by 60%, with non-charged residues leading to a reduction of positive charges in comparison with the same non-substituted polymeric conjugate, facilitating the release of nucleic acid by dissociation of the complex, the aforementioned residues possess in addition the following properties:
→they contain at least one hydroxyl group,
→they do not correspond to a recognition signal recognized by a cellular membrane receptor, the free $NH_3^+$ functions of the aforementioned components and/or the hydroxyl groups of the aforementioned residues may also be substituted with at least one molecule which constitutes a recognition signal recognized by a cellular membrane receptor, under the condition that the polymeric conjugate contains at least 30% free $NH_3^+$ functions.

This polymeric conjugate is an intermediate component of the previously described complexes.

In accordance with an advantageous embodiment, the invention concerns a positively charged polymeric conjugate, the association between the nucleic acid the polymeric conjugate being electrostatic in nature, the polymeric conjugate containing a polymer formed by monomeric components having free $NH_3^+$ functions and being as follows:

the free $NH_3^+$ functions of the aforementioned components are substituted in a ratio of at least 10%, advantageously from 45% to 70%, particularly by 60%, with non-charged residues leading to a reduction of positive charges in comparison to the same non-substituted polymeric conjugate, facilitating the release of nucleic acid by dissociation of the complex, the aforementioned residues possess in addition the following properties:
→they contain at least one hydroxyl group,
→they do not correspond to a recognition signal recognized by a cellular membrane receptor, the free $NH_3^+$ functions of the aforementioned components and/or the hydroxyl groups of the aforementioned residues may also be substituted with at least one molecule which constitutes a recognition signal recognized by a cellular membrane receptor, under the condition that the polymeric conjugate contains at least 30% free $NH_3^+$ functions.

In accordance with an advantageous embodiment, the invention concerns a complex between at least one negatively charged nucleic acid and at least one positively charged polymeric conjugate, the association between the nucleic acid and the polymeric conjugate being electrostatic in nature, the polymeric conjugate containing a polymer formed by monomeric components having free $NH_3^+$ functions of the aforementioned components and being as follows:

the free $NH_3^+$ functions of the aforementioned components are substituted in a ratio of at least 10%, advantageously by 45% to 70%, particularly by 60%, by non-charged residues leading to a reduction of positive charges in comparison to the same non-substituted polymeric conjugate, facilitating the release of nucleic acid by dissociation of the complex, the aforementioned residues possess in addition the following properties:
→they contain at least one hydroxyl group,
→they do not correspond to a recognition signal recognized by a cellular membrane receptor, the hydroxyl groups of the aforementioned residues may also be substituted by at least one molecule which constitutes a recognition signal recognized by a cellular membrane receptor, under the condition that the polymeric conjugate contains at least 30% free $NH_3^+$ functions.

The invention also concerns a positively charged polymeric conjugate, containing components which carry free $NH_3^+$ functions, particularly lysine residues, and being as follows:

the free $NH_3^+$ functions of the aforementioned components are substituted in a ratio of at least 10%, advantageously by 45% to 70%, by non-charged residues leading to a reduction of positive charges in comparison to the same non-substituted polymeric conjugate, the aforementioned residues possess in addition the following properties:
→they contain at least one hydroxyl group,
→they do not correspond to a cell recognition signal, the free $NH_3^+$ functions of the aforementioned components may also be substituted by a molecule which constitutes a cellular membrane recognition signal, this recognition signal having a molecular mass lower than 5,000 and when it is present, this recognition signal can exist at the ratio of one molecule for approximately 10,000 monomer components of the polymeric conjugate or approximately 60 molecules for approximately 10,000 monomer components of the polymeric conjugate.

An advantageous class of polymeric conjugates of the invention contains a polymeric group of the following formula:

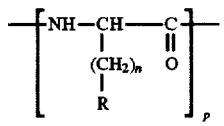

in which:
p is an integer varying from 2 to 500, preferably from 150 to 200, n is an integer varying from 1 and 5 and being preferably 4, this polymeric group contains a number of p of R residues among which:
10% to 70% of the number of R residues represents a NH—CO—(CHOH)$_m$—R$_1$ group, particularly a dihydroxylpropionoyle, erythrononoyle, threonoyle, ribonoyle, arabinoyle, xylonoyle, lyxonoyle, gluconoyle, galactonoyle, mannonoyle, glycoheptonoyle, glycooctonoyle residue, m is an integer from 2 and 15, preferably from 2 to 7, R$_1$ represents H or an alkyl radical from 1 to 15 carbon atoms, particularly CH$_3$, the remaining residues, which are the 30% to 90% of the number of R residues, represent $NH_3^+$, R, moreover, having the ability to be constituted in 0 to 25% of the cases by a molecule which constitutes a recognition signal, under the condition that the polymeric conjugate contains at least 30% free $NH_3^+$ functions, and particularly at the ratio of 0.5 to 5, advantageously at 1 molecule for approximately 10,000 components, or at the ratio of 10 to 100, advantageously at 60 molecules for approximately 10,000 components.

Another advantageous class of polymeric conjugates according to the invention contains a polymeric group of formula (II):

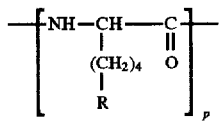

in which
p has the meanings indicated above,
10% to 70% of the number of R residues represents a NH—CO—(CHOH)$_m$—R$_1$ group, m and R$_1$ having the meanings indicated above,
the remaining residues, which are the 30% to 90% of the number of R residues, represent $NH_3^+$.

Another advantageous class of polymeric conjugates according to the invention contains a polymeric group of formula (II):

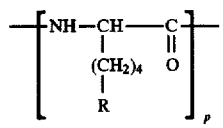

in which:
p has the meanings indicated above,
this polymer contains a number p of R residues among which:
10% to 70% of the number of R residues represents a NH—CO—(CHOH)$_m$—R$_1$ group, m and R$_1$ having the meanings indicated above,
the remaining residues, which are the 30% to 90% of the number of R residues, represent in one part $NH_3^+$ and, in another part, represent a molecule which constitutes a recognition signal at the ratio of 0.5 to 5, advantageously at 1 molecule for 10,000 components.

Another advantageous class of polymeric conjugates according to the invention contains a polymeric group formula (II):

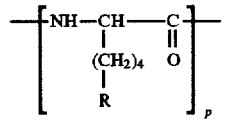

in which:
p has the meanings indicate above,
this polymer contains a number p of R residues among which:
10% to 70% of the number of R residues represents a NH—CO—(CHOH)$_m$—R$_1$ group, m and R$_1$ having the meanings indicated above,
the remaining residues, which are the 30% to 90% of the number of R residues, represent in one part $NH_3^+$ and, in another part, represent a molecule which constitutes a recognition signal at the ratio of 10 to 100, advantageously at 60 molecules for approximately 10,000 components.

In the polymeric conjugates of the invention, the cellular membrane recognition signal could be chosen from those which were clarified for the complexes described above.

The invention also refers to a process of preparation of the complexes described above.

In general terms, a polymer comprising primary amines (free $NH_3^+$ functions) is partially substituted by the reaction with an organic hydroxylated acid (in particular, gluconoic acid), in organic medium.

For example, a polylysine salt (particularly in the form of p-toluene sulfonate) is dissolved in an organic solvent, (particularly dimethylsulfoxide) in the presence of a base (particularly diisopropylethylamine) and treated by an organic hydroxylated activated acid (particularly gluconolactone).

The recognition signals are fixed to the polymer either before or after the introduction of organic hydroxylated acids.

The recognition signals are able to be bound onto ε-amino groups of the polymer or onto hydroxyl groups of organic hydroxylated acids; these substitutions follow any of the protocols known by the person skilled in the art.

As an example of the substitution of the gluconoylated polylysine by recognition signals, the substitution by monosaccharides and oligosaccharides is described.

1) Substitution by monosaccharides.

O-phenylisothiocyanate derivatives of monosaccharides reacted in DMSO in the presence of diisopropylethylamine with the ε-amino groups of the free lysine residues of partially gluconoylated polylysine as previously described in Midoux et al., 1993, Nucleic Acids Res., 21: 871–878.

2) Substitution by oligosaccharides.

Complex oligosaccharides such as asialo of triantennary, tetraantennary, or Lewis x oligosaccharides were transformed into glycopeptides according to the method described by Nadia Normand Sdiqui, 1995, Synthesis of specific glycoconjugates of membrane lectins and their use for targeting oligonucleotides and genes. (University thesis, 5 Jan., 1995, Orléans, France).

Phenylisothiocyanate of glycopeptide derivatives reacted with the ε-amino group of free lysine residues of the gluconoylated polylysine as previously described in: Midoux et al., 1993, Nucleic Acids Res., 21: 871–878.

The nucleic acid/polymer conjugate complex is obtained by mixing a solution of the nucleic acid and a solution of the polymeric conjugate. Preferably, the said solutions are prepared starting from physiologic serum and from a swab "(tampon") or from a cytocompatible medium.

The invention also concerns the use of a complex or of a conjugate according to the invention for the transfection in vitro, ex vivo or in vivo of cells with a gene, particularly those previously defined.

The invention also refers to the use of a complex or a conjugate according to the invention for the transfection of cells which may be chosen from the following:

cells from hematopoietic strains;

liver cells;

cells of skeletal muscles;

skin cells:
  fibroblasts,
  keratinocytes,
  dendritic cells,
  melanocytes.

cells of the vascular walls
  endothelial cells
  smooth muscle cells epithelial cells of the respiratory tract cells of the central nervous system cancer cells;

cells of the immune system, such as lymphocytes, macrophages, NK cells, etc.

A method of in vitro, ex vivo or in vivo transfection in the invention includes the introduction of a complex of the invention into a medium containing cells to be transfected, under conditions such that there exists:

passage of the complex from the medium into the cytoplasm of the cells, release of the nucleic acid of the aforementioned complex into the cytosol of the cells, transcription and expression of the nucleic acid into the transfected cells.

The nucleic acid is delivered into the cytosol and/or into the nucleus of the cell to allow gene expression.

The invention also concerns pharmaceutical compositions, including as an active substance at least one of the complexes or at least one of the conjugates according to the invention, in association with an acceptable pharmaceutical vehicle.

The complexes or conjugates of the invention are also able to be a part of a case or a kit, including for example:

a polymeric conjugate according to the invention, for example, polylysine substituted with a residue leading to a decrease of charges (decrease of the number of the free $NH_3^+$), this polymeric conjugate being possibly substituted with a recognition signal, which beforehand is fixed or not fixed on the polymeric conjugate, the said recognition signal having the function to target the conjugate into selected cells which express a relevant receptor, possibly a plasmid containing at least one gene to be transferred, and the regulation system of the aforementioned gene, reagents permitting the possible fixation of the recognition signal on the aforementioned polymeric conjugate, reagents permitting the formation of a complex according to the invention between the polymeric conjugate and the gene to be transferred, reagents permitting the transfection of the cell by the aforementioned complex.

Concerning the recognition signal, it should be emphasized that it does not necessarily have to be present on the polymeric conjugate. Indeed, it can be a part of the kit and be bound onto the polymeric conjugate before use. Furthermore, the recognition signal may be absent from the kit and the user can add the recognition signal of his/her choice, according to the cells to be targeted, for the transfer on the polymeric conjugate of the kit.

The invention also concerns the use of a complex or a polymeric conjugate, according to the invention, for the preparation of a medicine to be used, for example, for the treatment of a congenital or acquired metabolic deficiency, for the treatment of tumors, or for the preparation of a vaccine such as a vaccine against the influenza virus.

The polymeric conjugates and the complexes of the invention are suitable to be used to transfect ex vivo all cells suited for antigen presentation, for example, precursors of macrophages, macrophages, B cells or dendritic cells.

When one wishes to transfect macrophages, they can be prepared according to the method described by M. Chokri et al. in Anticancer Research 12, 2257–2260, 1992.

The complexes and polymeric conjugates of the invention are suitable to be used for the transfection of macrophages outside of the organism, while in culture environment, before or after separation by elutriation.

One can use a method analogous to that used for the transfection of HepG2 cells, but by using an appropriate oligosaccharide, for example mannose for the mannose receptor (for the transfection of HepG2 cells, one can refer to the examples which follow or to the article by C. Sureau, J. L. Romet-Lemonne, J. Mullins and M. Essex: "Production of hepatitis B virus by a differentiated human hepatoma cell line after transfection with cloned circular HBV DNA." Cell 47, p. 37–47, 1986, or the article by Midoux et al., entitled "Specific gene transfer mediated by lactosylated poly-L-lysine into hepatoma cells." Nucleic Acids Res., 1993, 21, 871–878).

The macrophages transfected "ex vivo" are reinjected into the patient after the verification of the efficacy of the transfection according to the classic methods of immunolabeling.

The nucleic acid in the complex of the invention can be:
a gene with a therapeutic aim to overcome an inherited or acquired metabolic deficiency (for instance coagulation factors such as factor VII or factor IX)
a gene with vaccination purposes (for example a gene encoding either protein expressed on the surface of a tumor, or a virus, bacteria, or parasite protein).

In the case of vaccination by reinjection of transfected macrophages or other antigen presenting cells, the antigenic protein is expressed and is in part presented on the surface of the macrophage, permitting a MHC type 1 dependent antigenic presentation.

The nucleic acid in the complex of the invention is also able to be a gene giving new properties to the macrophages, either directly or by expression of cytokines, cytokines having a direct effect on the macrophage, giving it new physiologic properties
for example:—transfection of the gene of g interferon; in this case the macrophage is permanently autoactivated, thus augmenting its cytotoxic properties; transfection of a modified or unmodified TNFa gene; in this case there is an augmentation of the macrophages' anti-tumoral capacities;
cytokines having an effect on the cellular population in the vicinity of the transfed macrophages;
for example: transfection of the IL2 gene for the stimulation of the cytotoxic T cells in the vicinity of the tumor colonized by the macrophages.

DESCRIPTION OF FIGURES

FIG. 1a:

A fragment of gluconoylated polylysine.

FIG. 1b:

A fragment of polylysine in which some of the $NH_3^+$ functions of the polylysine are substituted such that $R=NH_3^+$ or $NNHCO(CHOH)_m R^1$, $R^1$ having the meanings indicated above.

FIG. 1c:

Electrophoresis analysis of plasmid pSV2Luc complexed with gluconoylated polylysine.

The DNA/gluconoylated polylysine complexes were prepared by adding drop-wise under constant mixing, various quantities (from 0 to 8 μg) of gluconoylated polylysine in 60 μl of DMEM, to 2 μg (0.6 pmol) of plasmid pSV2Luc in 140 μl of DMEM. After 30 minutes at 20° C., 20 μl of each sample was analyzed by electrophoresis through 0.6% agarose gel containing ethidium bromide for visualizing the DNA in Tris borate EDTA buffer (95 mM Tris, 89 mM boric acid, and 2.5 mM EDTA), pH 8.6. pLK-GlcA/DNA ratios: 0 (a), 15 (b), 30 (c), 60 (d), 90(e), 120 (f), 150 (g), 180 (h), 210 (i) and 240 (j).

FIG. 2a:

Gene transfer in HepG2 cells, using gluconoylated polylysines (GlcA-pLK).

The average number of gluconoyle residues per polylysine molecule was determined by a colorimetric assay.

The DNA/polymer complexes formed between the pSV2Luc plasmid and the polylysine substituted by different quantities of gluconoyle residues (from 15 to 70%) have been determined by electrophoresis in agarose gel. The polylysine substituted by more than 140 gluconoyle residues is not able to form a complex with a plasmid stable enough.

The HepG2 cells were incubated at 37° C. for 4 hours in the presence of 100 μM of chloroquine with 1.5 nM of plasmid complexed with each conjugate. The medium was discarded and the cells were further incubated in the absence of both chloroquine and plasmid. Expression of the gene of luciferase was determined 48 hours later by measuring the activity of luciferase in the cellular lysates. The relative light units (RLU) emitted were expressed per mg of protein which corresponds to 1.2 million of HepG2 cells, as a function and of the molar ratio GlcA/pLK and the degree of substitution of polylysine (%).

Figure 2A:
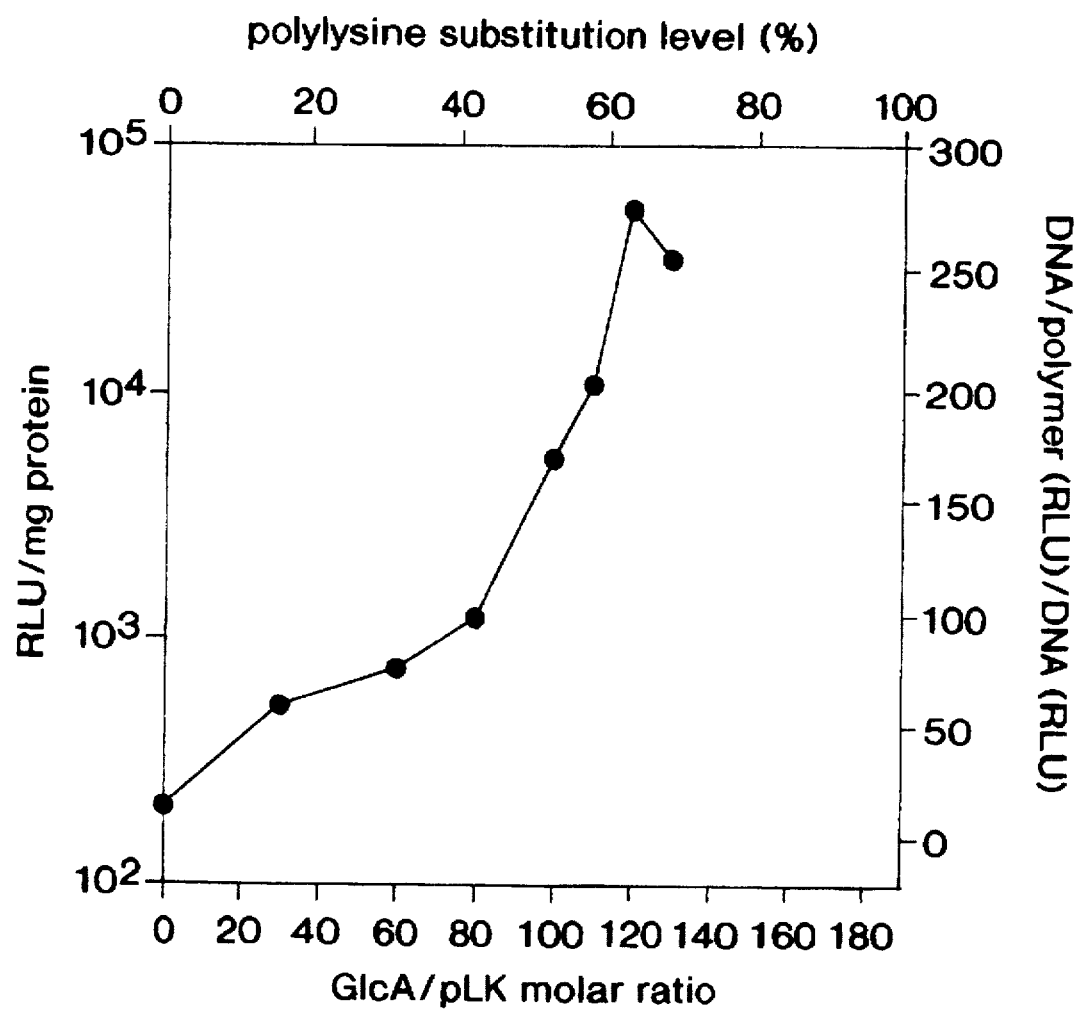

FIG. 2b:

Gene transfer into HepG2 cells using gluconoylated polylysines under identical conditions as those described for FIG. 2a.

The difference from FIG. 2a is that the average number of gluconoyle residues per polylysine molecule was determined from the NMR spectra.

FIG. 2c:

Formation of DNA/gluconoylated polylysine complexes. FIG. 2c concerns notably the study of the amount of gluconoylated polylysine complexed per DNA molecule (plasmid of 5 kb) as a function of the gluconoylated polylysine/DNA molar ratio (P/DNA). The DNA/gluconoylated polylysine complexes were formed in 1 ml of DMEM between the pSV2Luc plasmid (3 pmole) and gluconoylated polylysine labeled with fluorescein and containing 70 gluconoyle residues. The complexes were spun down from their solution by centrifugation at high speed. The amount of gluconoylated polylysine associated to a DNA molecule (white columns) is the total amount of gluconoylated polylysine (determined by measuring the absorbance at 495 nm of the solution before centrifugation: hatched column) minus the amount of the free gluconoylated polylysine (determined by measuring the absorbance at 495 nm of the supernatant after centrifugation: black column).

Figure 2B:
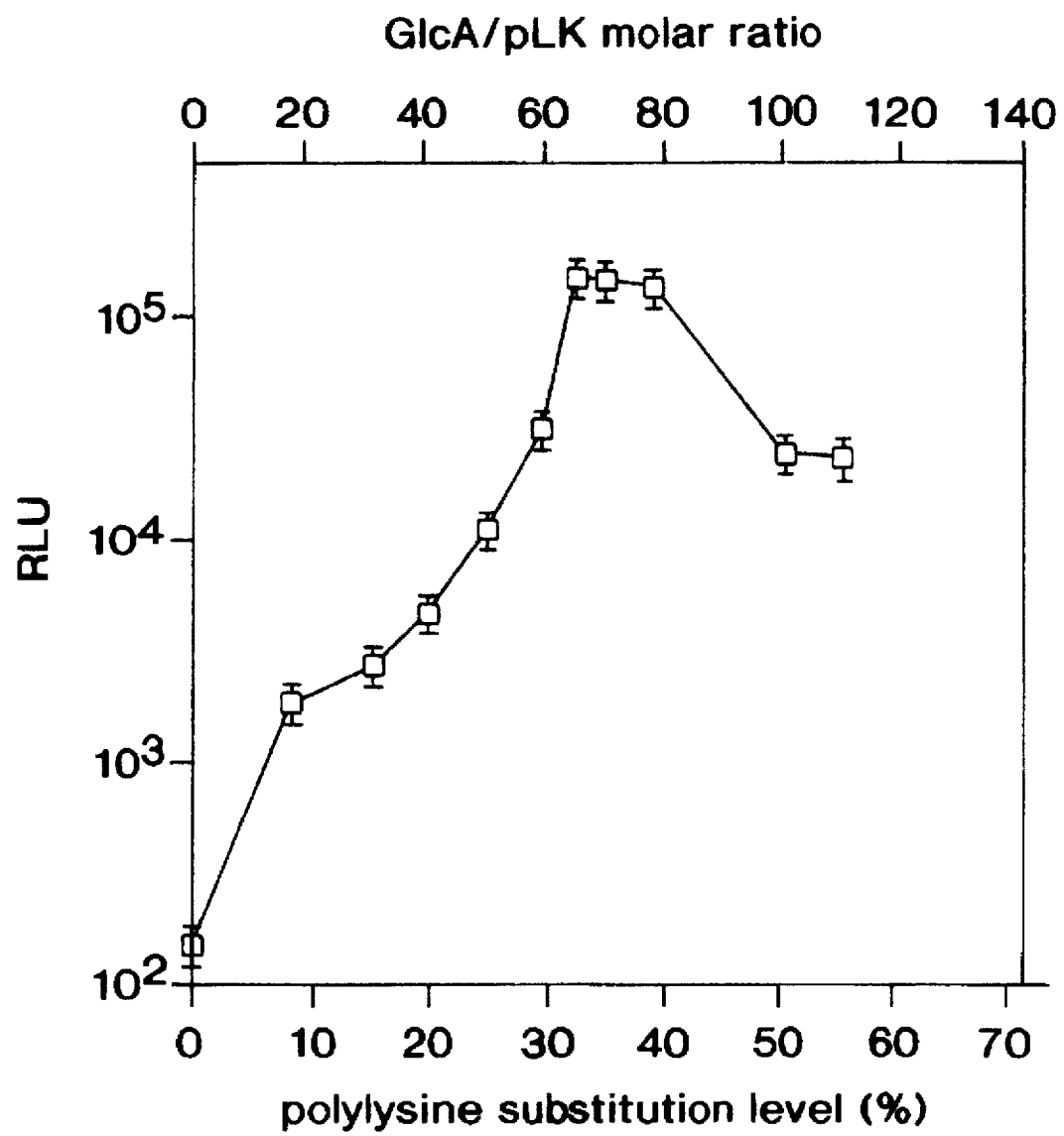
Figure 2C:
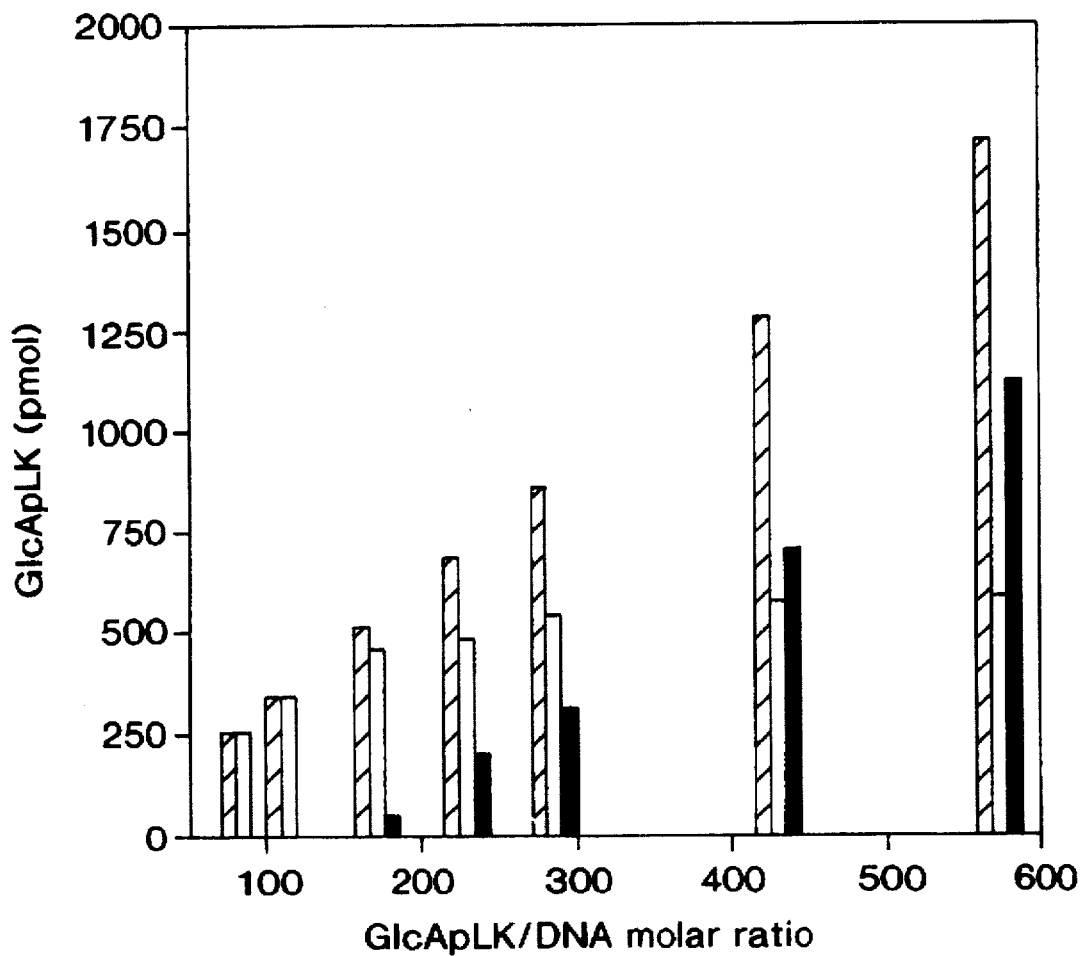
Figures 1, 2D:
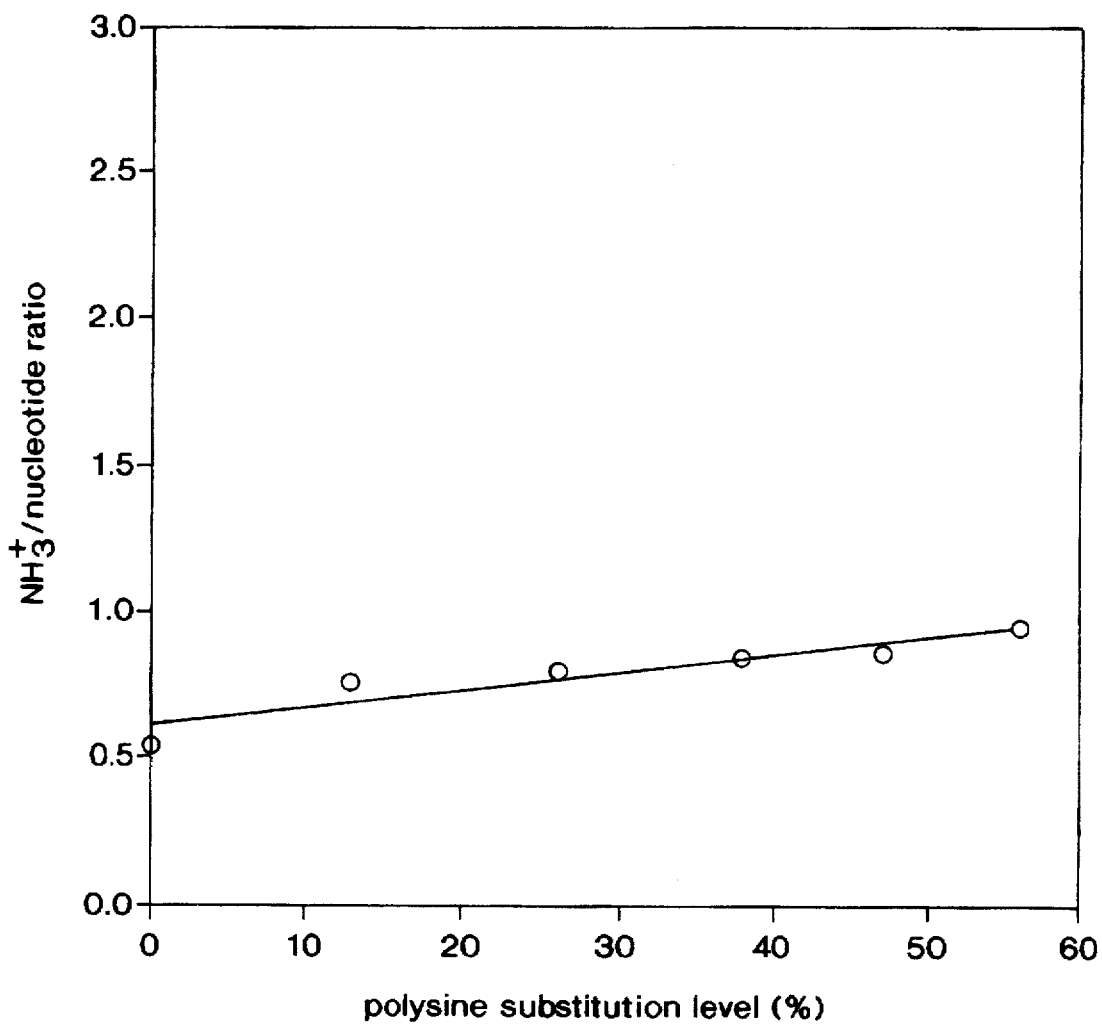
Figures 2, 2D:
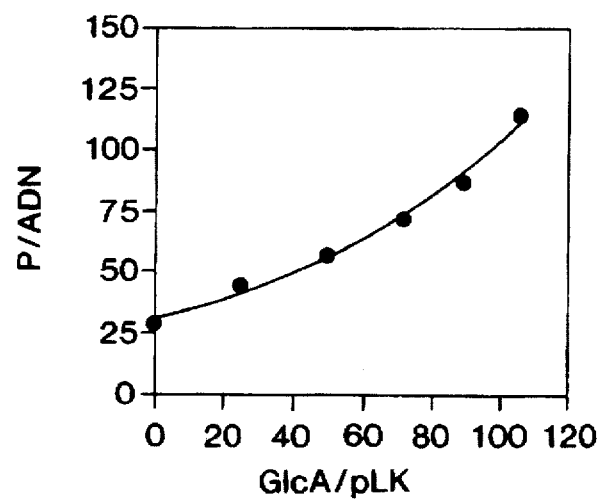
Figure 3A:
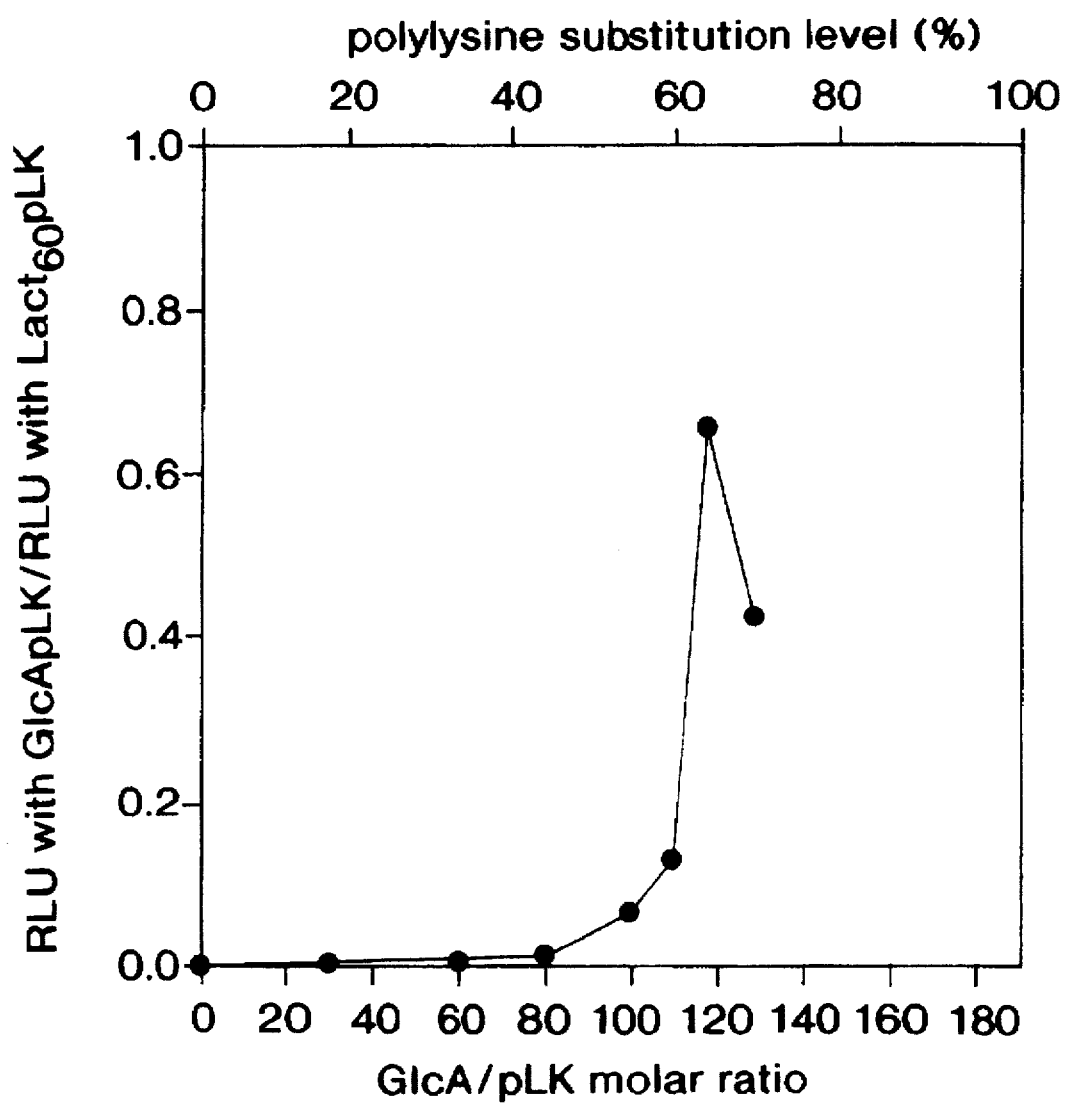
Figure 3B:
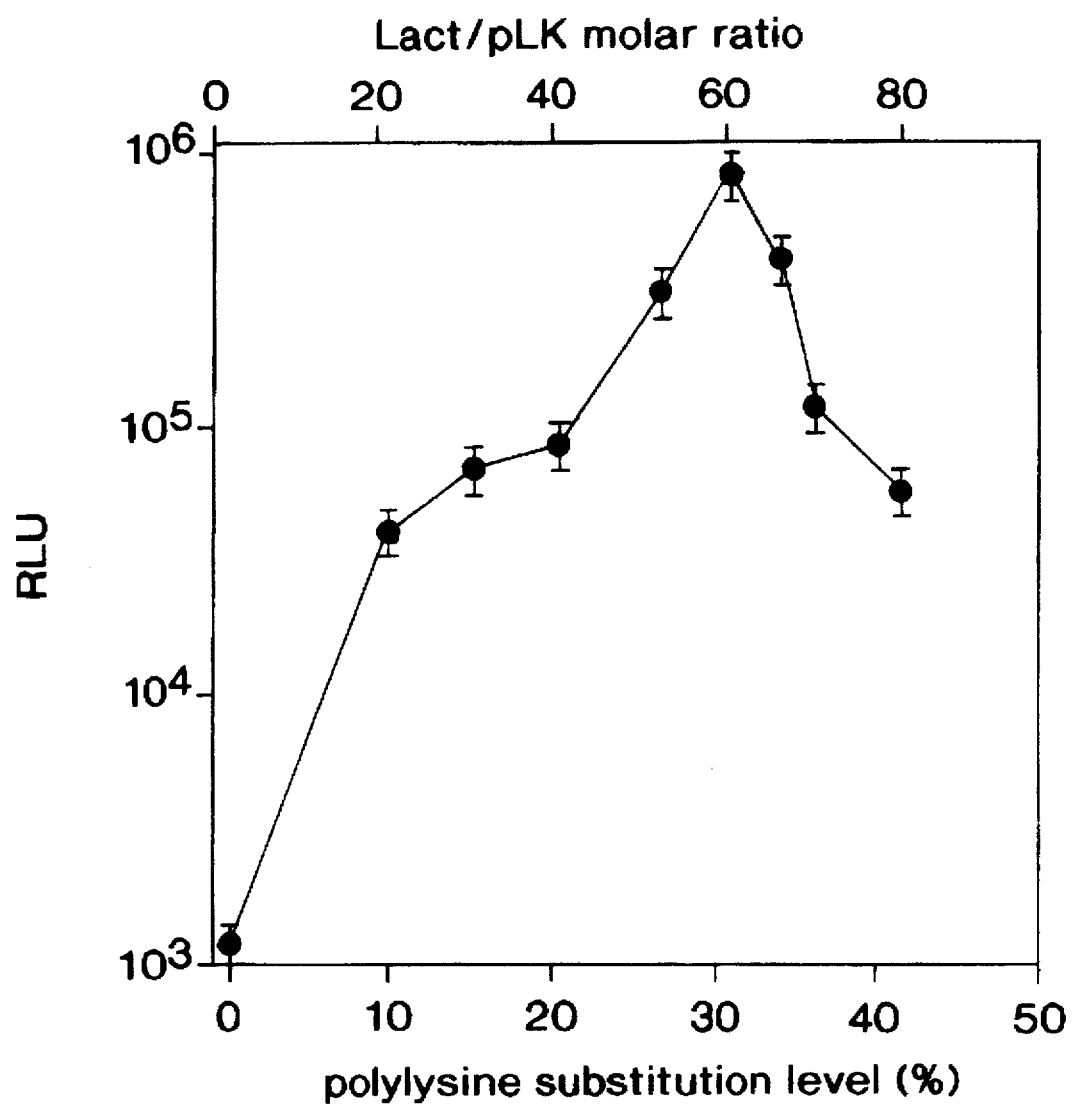

FIGS. 2d-1 and 2D-2:

Formation of DNA/gluconoylated polylysine complexes as a function of the number of gluconoylated residues bound per polylysine molecule.

The DNA/gluconoylated polylysine complexes are formed in 0.2 ml of DMEM between the pSV2Luc plasmid (0.6 pmole) and gluconoylated polylysines containing up to 110 gluconoyle residues. The $NH_3^+$/nucleotide ratio represents the number of positive charges per gluconoylated polylysine multiplied by the number of gluconoylated polylysine per DNA divided by the number of negative charges carried by the DNA into complexes with the smallest gluconoylated polylysine/DNA molar ratio inducing a complete retardation of all the DNA in electrophoresis. Insert: Variation of the amount of gluconoylated polylysine per DNA molecule in complexes with the smallest gluconoylated polylysine/DNA molar ratio inducing a complete retardation of all the DNA in electrophoresis. P/DNA is the gluconoylated polylysine DNA molar ratio; GlcA/pLK is the average number of gluconoyle residues per polylysine molecule.

FIG. 3a:

Gene transfer into the HepG2 cells using gluconoylated polylysine (GlcA-pLK).

The DNA/polymer complexes formed between the pSV2Luc plasmid and the polylysine substituted by different quantities of gluconoyle residues (from 15 to 70%) were determined by electrophoresis on agarose gel. The polylysine substituted by more than 140 gluconoyle residues is not able to form a complex with the plasmid stable enough. The HepG2 cells were incubated at 37° C. for 4 hours in presence of 100 μM of chloroquine with 1.5 nM of plasmid complexed with each conjugate. The medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed in relation to those obtained in the same experiment where the transfection of HepG2 cells was with the lactosylated polylysine conjugate ($Lact_{60p}pLK$). In graph form, we represented the RLU/RLU values of the $Lact_{60}pLK$ as a function of the molar ratio GlcA/pLK in one part, and by degree of substitution by polylysine (%).

FIG. 3b:

The figure concerns the influence of the number of lactose residues.

The optimal activity of a polymeric conjugate (polymer substituted by lactoses) appears when 30% of the $NH_3^+$ groups are substituted by lactose.

FIG. 4:

The figure concerns gene transfer in different cells using gluconoylated polylysine (GlcA-pLK) using pSV2Luc plasmid.

A DNA/polymer complex was formed between the pSV2Luc plasmid and the polylysine substituted by 120 gluconoyle residues. The cells were incubated at 37° C. for 4 hours in the presence of 100 μM of chloroquine with 1.5 nM of plasmid complexed with the gluconoylated polylysine.

The medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed per mg of protein. The relative light units (RLU) emitted were expressed per mg of the protein. MacroH=human macrophages derived from monocytes; RBE4=rat brain endothelial cells; HEL=leukemic cells of the erythroid lineage.

FIG. 5:

Gene transfer in different cells using gluconoylated polylysine (GlcA-pLK) using CMVLuc plasmid.

A DNA/polymer complex was formed between the CMV-Luc plasmid and the polylysine substituted by 120 gluconoyle residues. The cells were incubated at 37° C. for 4 hours in the presence of 100 μM of chloroquine with 1.5 nM of plasmid complexed with gluconoylated polylysine. The medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed per mg of protein. 3LL=cells (mouse) of Lewis lung carcinoma; MacroH=human macrophages derived from monocytes; RBE4=rat brain endothelial cells; HepG2=human hepatocarcinoma; HEL=leukemia cells of the erythroid lineage; K562=another leukemic cell of the erythroid lineage.

FIG. 6

The figure concerns the measure of the dissociation of the complexes formed between the pSV2Luc plasmid and the polylysine (degree of polymerization=190) substituted with lactose.

Complexes were formed between the pSV2Luc plasmid with either the polylysine (pLK), the polylysine substituted by 60 residues of lactose ($Lact_{60}pLK$), or polylysine substituted by 80 residues of lactose ($Lact_{80}pLK$). The complexes were formed in a solution of 0.15M NaCl; the concentration of NaCl was then increased. The solutions of DNA/polymer complexes at different concentrations in NaCl were filtered through a 0.45 mm nitrocellulose membrane. In this experiment, the DNA non-complexed to the polylysine passes through the filter while the complexed DNA is retained by the filter. The quantity of DNA dissociated from the polylysine was determined by measuring the quantity of DNA present in the filtrates using DAPI (4',5-diamino-2-phenylindole), (lem=450 nm; lexc=360 nm) (Sigma)) as fluorescent probe. We graphed the percentage of bound DNA/free DNA ratio as a function of the concentration of NaCl (M). ○ corresponds to pLK, ● corresponds to pLK.-$Lact_{60}$, and ▽ corresponds to pLK.-$Lact_{80}$.

FIG. 7a:

The figure concerns the measure of the solubility of the complexes.

Complexes of DNA/polymer were formed in a solution of 0.15M NaCl between pSV2Luc plasmid with either the polylysine (pLK), the gluconoylated polylysine ($GlcA_{120}pLK$), or with polylysine substituted by 60 residues of lactose ($Lact_{60}pLK$). After 30 minutes at 20° C., the absorbency at 610 nm of the solutions was measured.

FIG. 7b:

Measurement of the solubility of complexes.

DNA/polymer complexes were formed in 0.15M NaCl between the pSV2Luc plasmid and the polylysine substituted with either 30 lactosyle residues (pLK, -$Lact_{30}$) (empty squares), or 30 lactosyle residues and 50 gluconoyle residues (pLK, -$Lact_{30}$, $GlcA_{50}$) (black triangles). After 30 minutes at 20° C., the absorbance at 610 nm of the solutions was measured.

FIG. 8:

Gene transfer in a myeloid cell line.

HEL myeloid cells were transfected by a complex made between a plasmid containing the luciferase gene (PUT650) and the gluconoylated and biotinylated polylysine. This complex is then associated with the biotinylated Stem Cell Factor (SCF) by the intermediary of streptavidin. The RLU histogram values were expressed in relative units of luminescence per mg of protein extracts. The transfections were realized with (A) the plasmid alone, (B) the plasmid complexed to the gluconoylated and biotinylated polylysine, (C) the complex (plasmid/gluconoylated biotinylated polylysine) associated with the streptavidin and (D) the complex (plasmid/gluconoylated biotinylated polylysine) associated with the streptavidin and with the stem cell factor.

FIG. 9:

NMR spectrum at 300 MHz in $D_2O$ of polylysine, p-toluene sulfonate 1.28 to 1.88 ppm: 6H of carbons 3, 4 and 5 of the lysine 2.41 ppm: $CH_3$ group of the p-toluene sulfonate 2.84 to 2.95 ppm: 2H of carbon 6 4.3 ppm: 1H of carbon 2 7.38 and 7.7 ppm: aromatic protons of p-toluene sulfonate

FIG. 10:

NMR spectrum at 300 MHz in $D_2O$ of the polylysine substituted with 73 gluconoyle residues. 1.28 to 1.88 ppm: 6H of carbons 3, 4 and 4 of lysine 2.41 ppm: $CH_3$ group of p-toluene sulfonate 2.75 ppm: trace of DMSO 2.97 ppm: 2H of carbon 6 of non-gluconoylated lysine residue 3.26 ppm: 2H of carbon 6 of a gluconoylated lysine residue 3.68 to 3.88 ppm: 4H of a gluconoyle residue (see spectrum number 1,856B in: The Aldrich Library of $^{13}$C an $^1$H FTNMR Spectra, Ed I, C. J. Pouchert and J. Behnke, Vol. 1) 4.3 ppm: 1H of carbon 8 of a gluconoyle residue and 1H of carbon 2 of a lysine residue

Figure 11:
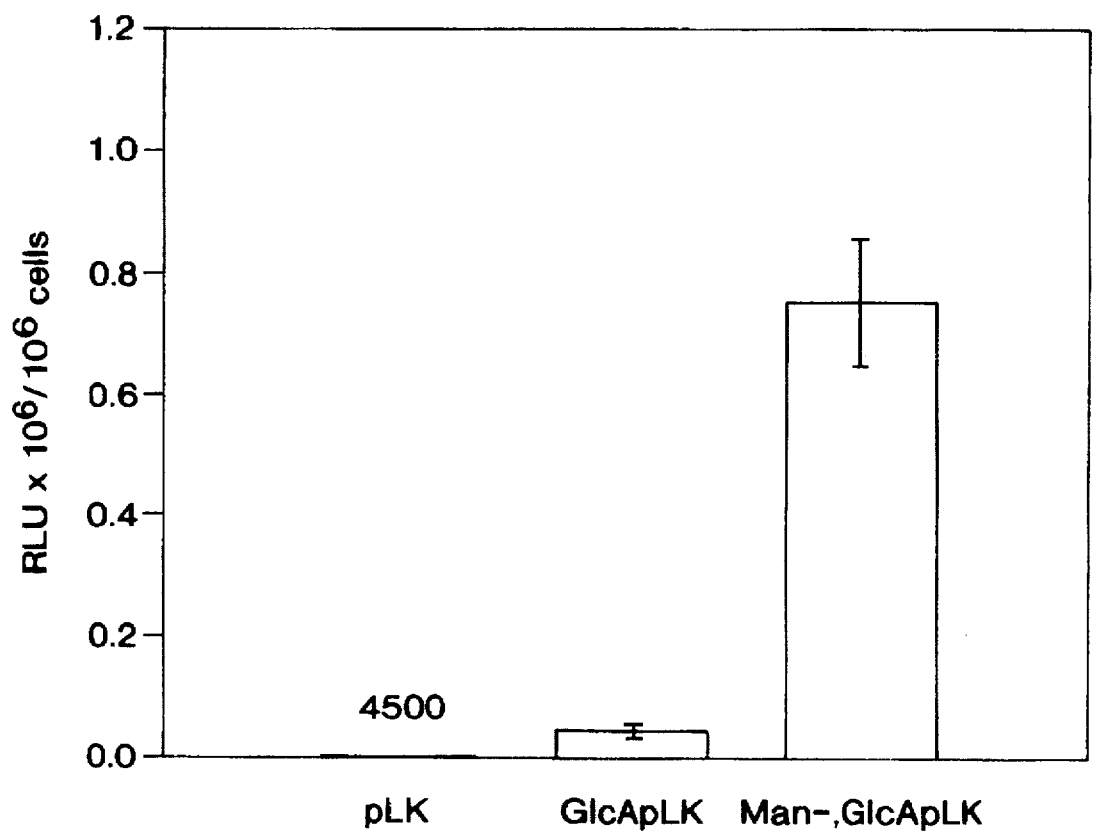

FIG. 11:

Human macrophages possess a mannose/fucose receptor and take up mannosylated or flucosylated macromolecules. As shown in FIG. 11, the transfection efficiency of human macrophages is 16 fold greater when partially gluconoylated polylysine is substituted with mannose residues.

Figure 12:
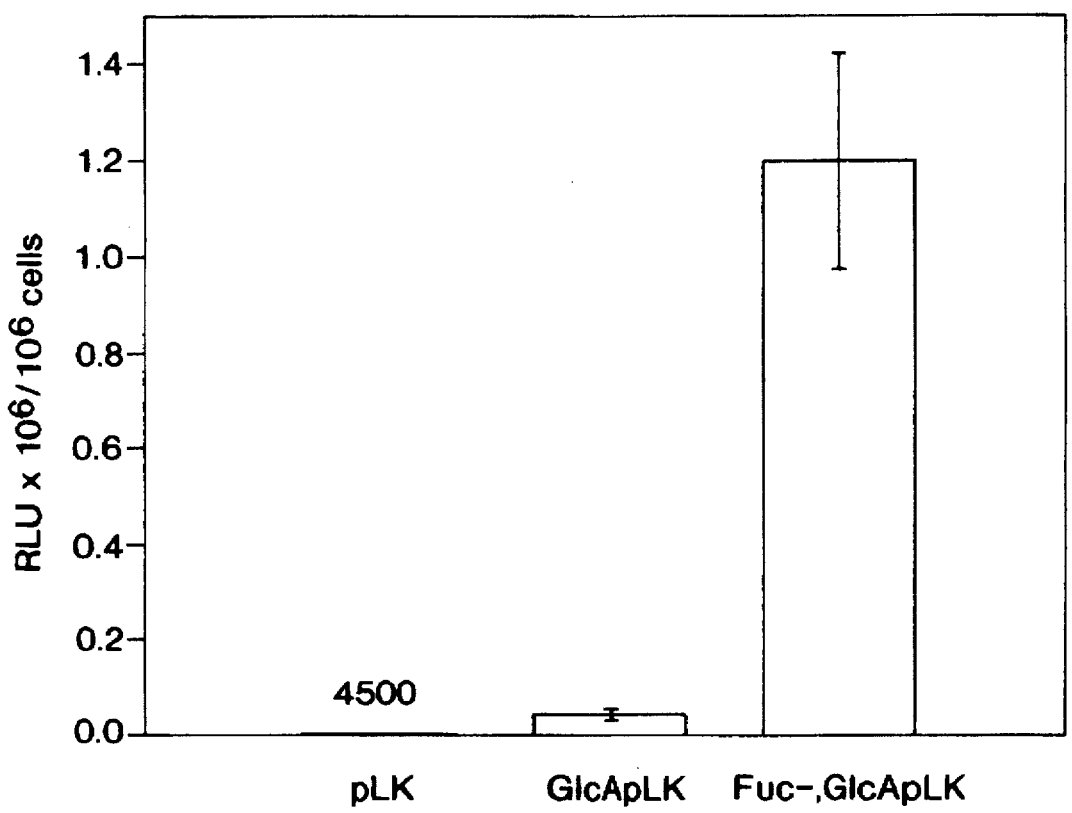

FIG. 12:

Human macrophages possess a mannose/fucose receptor and take up mannosylated or fucosylated macromolecules. As shown in FIG. 12, the transfection efficiency of human macrophages is 27 fold greater when partially gluconoylated polylysine is substituted with fucose residues.

Figure 13:
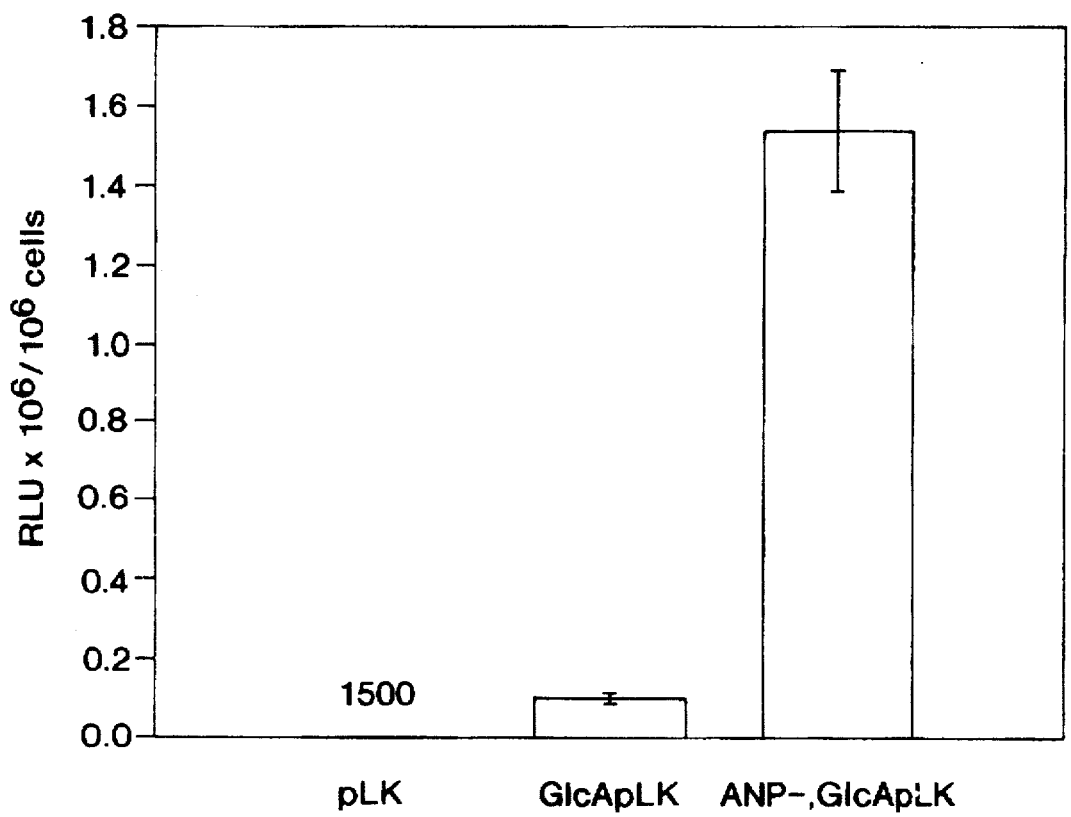

FIG. 13:

The rabbit smooth muscle cell line, Rb-1 cells, possess a receptor for the peptide ANP. As shown in FIG. 13, the transfection efficiency of Rb-1 cells is 15 fold greater when partially gluconoylated polylysine is substituted with ANP residues.

Figure 14:
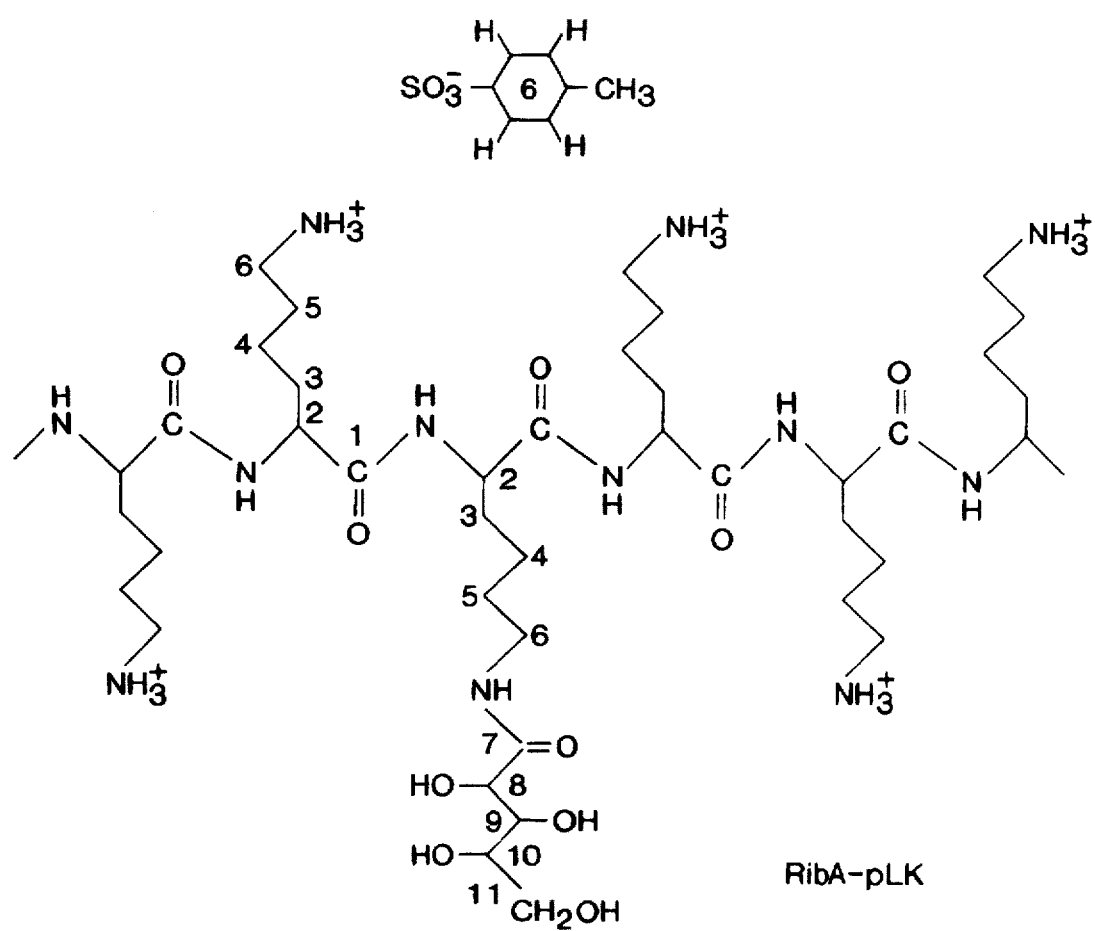
Figure 15:
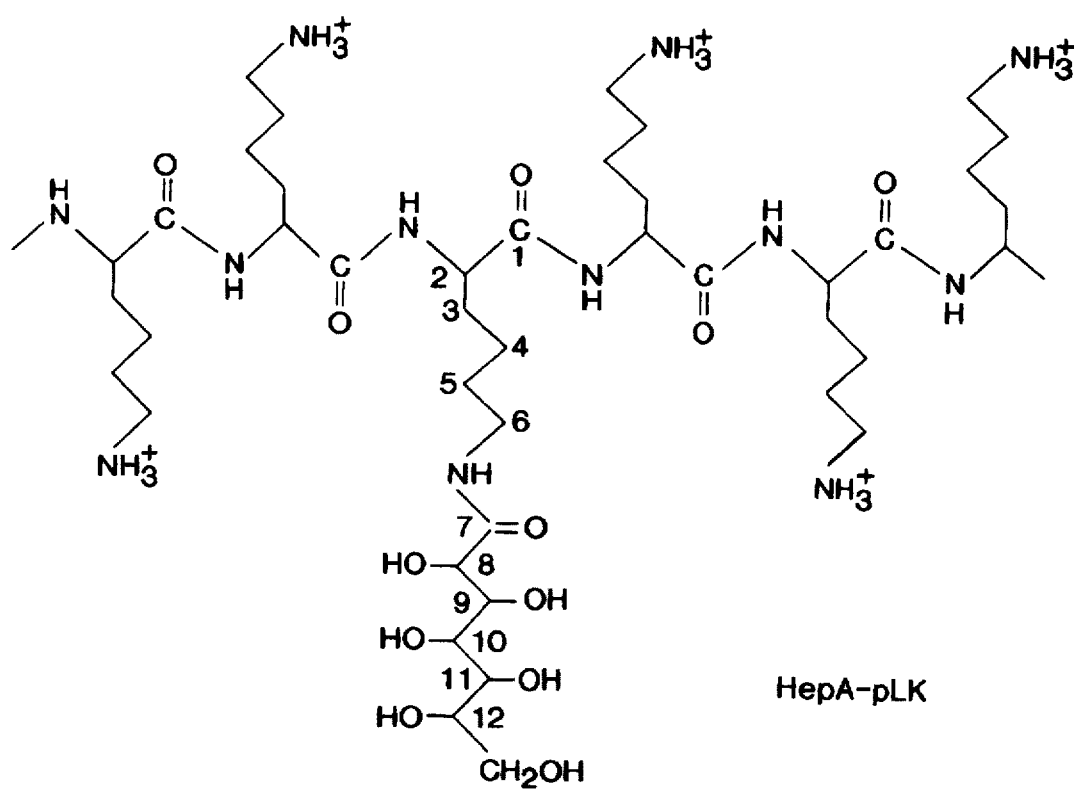
Figure 16B:
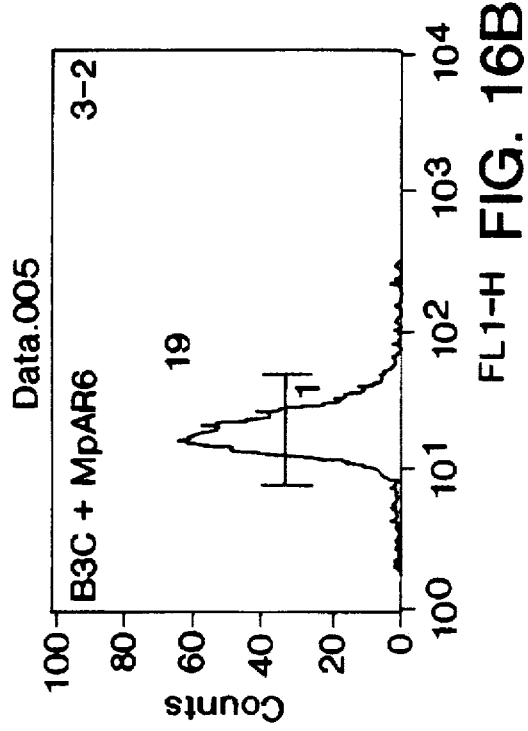
Figure 16D:
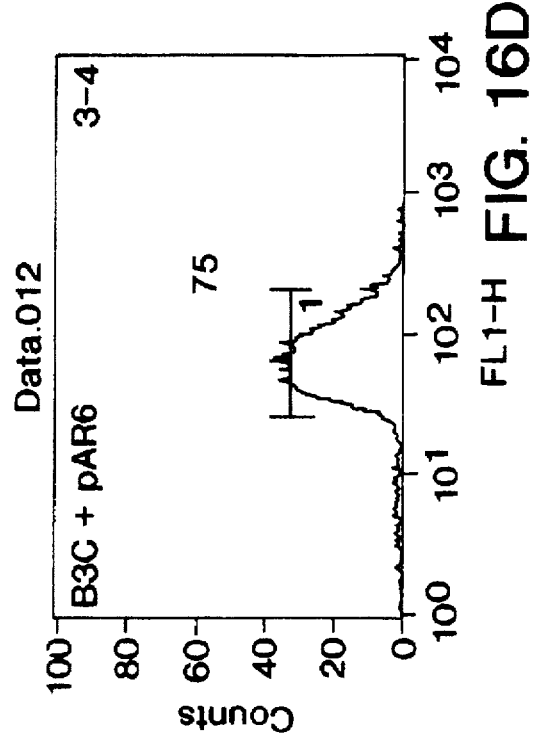
Figure 16A:
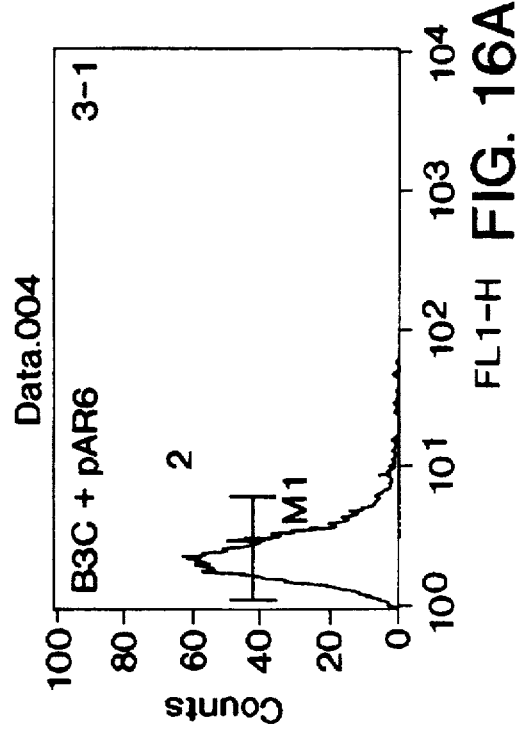
Figure 16C:
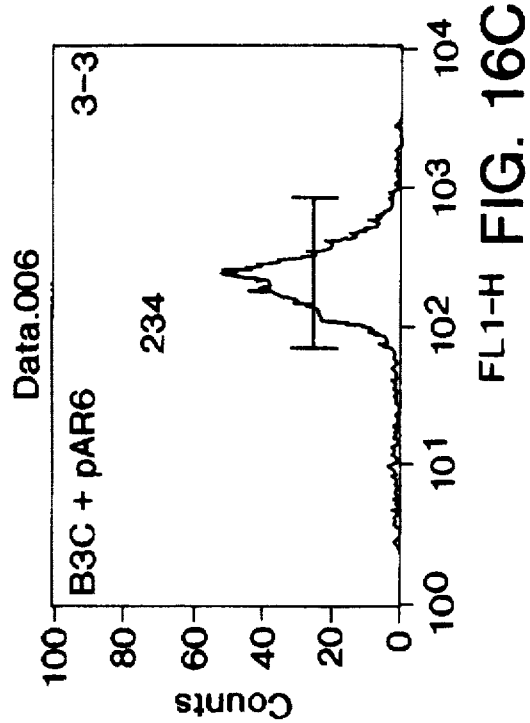
Figure 17:
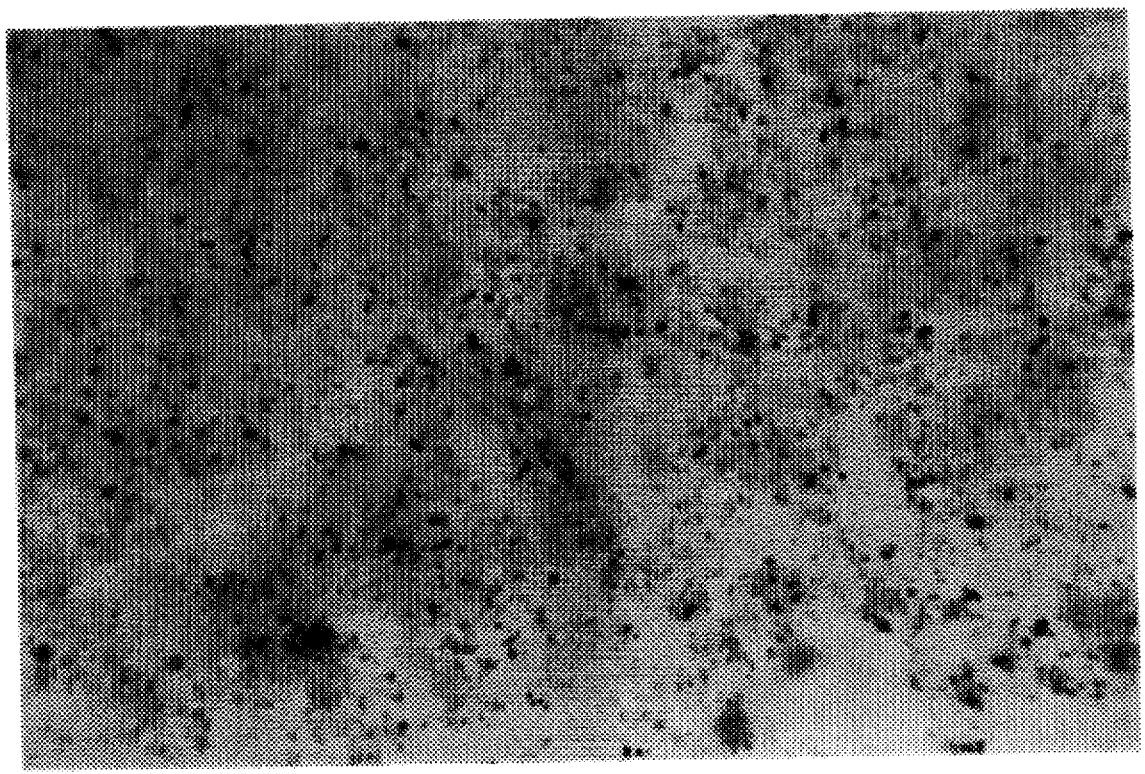
Figure 18:
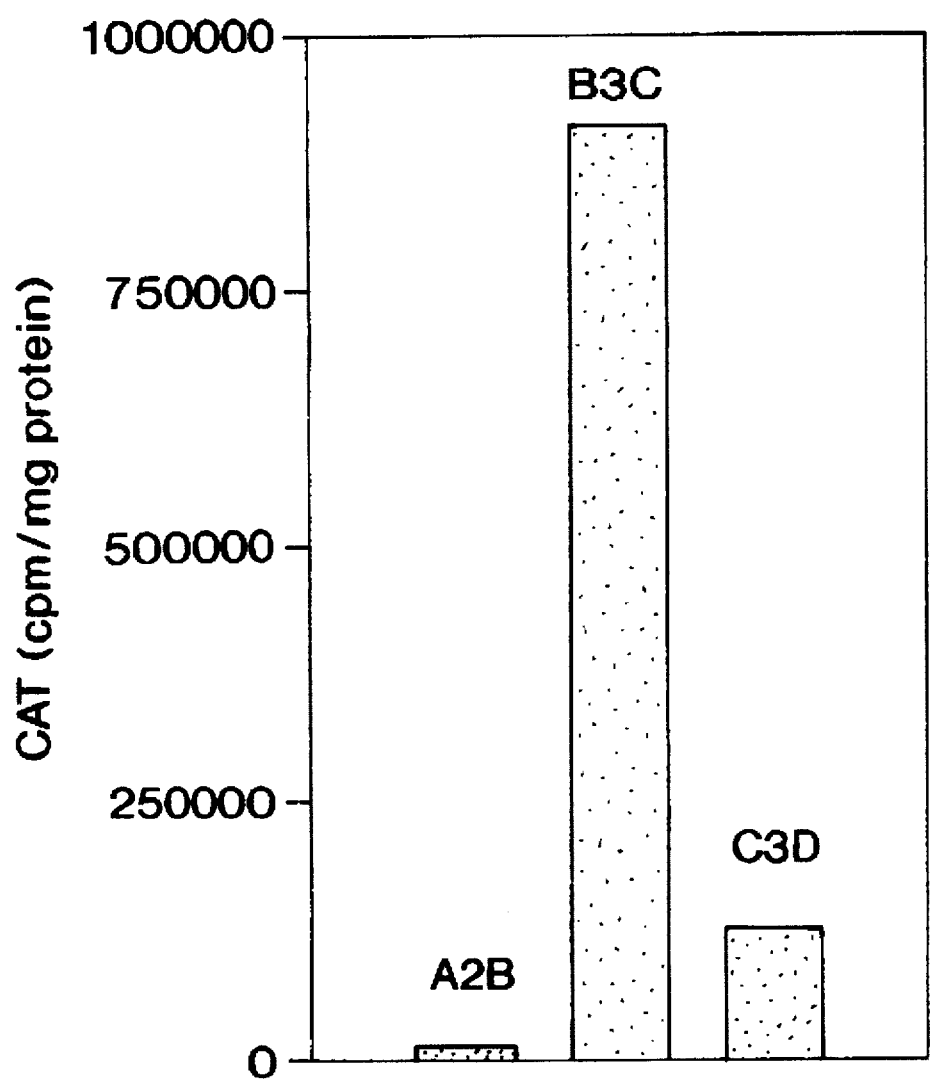

FIG. 14 is a fragment of ribonoylated polylysine,

FIG. 15 is a fragment of heptanoylated polylysine;

FIGS. 16A–D is a flow cytometry analysis of the inhibition of the expression of the CAT marker protein by transfection with a plasmid encoding a specific antisense RNA. 3:1 and 3:2 negative controls. 3:3 positive control. 3:4 as in 3:3 but in the presence of the antisense plasmid;

FIG. 17 shows the efficacy of transfection wherein the nucleus of cells expressing a large amount of galactosidase is blue FIG. 18 shows the efficiency of the expression in stable transfectants

Figure 19A:
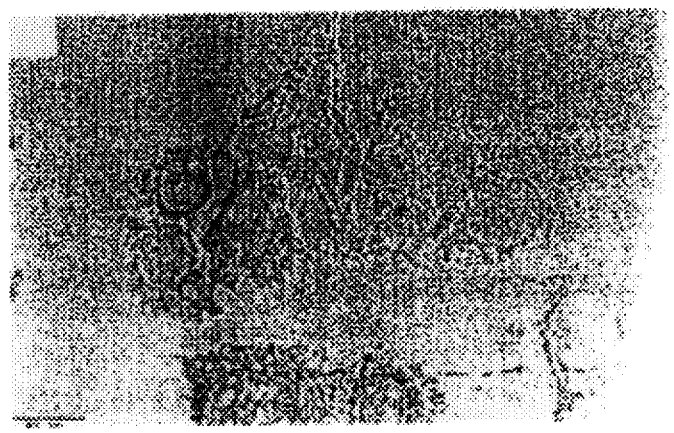
Figure 19B:
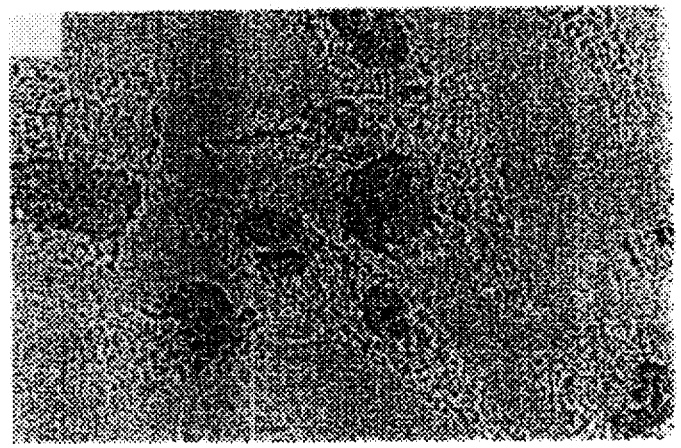

FIG. 19:

FIG. 19a corresponds to non transfected cells. FIG. 19b corresponds transfected cells, over expressing tat in their nucleus.

Figure 20A:
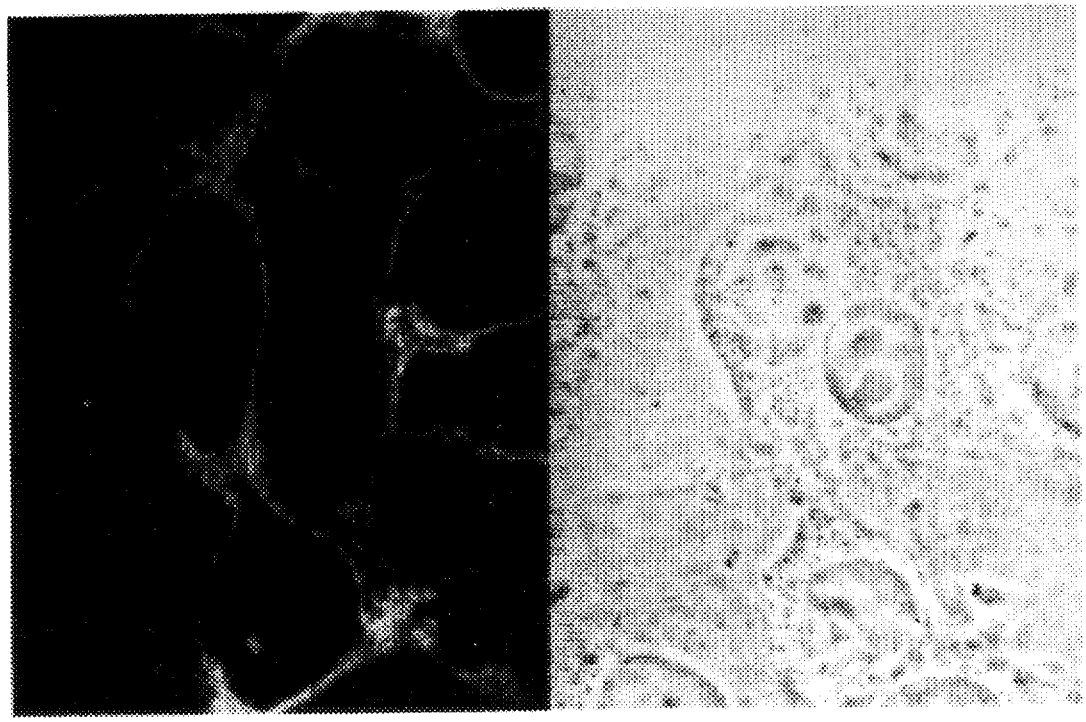

FIGS. 20A and B:

Confocal analysis of COS cells transfected with pc DNA$_3$MR 48 h after cell transfection, cells were fixed, permeabilized with saponin and incubated with fluoresceinylated mannosylated serum albumin. A high cytoplasmic fluorescence evidenced the over expression of MR60 (B, arrow). In control experiments with fluoresceinylated sugar-free serum albumin, the cytoplasm was not labelled (A).

Left panel: laser confocal fluorescence images corresponding to a central section; right panel : contrast phase images.

Figure 21:
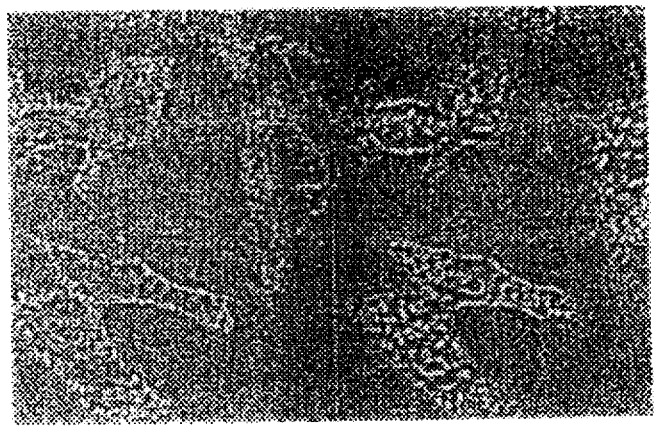

FIG. 21 shows the expression of the vital antigen with cells specifically labelled with anti-nucleoprotein antibodies.

Table 1. Transfection of HepG2 cells by lactolysated and gluconoylated polylysine.

| RLU × 10$^{-3}$/mg of protein | 5.2 | 19 | 671 | 650 |
|---|---|---|---|---|
| Lact/pLK | 0 | 30 | 30 | 60 |
| GlcA/pLK | 0 | 0 | 30 | 0 |

HepG2 cells were incubated at 37° C. in the presence of 100 μM of chloroquine and 1.5 nM of plasmid complexed with each of the conjugates. After 4 hours, the medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed per mg of protein which corresponds to 1.2 million cells of HepG2. Lact/pLK is the number of lactose molecules per polylysine molecule, and GlcA/pLK is the number of gluconoyle molecules per polylysine molecule.

Table II. Transfection of HepG2 cells by gluconoylated and biotinylated polylysine.

| | RLU/mg of protein |
|---|---|
| DNA/GlcA, Bio-pLK/Strep/Bio-LactBSA | 966000 |
| DNA/GlcA, Bio-pLK/Strep/Bio-BSA | 248000 |
| DNA/GlcA, Bio-pLk/Strep | 237000 |
| DNA/GlcA, Bio-pLK | 67000 |
| DNA | 200 |

HepG2 cells were incubated at 37° C. in the presence of 100 μM of chloroquine with 1.5 nM of free plasmid or plasmid complexed with each of the conjugates. After 4 hours, the medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed per mg of protein which corresponds to 1.2 million cells of HepG2. GlcA,Bio-pLK=polylysine substituted by 60 gluconoyles and 2.5 biotins; Strep=streptavidin; Bio-LactBSA=lactolysated and biotinylated albumin serum; Bio-BSA=biotinylated albumin serum.

Chemical Components

Luciferine, chloroquine, Triton X 100 and bicinchoninic acid from Sigma (St. Louis, Mo., USA); L-glutamin, dimethylsulfoxide (Me$_2$SO), ATP, glycerol and MgCl$_2$ from Merck (Darmstadt, Germany); dithiothreitol and D-gluconolactone from Serva (Heidelberg, Germany); diisopropylethylamine, sulfonic p-toluene acid, EDTA from Aldrich (Strasbourg, France); Dowex 2×8, (diameter 0.3–0.9 mm) from Bio-Rad (Richmond, Calif. USA); 4-isothiocyanatophenyl-b-D-lactoside, 4-isothiocyanatophenyl-b-D-galactopyranoside were prepared as previously described (Monsigny M., Roche A. C. and Midoux P., Uptake of neoglycoproteins via membrane lectins of L 1210 cells evidenced by quantitative flow cytofluorometry and drug targeting. Biol. Cell., 1984: 51: 187–96); the poly-L-lysine, Hbr (30 000–50 000, average molecular mass=40 000, polymerization degree=190) comes from Bachem Feinchemikalien (Bubendorf, Switzerland). The poly-L-lysine, HBr (1 g in 200 ml of H$_2$O) is passed through an anion exchange column (Dowex 2×8, in OH form, 0.3–0.9 mm diameter, 35×2.5 cm) in order to take away the bromure (Derrien D., Midoux P., Petit C., Negre E., Mayer R., Monsigny M., and Roche A. C., Muramyl dipeptide bound to poly-L-lysine substituted with mannose and gluconoyle residues as macrophage activators. Glycoconjugate J., 1989: 6: 241–55) which is very cytotoxic for the cells (Weiss S. J., Test S. T., Eckmann C. M., Roos D., and Regiani S., Brominating oxidants generated by human eosinophils. Science, 1986: 234: 200–202). The effluent solution is neutralized with 10% p-toluene sulfonic acid in water (a non-cytotoxic compound) and lyophilisated. The lactolysated bovine albumin serum (Lact-BSA, comprised of a mean number of 39 lactose residues) is prepared as previously described (Roche A. C., Barzilay M., Midoux P., Junqua S., Sharon N., and Monsigny M., Sugar-specific endocytosis of glycoproteins by Lewis lung carcinoma cells. J. Cell. Biochem., 1983: 22: 131–40; Monsigny M., Roche A. C., and Midoux P., Uptake of neoglycoproteins via membrane lectin(s) of L 1210 cells evidenced by quantitative flow cytofluorometry and drug targeting. Biol. Cell., 1984: 51: 187–96).

Preparation of the gluconoylated polylysine

The poly-L-lysine in hydromide form, pLK,HBR 30,000–50,000 (molecular mass average=40,000; mean degree of polymerization=190) from Bachem Feinchemikalien (Bubendorf, Switzerland). The polylysine, HBr (1 g in 200 ml $H_2O$) is passed through an anion exchange column (Dowex 2x8, in OH form, 35x2.5 cm) in order to take away the bromide which is toxic for the cells. The polylysine solution is neutralized with a solution of sulfonic p-toluene acid at 10% in water then lyophilisated.

The polylysine is partially substituted with gluconoyle residues (GlcA) as follows: the polylysine in p-toluene sulfonate form (50 mg; 0.86 mmoles) dissolved in 3 ml of DMSO (dimethylsulfoxide) in the presence of diisopropylethylamine (37 ml; 205 mmoles) and 1% of water, is allowed to react for 24 h at 20° C. with quantities of D-gluconolactone ranging from 11 mg (61 mmol) to 35 mg (194 mmol). The gluconoylated polylysine is precipitated by adding 10 volumes of isopropanol. After centrifugation (1,800 g×15 min), the pellet is washed with isopropanol and collected after another centrifugation. The pellet is dissolved in bidistilated water and the solution is lyophilisated. The mean number of fixed gluconoylated residues per molecule of polylysine, determined by measuring the mean number of free $\epsilon$-$NH_2$ lysine residues remaining on the polylysine by using the TNBS colorimetric method (TNBS=sulfonic 2,4, 6,-trinitobenzene acid) (Fields R., The measurement of amino groups in proteins and peptides. Biochem. J., 1971: 124: 581–90), is found equal to 105±15. The mean molecular mass is 58,000.

Preparation of conjugates of lactolysated gluconoylated polylysine

The polylysines substituted with either 30 lactose residues ($Lact_{30}$pLK) or with 60 lactose residues ($Lact_{60}$pLK) were prepared as previously described (Midoux P., Mendes C., Legrand A., Raimond J., Mayer R., Monsigny M., and Roche A. C. Specific gene transfer mediated by lactosylated poly-L-lysine into hepatoma cells. Nucleic Acids Res., 1993: 21: 871–78). The lactolysated polylysine containing 30 lactose residues (50 mg: 0.745 mmol) is allowed to react for 24 h at 20° C. with the D-gluconolactone (7.6 mg; 43 mmol) in the presence of diisopropylethylamine (24 ml; 200 mmol) and 1% of $H_2O$. The $Lact_{30}$, -GlcA-pLK polymer is precipitated and purified as previously described. The mean number of bound gluconoyle residues per molecule of conjugate is determined by measuring the a-amino groups of the lysine which remains on the polylysine by using the TNBS colorimetric method (Fields R., The measurement of amino groups in proteins and peptides. Biochem. J., 1971: 124: 581–90), is found equal to 30.

Biotinylation of the gluconoylated polylysine

The gluconoylated polylysine (containing 60 gluconoyle residues) is substituted by biotin: the polymer (20 mg; 0.33 mmol) dissolved in 0.5 ml of 0.1M sodium carbonate buffer, pH 9.0, containing 0.3M NaCl, is allowed to react for 20 h at 20° C. with 0.93 mg (1.7 mmol) of sulfosuccinimidyl-6-(biotinamido)hexanoate (NHS-LC-biotin, Pierce). The polymer is precipitated by adding 10 volumes of isopropanol. After centrifugation (1,800 g×15 min), the pellet is washed with isopropanol and collected upon another centrifugation. The pellet is dissolved in bidistilated water and the solution is lyophilized. The mean number of biotin fixed residues per molecule of polymer was determined by using the colorimetric method adapted from Green (Green N. M. A spectrophotomatic assay for avidin and biotin based on binding dyes by avidin. Biochem. J., 1965: 94: 23c–24c) by using 2-(4'-hydroxyazobenzene)benzoic acid (HABA) and streptavidin is found equal to 2.5.

Preparation of biotinylated neoglycoproteins

The BSA and the lactosylated BSA (Lact-BSA) (0.23 mmole) dissolved in 5 ml of 0.1M sodium carbonate buffer, pH 9.0, containing 0.3M NaCl is allowed to react for 20 h at 20° C. with NHS-LC-biotin (0.65 mg; 1.2 mmol). The conjugates are purified by filtration on Trisacryl GF05 gel (20x2 cm column) (Sepracor, Villeneuve la Garenne, France) in $H_2O$ containing 5% n-butanol, then lyophilisated. The mean number of linked biotin residues per molecule of protein is determined by using a colorimetric method with HABA, adapted from Green (Green N. M. A spectrophotomatic assay for avidin and biotin based on binding dyes by avidin. Biochem. J., 1965: 94: 23c–24c) and are found to be from 1 for BSA and 2 for Lact-BSA. The average molecular masses of BSA and Lact-BSA are 68,000 and 87,200, respectively.

Cells and cell cultures

HepG2 cells (human hepatocarcinoma, ATCC 8065 HB) which possess a membrane lectin recognizing glycoproteins terminated with $\beta$-D-galactose residues (Schwartz A. L., Fridovich S. E., Knowles B. B. and Lodish H. F. Characterization of the asialoglycoprotein receptor in a continuous hepatoma line. J. Biol. Chem., 1981: 256: 8878–81), the HEL cells (ATCC TIB 180) and K-562 (ATCC CCL 243) are cultivated respectively in DMEM medium (GIBCO, Reufrewshire, U. K.) and in RPMI 1640 medium supplemented with 10% heat-inactivated fetal bovine serum (GIBCO), 2 mM of L-glutamine (Merck), antibiotics (100 units/ml of penicillin and 100 mg/ml of streptomycin) Eurobio., Paris, France). The human macrophages derived from blood monocytes are prepared as described in Roche et al., 1985 (Roche A. C., Midoux P., Bouchard P. and Monsigny M. Membrane lectins on human monocytes: Maturation-dependent modulation of 6-phosphomannose and mannose receptors. FEBS Letters, 1985: 193: 63–68). 3LL cells are cultivated as described in Roche et al., 1983 (Roche A. C., Barzilay M., Midoux P., Junqua S., Sharon N., and Monsigny M. Sugar-specific endocytosis of glycoproteins by Lewis lung carcinoma cells. J. Cell. Biochem., 1983: 22: 131–40). The RBE4 cells given by P. O. Couraud (Hospital Cochin, Paris) were cultivated on collagen in a $\alpha$-MEM and $HamF_{10}$ medium 50/50, volume; volume) supplemented with 10% heat-inactivated fetal bovine serum, 2 mM of L-glutamine, antibiotics (100 units/ml of penicillin and 100 mg/ml of streptomycin) in the presence of TGFb.

The plasmids

The plasmid pSV2Luc (5.0 kb) was obtained from Dr. A. B. Brasier (Massachusetts General Hospital, Boston) (Brasier A. R., Tate J. E., and Habener J. F. Optimized use of the firefly luciferase assay as a reporter gene in mammalian cell lines. Biotechniques, 1989: 7: 1116–23). The plasmid CMVLuc was given by Dr. A. Dautry-Varsat (Institut Pasteur, Paris).

Formation of optimized plasmid/polylysine conjugate complexes

Only the complexes for which no migration of DNA is produced in electrophoresis on agarose gel, thus named optimized complexes of DNA/polymer, are used for the transfection of cells. The molar ratios between the polymer and the DNA necessary for forming optimized pSV2Luc plasmid/polymer complexes are determined by electrophoresis on agarose gel at 0.6%: the complexes are prepared by adding, drop by drop under constant mixing, variable quantities of polylysine conjugates in 60 ml of DMEM, to 2 mg (0.6 pmol) of pSV2Luc plasmid in 140 ml of DMEM. After incubation for 30 minutes at 20° C., 20 ml of each sample is analyzed by electrophoresis on 0.6% agarose gel (containing ethidium bromide for visualizing the DNA) in a Tris borate EDTA buffer (Tris 95 mM, boric acid 89 mM and EDTA 2.5 mM), pH 8.6.

Preparation of DNA/vector complexes

Complexes of pSV2Luc plasmid and polylysine conjugates

Optimized DNA/polymer complexes are prepared by adding, drop by drop under constant agitation, the polylysine or a conjugate of poly-L-lysine ($Lact_{60}pLK$, $GlcA_x$-PLK, $30<x<130$, with $Lact_{30}pLK$, or $Lact_{30}$-$GlcA_{30}$-pLK) in 0.6 ml of DMEM at 20 mg (6 pmol) of pSV2Luc plasmid in 1.4 ml of DMEM. The solution is maintained for 30 minutes at 20° C.

Complexes of pSV2Luc plasmid and pLK-streptavidine-neoglycoprotein

The optimized complexes of pSV2Luc plasmid/biotinylated polylysine are formed by adding, drop by drop under constant mixing, 10 mg (172 pmol) of gluconoylated and biotinylated polylysine (containing 60 gluconoyle residues) in 290 ml of DMEM to 10 mg (3 pmol) of pSV2Luc plasmid in 0.7 ml of DMEM (molecular ratio between the polymer and the DNA close to 57:1). The solution is maintained for 30 minutes at 20° C. The biotinylated neoglycoproteins (Lact-BSA and BSA) (377 pmol) in 0.5 ml of DMEM are then added, with constant stirring, to 1 ml of pSV2Luc plasmid/biotinylated polylysine complex, and then the streptavidin (27.5 mg; 490 pmol) in 0.5 ml of DMEM is added under agitation (molar ratio between the neoglycoprotein and the DNA close to 125:1) and the solution is maintained for 30 minutes at 20° C.

Gene transfer $5 \times 10^5$ HepG2 cells per well are seeded on day 0 on 12 well tissue culture plates, respectively. On day 1, after removing the medium, the solution (2 ml) containing the plasmid/conjugate complex of polylysine supplemented with 1% heat-inactivated bovine fetal serum, and with 100 µM in the chloroquine (Luthman H. and Magnusson G. High efficiently polyoma DNA transfection of chloroquine treated cells. Nucleic Acids Res., 1983: 11: 1295–1308), is added to the wells. After 4 hours of incubation at 37° C., the supernatant is removed and 2 ml of fresh DMEM complete medium is added and the cells are then further incubated for 48 h at 37° C.

Luciferase test

The genetic expression of the luciferase is measured by luminescence according to the method described by De Wet et al., 1987 (De Wet J. R., Wood K. V., De Luca M., Helinski D. R. and Subramani S. Firefly luciferase gene: structure and expression in mammalian cells. Mol. Cell. Biol. 1987: 7: 725–37). The culture medium is removed, and the cells are harvested upon incubation at 37° C. in PBS containing 0.2 mg/ml of EDTA and 2.5 mg/ml of trypsine (GIBCO) and washed 3 times with PBS. The homogenization buffer (200 ml; 8 mM $MgCl_2$, 1 mM of dithiothreitol, 1 mM of EDTA, 1% Triton X 100 and 15% glycerol, 25 mM of Tris-phosphate buffer pH 7.8), is added to the pellet. The suspension is agitated with a vortex and maintained for 10 min at 20° C., and then centrifuged (5 min, 800 g). ATP (95 ml of a 2 mM solution in the homogenization buffer without Triton X 100) is added to 60 ml of the supernatant and the luminescence is registered for 4 seconds by using a luminometer (Lumat LB 9501, Berthold, Wildbach, Germany) upon automatic addition of 150 ml of 167 mM luciferin in water; the measurements are made in triplicate.

Protein dosage

A protein dosage is made for each sample by using the bicinchoninic colorimetric acid method (BCA) (Smith P. K., Krohn R. I., Hermanson G. T., Mallia A. K., Gartner F. H., Provenzano M. D., Fujimoto E. K., Goeke N. M., Olson B. J. and Klenk D. C. Measurement of protein using bicinchoninic acid. Anal. Biochem., 1985: 150: 76–85), adapted by Hill and Straka (Hill H. D. and Straka J. G. Protein determination using bicinchoninic acid in the presence of sulf-hydryl reagents. Anal. Biochem., 1988: 170: 203–08) because of the presence of DTT in the homogenization buffer. The measure of the expression of luciferase is expressed as relative light units (RLU) per mg of BSA (free albumin of purified and crystallized fatty acid, A7511, Sigma), 1 mg BSA corresponding to $1.2 \times 10^6$ HepG2 cells.

Results

Gluconoylated polylysine

The poly-L-lysine (average molecular mass of the salt form 40.000; mean degree of polymerization 190) was partially (from 15 to 70%) acylated at the level of $e$-$NH_2$ function of the lysine by using D-gluconolactone, an agent which enhances the water solubility. The objective is to reduce the number of positive charges on the polylysine and consequently to reduce the electrostatic interactions between the polymer and a plasmid.

In the presence of polylysine, the DNA is strongly compacted by the cooperative interactions between the positive charges of the polylysine and the negative charges of the DNA.

Figure 1A:
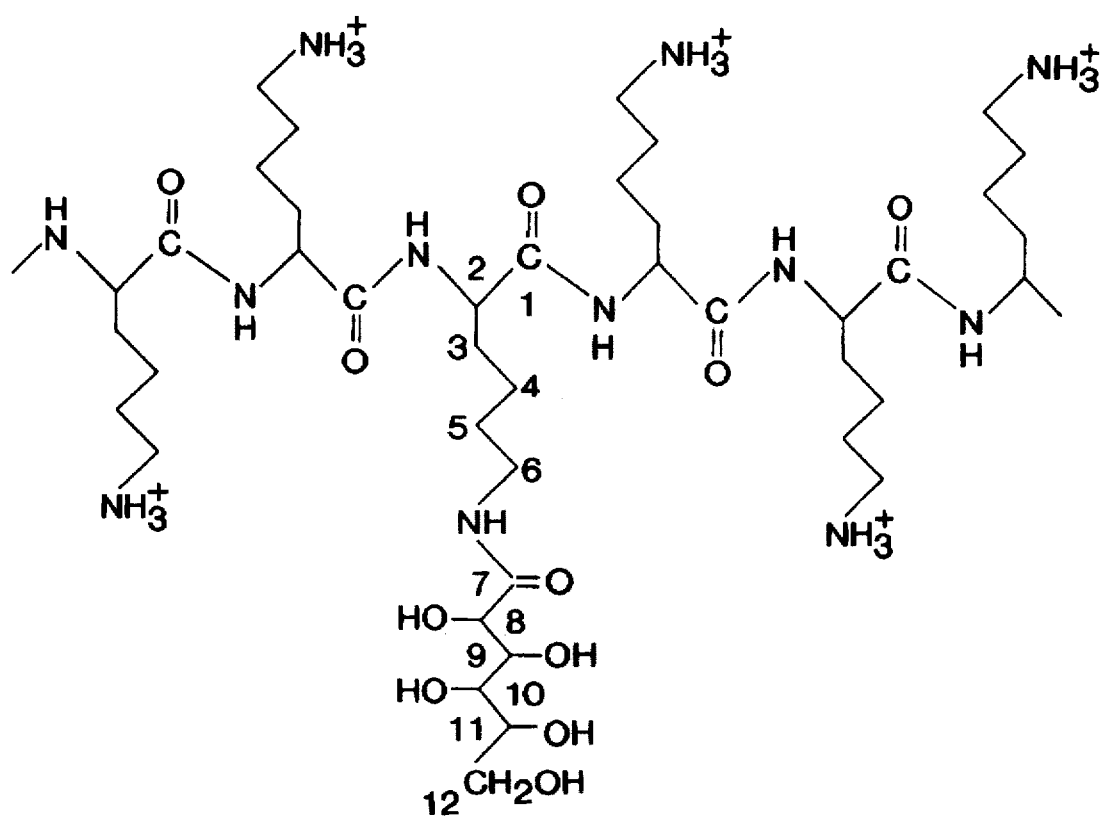
Figure 1B:
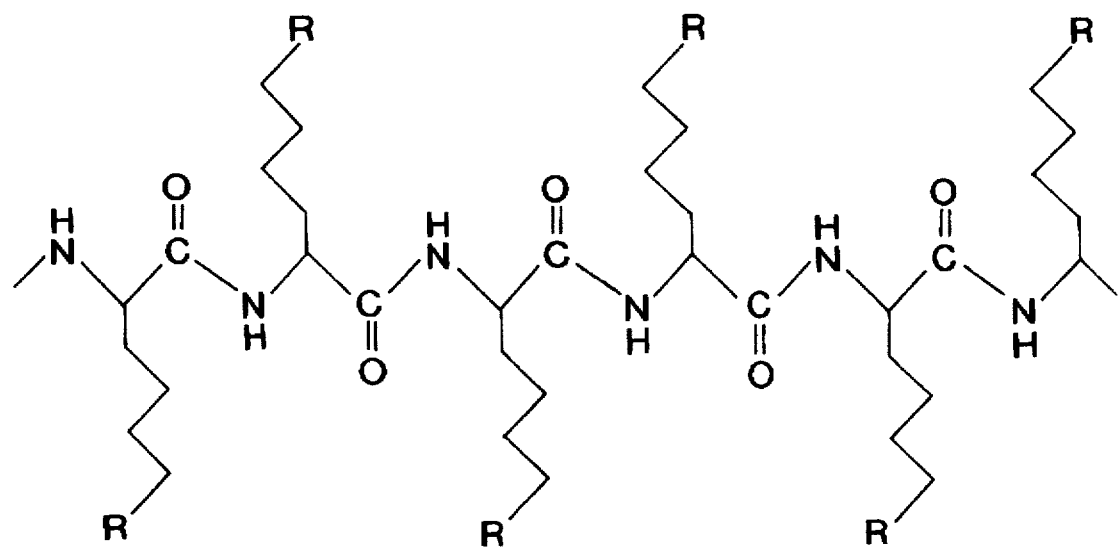
Figure 1C:
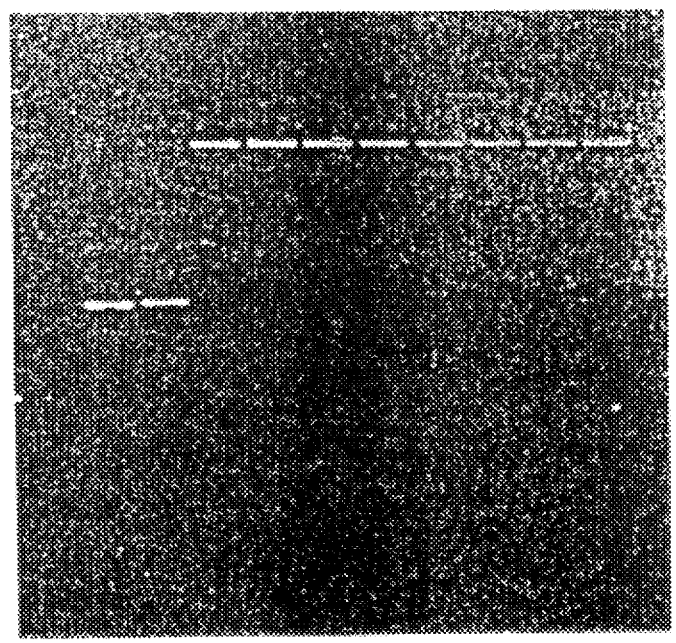

The formation of complexes between a plasmid of 5 kb, such as the pSV2Luc plasmid containing the gene of luciferase with polylysines substituted with increasing quantities of gluconoyle residues, is analyzed by electrophoresis on agarose gel, and the optimized DNA/polymer complexes corresponding to those for which the DNA does not migrate in electrophoresis following the total condensation of the DNA are also readily determined (FIG. 1c). Above 80% of substitution, the gluconoylated polylysine does not form any complex with DNA.

The amount of gluconoylated polylysine complexed with a DNA molecule was determined as a function of the molar ratio (P/DNA) between the gluconoylated polylysine and the DNA (FIG. 2c). When P/DNA is between 100 and 200, the amount of free gluconoylated polylysine is practically null; in other words, all the polylysine is complexed with the DNA. Consequently, there is no need to purify these complexes because there is no free polylysine (which is cytotoxic) to be removed. Moreover, the complexes with such ratios were very efficient in transfecting cells.

As shown in the results of FIGS. 2a and 2b, the increase in expression of the luciferase by the HepG2 cells (human hepatocarcinoma) is related to the increased number of gluconoyle residues fixed on the polylysine and reaching a maximum (approximately 300 times greater than with the plasmid alone) (base line) when the polylysine is substituted with 45 to 70% (88 to 132) gluconoyle residues by using the colorimetric assay (FIG. 2a) or 35 to 70% (70 to 132) gluconoyle residues by using NMR determination (FIG. 2b). The polylysines substituted by few or too many gluconoyle residues are not effective or slightly effective. As a comparison, the expression of the luciferase obtained under the same conditions using lactolysated polylysine under optimal conditions, allows one to conclude that the transfection obtained with the gluconoylated polylysine (substituted at 58%) is comparable to that obtained with the lactosylated polylysine under optimal conditions.

In the DNA/polymer complexes for which DNA did not migrate upon electrophoresis due to the total condensation of the DNA, the molar ratio between the amount of gluconoylated polylysine and DNA and the ratio between the number of positive charges and the number of negative charges increased linearly when the number of gluconoyle residues bound to polylysine increased (FIG. 2d). The complexes present an excess of negative charges when polylysine is weakly substituted and are globally neutral while the polylysine is substituted by half. In the best conditions of transfection (35 to 45% of substitution), the complexes are close to neutrality. This indicates that the polycationic character of the polylysine is not involved in the efficacy of the transfection. The neutral or anionic character of the DNA/gluconoylated polylysine complexes limiting the non-specific interactions with the cells is a supplementary advantage of their use in vivo.

Figure 7A:
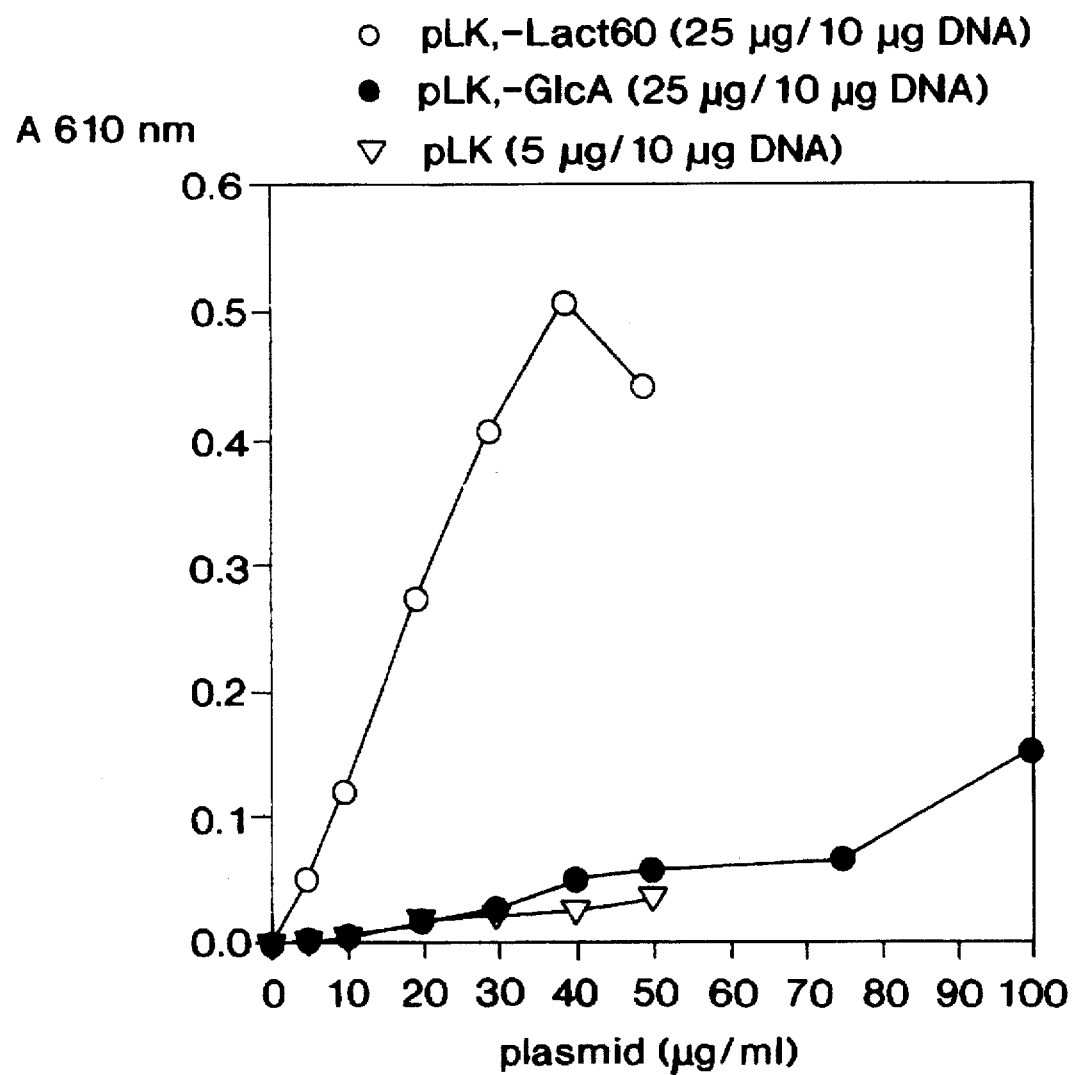

The polylysine substituted by 45 to 70% (88 to 132 residues) of gluconoyle residues allows the preparation of highly concentrated DNA/polymer complexes, up to 100 mg/ml of DNA, while with the lactolysated polylysine, it is only possible to prepare complexes 10 times less concentrated in DNA. FIG. 7 shows, in comparison, the solubility in relation to the concentration of DNA, and of DNA/polylysine, DNA/gluconoylated polylysine and DNA/lactolysated polylysine complexes. This study is monitored by measuring the turbidity (measure of the absorbance at 610 nm) of different solutions. The DNA/polylysine and DNA/gluconoylated polylysine complexes remain soluble up to more than 100 mg/ml, while with the lactolysated polylysine, the complexes precipitate starting from 20 mg/ml. In the presence of polymer, the DNA is strongly compacted as a result of a cooperative phenomenon between the positive and negative charges of the two polymers. In the case of the gluconoylated polylysine, approximately 60% of the positive charges being substituted, the electrostatic interactions between the DNA and the polymer are reduced; this facilitates a dissociation of the DNA/polymer complexes and particularly a release of the DNA in the cell allowing an effective expression of the gene. A study of the modification of the cooperation of electrostatic interactions between the DNA and the gluconoylated polylysine is conducted as a function of the ionic strength and the nature of the counterions.

Gluconoylated polylysine furnished with a recognition signal

The gluconoylated polylysine can be substituted by a ligand of low molecular mass such as lactose which has a medium range affinity for a membrane receptor or the biotin which has a very strong affinity for a membrane receptor.

Gluconoylated and lactolysated polylysine

When the polylysine is substituted with 30 lactose residues, the HepG2 cells are very weakly transfected compared to the results obtained with the polylysine substituted with 60 lactose residues (Table 1). The polylysine substitute with 30 lactoses possess more positive charges, interacting strongly with the DNA and impairing a rapid dissociation of the DNA from the complex. When the polylysine containing 30 lactose residues is also substituted with 30 gluconoyle residues, the expression of the luciferase is elevated and comparable to that obtained with the polylysine substituted with 60 lactose residues. The addition of gluconoyle residues permits a reduction of electrostatic interactions between the DNA and the polylysine, facilitating a rapid dissociation of the DNA in the cell.

Figure 7B:
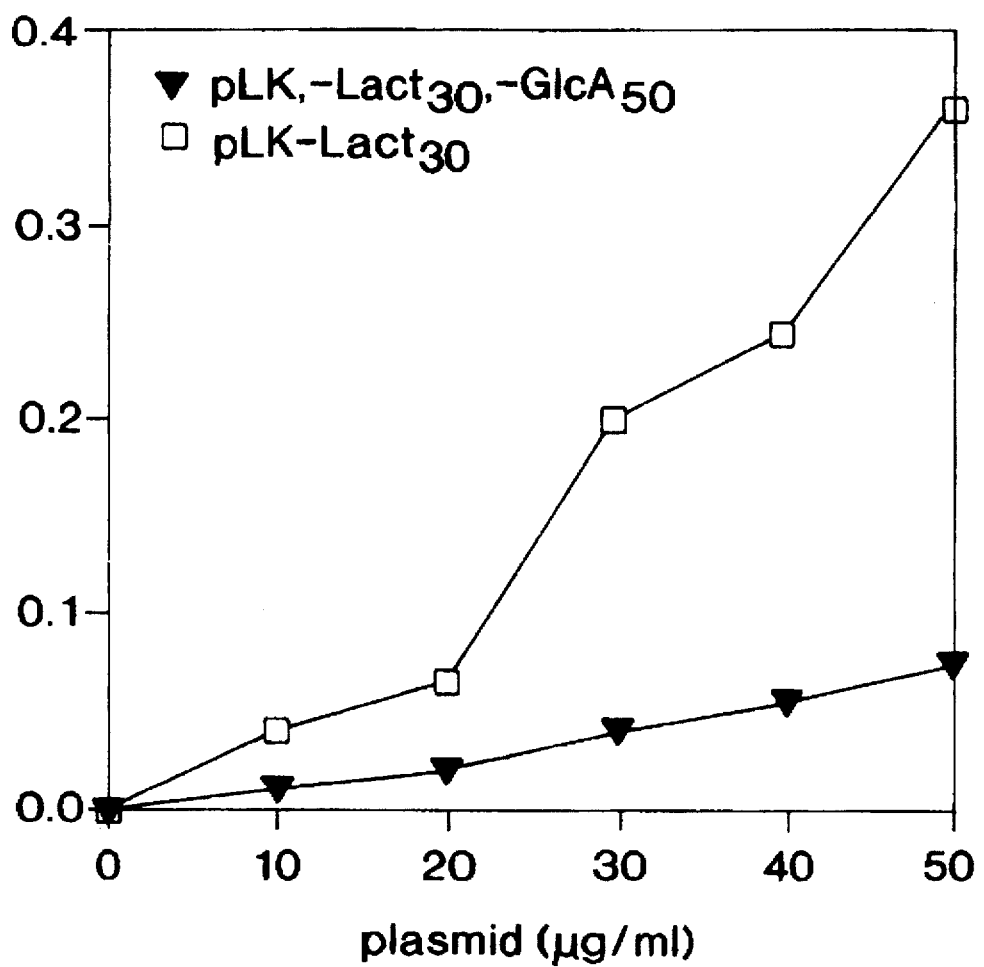

In addition, as shown in FIG. 7b, the substitution of polylysine with both lactose residues and gluconoyle residues increased the solubility of the complexes related to that of lactosylated polylysine and allows the preparation of concentrated complexes up to 100 µg/ml usable in vivo.

Gluconoylated and biotinylated polylysine

When the gluconoylated polylysine (containing 60 gluconoyle residues) is substituted by a small number (2.5) of biotin residues, the DNA/biotinylated polylysine complexes have a very strong affinity $10^{15}$ l/mole) for the streptavidine. If in addition the streptavidine is furnished with a recognition signal recognized by a membrane receptor specific to a cell type which induces the endocytosis of the complexes, the DNA thus acquires a cellular specificity. This is shown in Table II: the plasmid complexed with gluconoylated and biotinylated polylysine to the streptavidine associated with a recognition signal such as lactolysated serum albumin which is recognized by and taken up via the membrane lectin of HepG2 cells, the expression of the luciferase is much greater than when the albumin serum is lacking lactose or when the streptavidine is lacking a recognition signal.

Gene transfer by DNA/cytokine complexes

Figure 8:
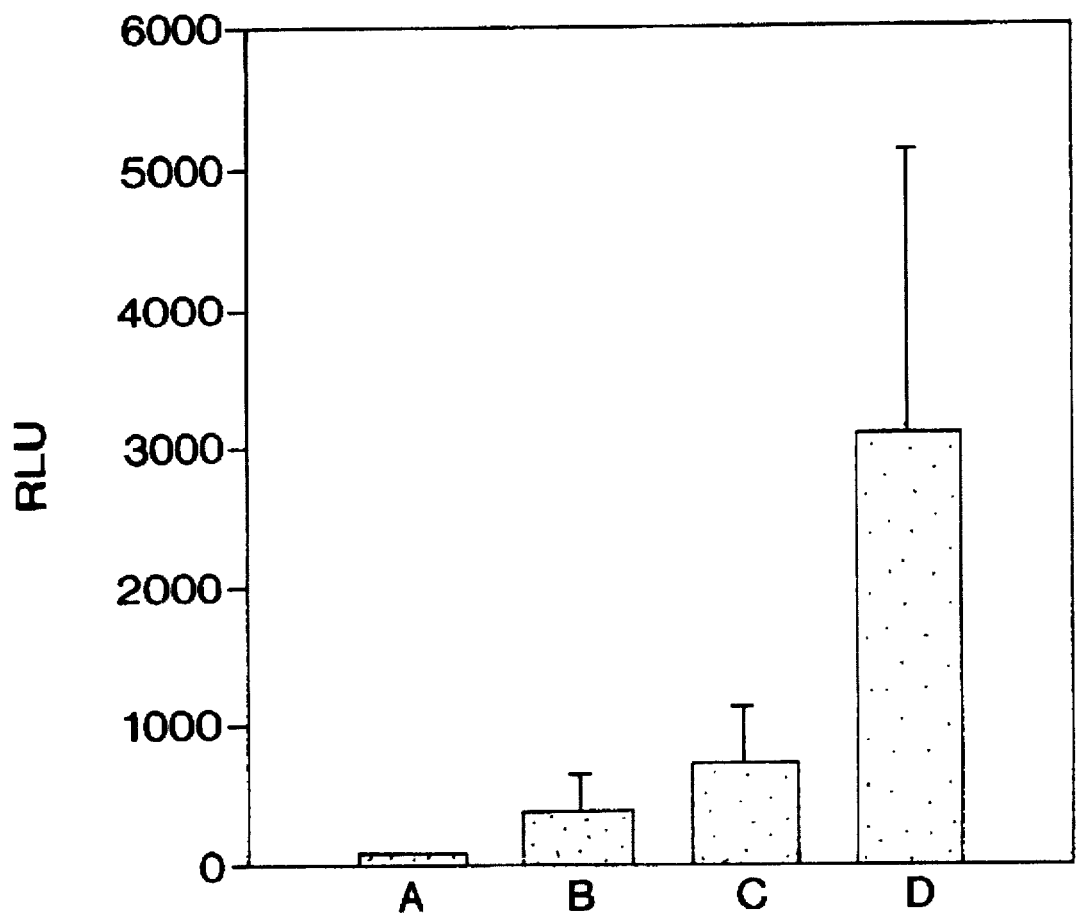
Figure 9:
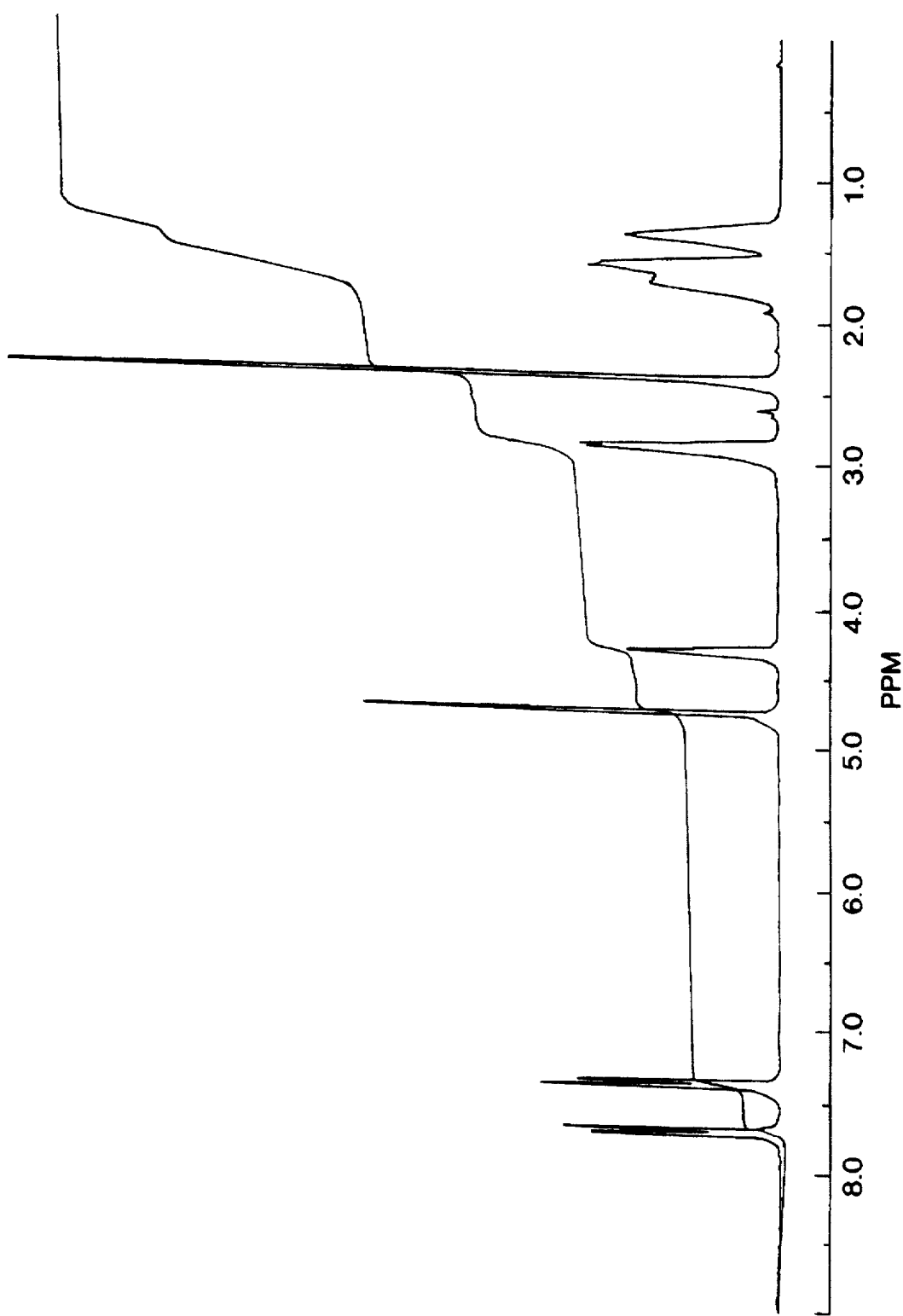
Figure 10:
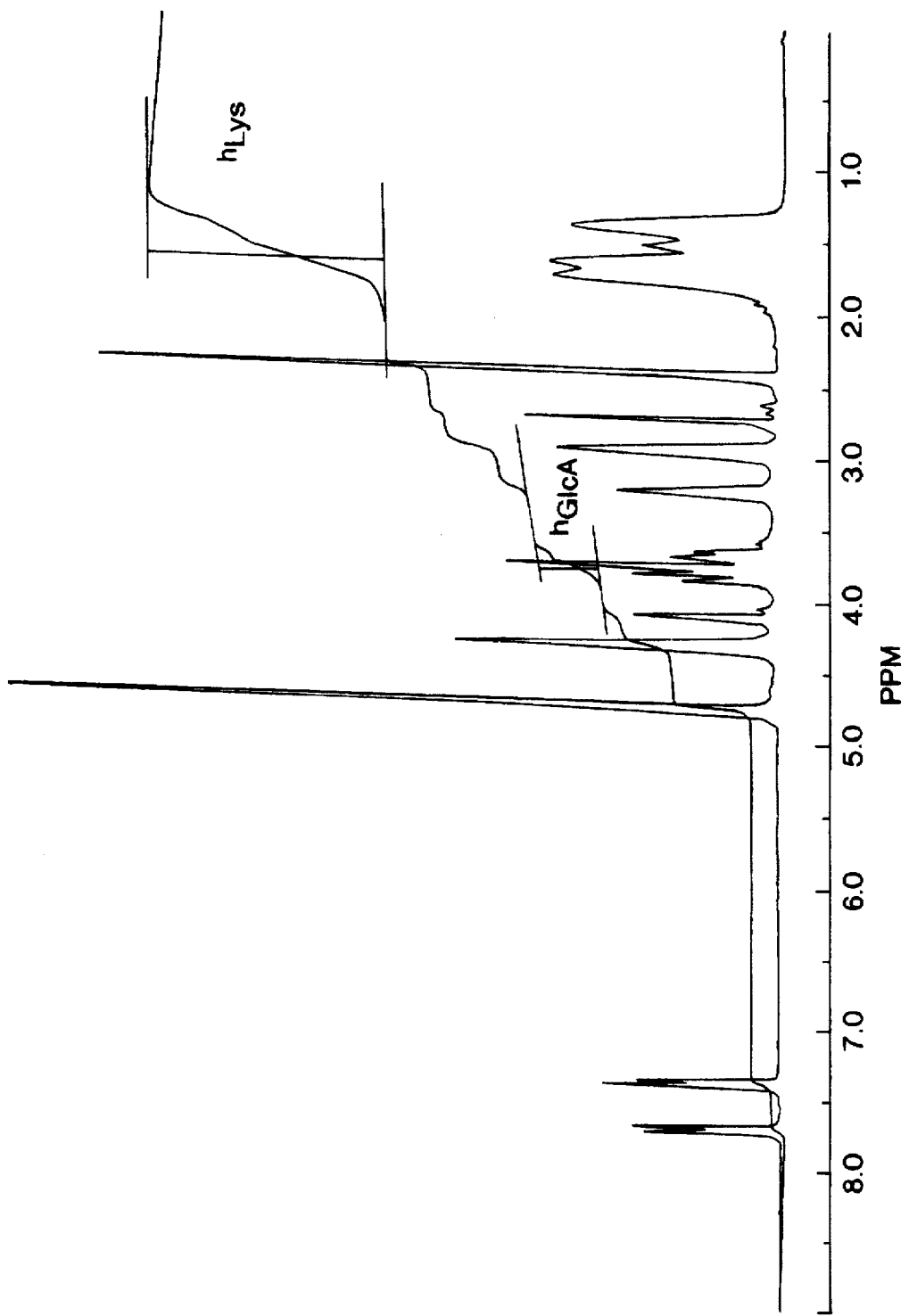

Gene transfer in myeloid cell lines by complexes with polylysine substituted with the Stem Factor (SCF) was represented in FIG. 8. A plasmid containing the luciferase gene was complexed with a gluconoylated and biotinylated polylysine and with a biotinylated SCF by using streptavidin. The complexes thus formed were efficient for transfecting HEL cells which expressed SCF receptors (c-kit).

Gluconoylated polylysine and gene transfer in various cell types

Figure 4:
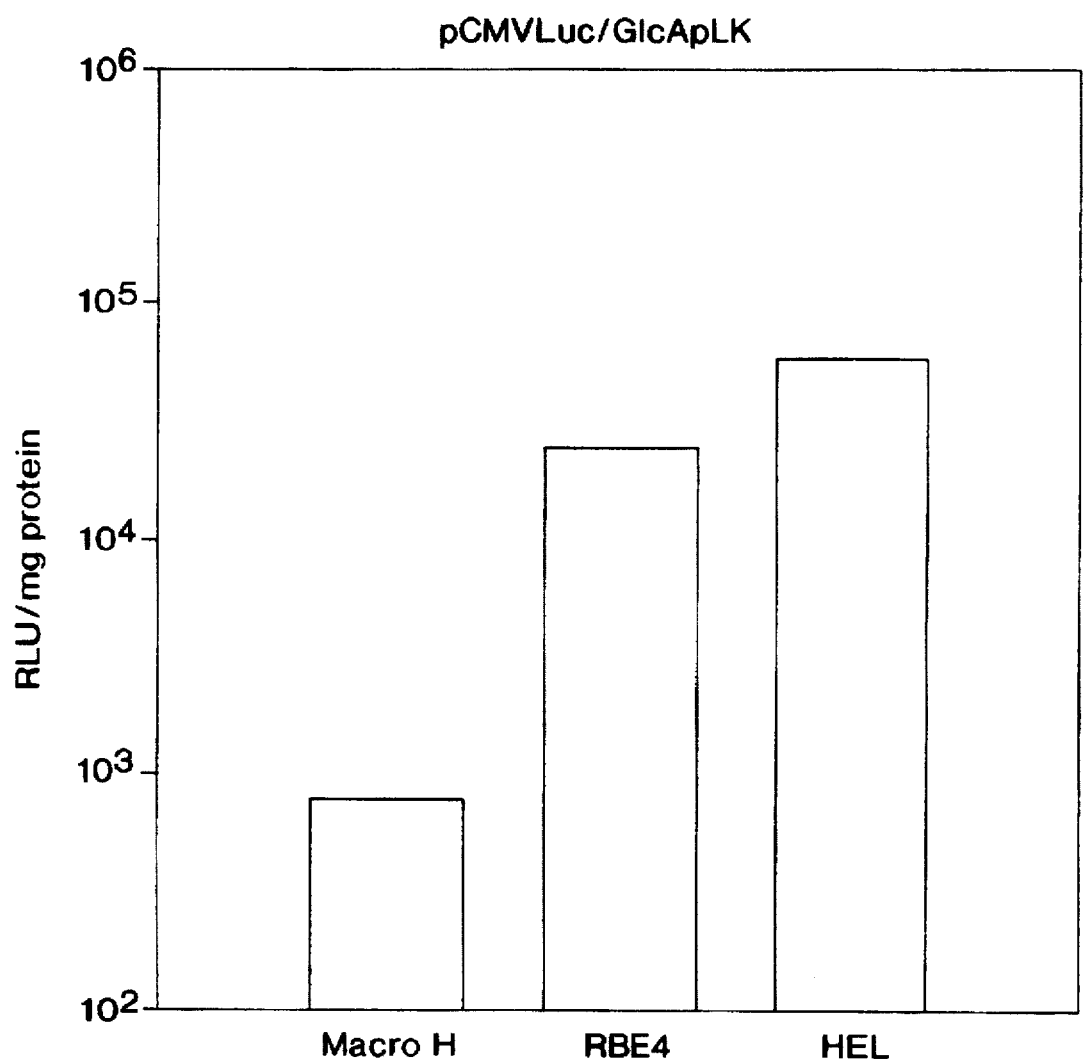
Figure 5:
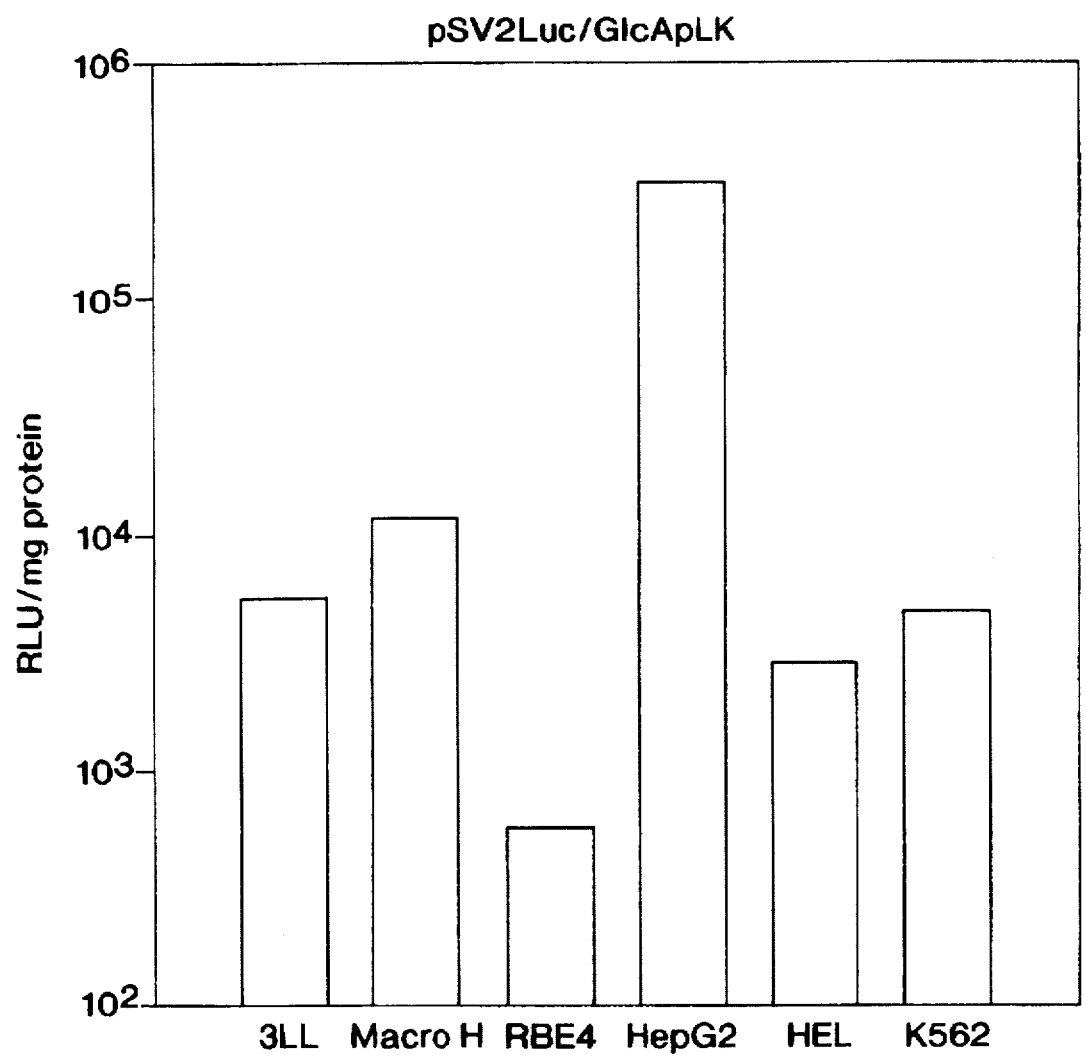
Figure 6:
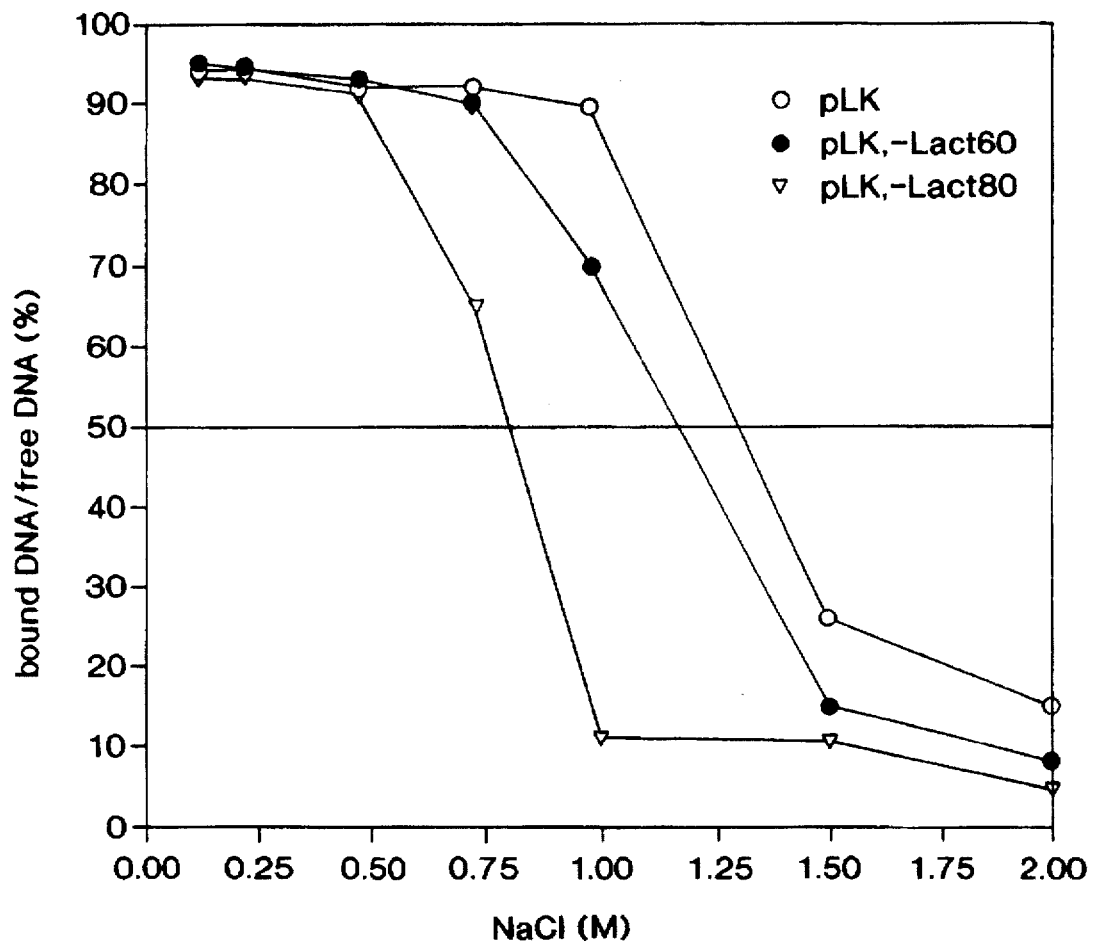

The polylysine substituted with 45 to 70% of gluconoyle residues permits with good efficacy the transfection of adhering cells, such as human macrophages, human hepatocarcinoma, rat endothelial cells, and also of non-adhering cells, such as human T lymphoma and leukemic cells of the erythroid lineage (FIGS. 4 and 5).

Conclusions

The inventive nature of the gluconoylated polylysine lies in:

the use of a partially substituted polylysine for the reduction of electrostatic interactions between the DNA and the polycationic polymer in order to facilitate the intracellular release of the DNA upon internalization in the cell by a phenomenon of non-specific endocytosis (the presence of membrane receptors capable of specifically recognizing the gluconoyle residues is not known);

the gluconoyle residues act also as hydrosolubilizers and permit the preparation of DNA/polylysine complexes which are highly concentrated and thus better suitable to be used in vivo, which is not the case with the lactolysated polylysine or the polylysine substituted by proteins such as transferrin or asialoorosomucoid;

the gluconoylated polylysine can be utilized for transfecting various cell types and in particular non-adherent cells;

the gluconoylated polylysine can be used as a basis polymer to confer a cellular specificity to the DNA by the addition of ligand molecules of low molecular mass recognized by specific membrane receptors. The advantage of the gluconoylated polylysine in relation to the non-gluconoylated polylysine is that the former is already optimized for permitting the formation of DNA/polymer-ligand complexes which are easily dissociated in the cell which reduces the number of ligand molecules to be fixed on the polylysine. In fact, it has already been shown that the efficacy of transfection depends on the number of molecules of sugars fixed on the non-gluconoylated polylysine (60 lactose residues or 80 galactose residues are necessary for an optimal transfection in the cells possessing a receptor recognizing lactose or galactose).

Gluconoylated polylysine bearing a recognition signal

1°) Osides a) Galactoside

Preparation of galactosylated and gluconoylated polylysine

Polylysine bearing an average number of 50 gluconoyl residues per pLK molecule (50 mg; 0.91 µmol) dissolved in 2 ml of dimethylsulfoxide was stirred with 4-isothiocyanatophenyl β-D-galactopyranoside (8.5 mg; 27 µmol) in the presence of diisopropylethylamine (22 µl; 150 µmol) for 24 h at 20° C. as described (Midoux et al 1993 Specific gene transfer mediated by lactosylated poly-L-lysine into hepatoma cells. Nucleic Acids Res., Vol. 21, p. 871–878). The polymer was precipitated by adding 10 volumes of isopropanol and spun down by centrifugation (1 800 g for 15 min). The pellet was washed with isopropanol, collected by centrifugation (1 800 g for 15 min), solubilized in distilled water and freeze-dried. The average number of galactose residues bound per polymer molecule was determined by a resorcinol sulfuric acid micromethod (Monsigny et al 1988 Colorimetric determination of neutral sugars by a resorcinol sulfuric acid micromethod. Anal. Biochem., Vol. 175, pp. 525–530). The average number of galactose residues was 20 ($Gal_{20}$-$GlcA_{50}$-pLK).

b) mannoside

Preparation of mannosylated and gluconoylated polylysine:

Polylysine bearing an average number of 50 gluconoyl residues per pLK molecule (50 mg; 0.91 µmol) dissolved in 2 ml of dimethylsulfoxide was stirred with 4-isothiocyanatophenyl-α-D-mannopyranoside (8.5 mg; 27 µmol) in the presence of diisopropylethylamine (22 µl; 150 µmol) for 24 h at 20° C. as described (Midoux et al, 1993 Specific gene transfer mediated by lactosylated poly-L-lysine into hepatoma cells. Nucleic Acids Res., Vol. 21, pp. 871–878). The polymer was precipitated by adding 10 volumes of isopropanol and spun down by centrifugation (1 800 g for 15 min). The pellet was washed with isopropanol, collected by centrifugation (1 800 g for 15 min), solubilized in distilled water and freeze-dried. The average number of mannose residues bound per polymer molecule was determined by a resorcinol sulfuric acid micromethod (Monsigny et al 1988 Colorimetric determination of neutral sugars by a resorcinol sulfuric acid micromethod. Anal. Biochem., Vol. 175, pp. 525–530). The average number of mannose residues was 18 ($Man_{18}$-,$GlcA_{50}$-pLK).

c) fucoside

Preparation of fucosylated and gluconoylated polylysine:

Polylysine bearing an average number of 50 gluconoyl residues per pLK molecule (50 mg; 0.91 µmol) dissolved in 2 ml of dimethylsulfoxide was stirred with 4-isothiocyanatophenyl-α-I-fucopyranoside (8 mg; 27 µmol) in the presence of diisopropylethylamine (22 µl; 150 µmol) for 24 h at 20° C. as described (Midoux et al 1993 Specific gene transfer mediated by lactosylated poly-L-lysine into hepatoma cells. Nucleic Acids Res. Vol. 21, pp. 871–878). The polymer was precipitated by adding 10 volumes of isopropanol and spun down by centrifugation (1800 g for 15 min). The pellet was washed with isopropanol, collected by centrifugation (1800 g for 15 min), solubilized in distilled water and freeze-dried. The average number of mannose residues bound per polymer molecule was determined by a resorcinol sulfuric acid (Monsigny et micromethod (Monsigny et al 1988 Colorimetric determination of neutral sugars by a resorcinol sulfuric acid micromethod. Anal. Biochem., Vol. 175, pp. 525–530). The average number of fucose residues was 21 ($Fuc_{21}$-$GlcA_{50}$-pLK).

Gene transfer into human blood monocytes-derived macrophages (FIG. 11)

Peripheral blood mononuclear cells (PBMC) isolated from peripheral blood were maturated by culture for 12 days in the presence of Granulocytes and Macrophages Colonies Stimulating Factor. GM-CSF (100 U/ml) as described (Erbacher et al 1966 Gene transfer by DNA/glucosylated polylysine complexes into human blood monocyte-derived macrophages. Hum. Gene Ther., Vol. 7, pp. 721–729). Macrophages ($3 \times 10^5$) were incubated at 37° C. in 1 ml of DMEM containing 1% FBS, 100 µM chloroquine and DNA (a mixture of 3 µg $pLTR_{HIV}$LUC and 2 µg $pLTR_{HIV}$TAT) complexed with either pLK (2.5 µg), gluconoylated pLK ($GlcA_{50}$pLK) (10 µg) or mannosylated and gluconoylated polylysine ($Man_{18}$-$GlcA_{50}$pLK) (12.5 µg). The DNA/polymer complexes were formed with the lowest polymer to DNA molar ratio inducing a complete retardation of all the DNA in electrophoresis as described (Erbacher et al 1995 Glycosylated polylysine/DNA complexes: gene transfer efficiency in relation with the size and the sugar substitution level of glycosylated polylysines and with the plasmid size. Bioconjugate Chem., Vol 6, 401–410). After 4 hours of incubation, the medium was removed and the cells were incubated in 2 ml RPMI 1640 containing 5% FBS in the absence of any other additive. The gene expression was determined 24 hours later by measuring the luciferase activity in cell lysates. RLU, the number of relative light units, represents the luciferase activity in 106 viable cells and each data was the mean±SD (standard deviation) of 3 replicates of three or more separated macrophage preparations.

Gene transfer into human blood monocytes-derived macrophages (FIG. 12)

Peripheral blood mononuclear cells (PBMC) isolated from peripheral blood were maturated by culture for 12 days in the presence of Granulocytes and Macrophages Colonies Stimulating Factor. GM-CSF (100 U/ml) as described (Erbacher et al 1996 Gene transfer by DNA/glycosylated polylysine complexes into human blood monocyte-derived macrophages. Hum. Gene Ther., Vol 7, pp. 721–729). Macrophages ($3 \times 10^5$) were incubated at 37° C. in 1 ml DMEM containing 1% FBS. 100 µM chloroquine and DNA (a mixture of 3 µg $pLTR_{HIV}$LUC and 2 µg $pLTR_{HIV}$TAT) complexed with either pLK (2.5 µg), gluconoylated pLK ($GlcA_{50}$pLK) (10 µg) or fucosylated and gluconoylated polylysine ($Fuc_{21}$-$GlcA_{50}$-pLK) (12.5 µg). The DNA/polymer complexes were formed with the lowest polymer to DNA molar ratio inducing a complete retardation of all the DNA in electrophoresis as described (Erbacher et al 1995 Glycosylated polylysine/DNA complexes: gene transfer efficiency in relation with the size and the sugar substitution level of glycosylated polylysines and with the plasmid size. Bioconjugate Chem., Vol. 6, 401–410). After 4 hours of incubation, the medium was removed and the cells were incubated in 2 ml RPMI 1640 containing 5% FBS in the absence of any other additive. The gene expression was determined 24 hours later by measuring the luciferase activity in cell lysates. RLU, the number of relative light units, represents the luciferase activity in $10^6$ viable cells and each data was the mean±SD (standard deviation) of 3 replicates of three or more separated macrophage preparations.

2.) Complex saccharides (oligosides)

Preparation of gluconoylated polylysine substituted with complex oligosides

I. Lewis$^x$ Fucα3(Galβ4)GlcNAcβ3Galβ4Glc

Complex oligosaccharides with a glucose (Glc) or N-acetyl glucosamine (GlcNAc) residue in a terminal reducing position are transformed into glycopeptides according to a procedure described in the patent application: Monsigny et al 1966. Nouveaux derives d'oligosides, leur procede de preparation et leurs applications. novel oligosaccharide derivatives, preparation method therefor and uses thereof. (U.S. patent application Ser. No. 08/591,481. Alternatively, glycopeptides may be obtained by proteinase digestion and derivatized into para-nitrophenyl glycopeptides, according to known procedures such as the one described in Kieda et al 1977. Preparation and properties of glycosylated cytochemical markers. FEBS LETTERS, Vol. 76: 257–261.

Glycopeptides are then bound to partially gluconoylated polylysine according to several known procedures and preferably by using one of the following recipes:

a) Linkage of glycopeptides to partially gluconoylated polylysine through a disulfide bridge preparation of gluconoylated polylysine substituted with dithiopyridine groups Polylysine bearing an average number of 60 gluconoyl residues per pLK molecule (50 mg; 0.91 µmol) dissolved in 2 ml of dimethylsulfoxide was stirred for 12 hours at 20° C. with 4-succinimidyloxycarbonyl-α-(2-pyridinyldithio)-toluene (SMPT, Pierce, USA) (5.3 mg; 13.6 µmol). The polymer (MPT-GlcA$_{60}$-pLK) was precipitated by adding 10 volumes of isopropanol and spun down by centrifugation (1800 g for 15 min). The pellet was washed with isopropanol, collected by centrifugation (1800 g for 15 min), solubilized in distilled water and freeze-dried. The average number of MPT residues bound per polymer molecule was determined from the absorbance at 343 nm (c=8080M$^{-1}$×cm$^{-1}$) of pyridine thione released after reaction with tris (carboxyethyl)phosphine (TCEP). The average number of MPT residues was 10. (MPT$_{10}$-GlcA$_{60}$-pLK)

preparation of gluconoylated polylysine substituted with glycopeptides

The complex saccharide Lewis$^x$=Fucα3(Galβ4)GlcNAcβ3Galβ4Glc was linked on the amino group of glutamic acid derivative such as the glutamyl-amido-ethyldithiopyridine $CO_2H-CH_2CH_2(NH_2)$ CHCONHCH$_2$CH$_2$-SS-pyridine, leading to the glycopeptide: Fucα3(Galβ4)-GlcNAcβ3Galβ4Glcβ-pyroglutamyl-amido-ethyldithio-pyridine according to the procedure described in the above patent application and in a paper by Quetard et al, Simple synthesis of novel glycosynthons for glycoconjugate preparation: oligosylpyroglutamyl derivatives, in preparation.

reduction of the glycopeptide—Fucα3(Galβ4) GlcNAcβ3Galβ4Glcβ-pyroglutamyl-amidoethyldithiopyridine and its linkage to partially gluconoylated polylysine The glycopeptide Fucα3(Galβ4)GlcNAcβ3Galβ4Glcβ-pyroglutamyl-amidoethyldithiopyridine (0.2 µmol) was reduced with 0.2 µmol of TCEP in 1 ml of a 0.1M sodium phosphate buffer, pH 7.0 for 1 hour at 20° C. This solution was directly added to a solution of partially gluconoylated polylysine (0.02 µmol) substituted with pyridyldithiopropanoyle motifs. After 1 hour at 20° C., the polymer was precipitated by adding 10 volumes of isopropanol. The precipitate was collected after centrifugation (1800 g, 15 min) and washed with isopropanol, dissolved in distillated water and freeze-dried. The yield of this coupling step was equal to or better than 90%. The average number of Lewis$^x$ motifs bound per polymer molecule was determined by a resorcinol sulfuric acid micromethod (Monsigny et al, 1988 Colorimetric determination of neutral sugars by a resorcinol sulfuric acid micromethod. Anal. Biochem., Vol. 175, pp. 525–530). The average number of Lewis$^x$ motifs was 9 (Lewis$^x_9$-GlcA$_{60}$-pLK).

b) Linkage of glycopeptides to partially gluconoylated polylysine through a thiourea link.

The complex saccharide Lewis$^x$=Fucα3(Galβ4) GlcNAcβ3Galβ4Glc was linked to the amino group of glutamic acid derivative such as the glutamyl para-nitroanilide $CO_2H-CH_2CH_2(NH_2)CHCONHC_6H_4NO_2$, leading to the glycopeptide: Fucα3(Galβ4) GlcNAcβ3Galβ4Glcβ-pyrogutamyl-paranitroanilide according to the procedure described in the above patent application and in Quetard et al, Simple synthesis of novel glucosynthons for glycoconjugate preparation: oligosylpyroglutamyl derivatives, in preparation.

The glycopeptide oligosyl-pyroglutamyl-para-nitroanilide was reduced in a p-amino-anilide then was activated in a para-isothiocyanato-anilideGalβ4(Fucα3) GlcNAcβ3Galβ4Glcβ-pyroglutamyl-NH-p-C$_6$H$_4$-NCS according to a known procedure such as the one described by Roche et al, 1983 Endocytosis of glycoconjugates by Lewis lung carcinoma cells. J. Cell Biochem. Vol. 22, pp. 131–140 and Monsigny et al, 1984 Uptake of neoglycoproteins via membrane lectin(s) of L1210 cells evidenced by quantitative flow cytofluorometry and drug targeting. Biol. Cell Vol. 51, pp. 187–196.

Polylysine (0.9 µmol)—bearing an average number of 60 gluconoyl residues per pLK molecule—dissolved in 2 ml of dimethylsulfoxide was stirred with the oligosidyl-para-isothiocyanato-anilide (12 µmol) in the presence of diisopropylethylamine (22 µl; 150 µmol) for 24 hours at 20° C. as described (Midoux et al, Specific gene transfer mediated by lactosylated poly-L-lysine into hepatoma cells. Nucleic Acids Res., Vol. 21, pp. 871–878). The polymer was precipitated by adding 10 volumes of isopropanol and spun down by centrifugation 1,800 for 15 min). The pellet was washed with isopropanol, collected by centrifugation (1,800 for 15 min), solubilized in distilled water and freeze-dried. The average number of Lewis$^x$ motifs bound per polymer molecule was determined by a resorcinol sulfuric acid micromethod (Monsigny et al, 1988 Colorimetric determination of neutral sugars by a resorcinol sulfuric acid micromethod. Anal. Biochem. Vol. 175, pp. 525–530). The average number of Lewis$^x$ motifs was 8 (Lewis$^x_8$-GlcA$_{60}$-pLK).

II. Lewis$^b$=Fucα4(Fucα2Galβ3)GlcNAcβ3Galβ4Glc a) Linkage of glycopeptides to partially gluconoylated polylysine through a disulfide bridge preparation of gluconoylated polylysine substituted with glycopeptides The complex saccharide Lewis$^b$=Fucα4( Fucα2Galβ3)-GlcNAcβ3Galβ4Glc was linked to the amino group of glutamic acid derivative such as the glutamyl-amido-ethyldithiopyridine $CO_2H-CH_2CH_2(NH_2)$ CHCONHCH$_2$CH$_2$-SS-pyridine leading to the glycopeptide: Fucα4(Fucα2Galβ3) GlcNAcβ3Galβ4Glcβ-pyroglutamyl-amido-ethyldithiopyridine according to the procedure described in the above patent application.

reduction of the glycopeptide: Fucα4(Fucα2Galβ3)-GlcNAcβ3Galβ4Glcβ-pyroglutamyl-amidoethyldithiopyridine and its linkage to partially gluconoylated polylysine The glycopeptide Fucα4(Fucα2Galβ3)GlcNAcβ3Galβ4Glcβ-pyroglutamyl-amido-ethyldithiopyridine (0.2 μmol) was reduced with 1 μmol of TCEP in 1 ml of a 0.1M sodium phosphate buffer, pH 7.0 for 1 hour at 20° C. This solution was directly added to a solution of partially gluconoylated polylysine (0.02 μmol) substituted with pyridyldithiopropanoyle motifs. After 1 hour at 20° C., the polymer was precipitated upon adding 10 volumes of isopropanol. The precipitate was collected after centrifugation (1,800 g, 15 min) and washed with isopropanol, dissolved in distilled water and freeze-dried. The yield of this coupling step was equal to or better than 90%. The average number of Lewis$^x$ motifs bound per polymer molecule was determined by a resorcinol sulfuric acid micromethod (Monsigny et al, 1988 Colorimetric determination of neutral sugars by a resorcinol sulfuric acid micromethod. Anal. Biochem., Vol. 175, pp. 525–530). The average number of Lewis$^b$ motifs was 9 (Lewis$^x_9$-GlcA$_{60}$-pLK).

b) Linkage of glycopeptides to partially gluconoylated polylysine through a thiourea link.

The complex saccharide Fucα4(Fucα2Galβ3)GlcNAcβ3Galβ4Glc was linked to the amino group of glutamic acid derivative such as the glutamyl-para-nitroanilide $CO_2H—CH_2CH_2(NH_2)CHCONHC_6H_4NO_2$, leading to the glycopeptide: Fucα4(Fucα2Galβ3)GlcNAcβ3Galβ4Glcβ-pyroglutamyl-para-nitroanilide according to the procedure described in the above patent application.

The glycopeptide oligosyl-pyroglutamyl-para-nitroanilide was reduced in a p-amino-anilide and then was activated in a para-isothiocyanato-anilide Fucα4(Fucα2Galβ3)GlcNAcβ3Galβ4Glcβ-pyroglutamyl-NH-p-C$_6$—H$_4$-NCS according to a known procedure such as described by Roche et al, 1983 Endocytosis of glycoconjugates by Lewis lung carcinoma cells. J. Cell. Biochem. Vol. 22, pp. 131–140 and Monsigny et al, 1984 Uptake of neoglycoproteins via membrane lectin(s) of L1210 cells evidenced by quantitative flow cytofluorometry and drug targeting. Biol. Cell., Vol. 51, pp. 187–196.

Polylysine bearing an average number of 60 gluconoyl residues per pLK molecule (0.9 μmol) dissolved in 2 ml of dimethylsulfoxide was stirred with the oligosidyl-para-isothiocyanato-anilide (12 μmol) in the presence of diisopropylethylamine (22 μl; 150 μmol) for 24 hours at 20° C. as described (Midoux et al, 1993 Specific gene transfer mediated by lactosylated poly-L-lysine into hepatoma cells. Nucleic Acids Res., Vol. 21, pp. 871–878). The polymer was precipitated by adding 10 volumes of isopropanol and spun down by centrifugation (1,800 g for 15 min). The pellet was washed with isopropanol, collected by centrifugation (1,800 g for 15 min), solubilized in distilled water and freeze-dried. The average number of Lewis$^b$ motifs bound per polymer molecule was determined by a resorcinol sulfuric acid micromethod (Monsigny, et al, 1988 Colorimetric determination of neutral sugars by a resorcinol sulfuric acid micromethod. Anal. Biochem., Vol. 175, pp. 525–530). The average number of Lewis$^b$ motifs was 8 (Lewis$^b_8$-GlcA$_{60}$-pLK).

III. Oligomannosides

Oligomannosides containing between 5 to 9 mannosyle residues are recognized with a high affinity by various membrane lectins, especially those present on the surface of cells such as monocyte derived macrophages, histiocyles or dendritic cells (Avrameas et al, 1996 Expression of a mannose/fucose-specific membrane lectin on human dendritic cells. Eur. J. Immunol., Vol 26, pp. 394–400).

a) Linkage of oligomannosides to partially gluconoylated polylysine through a disulfide bridge The oligomannoside containing 8 mannoses and two N-acetyl-glucosamines Manα2Manα6(Manα3)Manα6(Manα2Manα2Manα3)-Manβ1GlcNAcβ4GLcNAc was linked to the amino group of glutamic acid derivative such as the glutamyl-amido-ethyldithiopyridine $CO_2H—CH_2CH_2(NH_2)CHCONHCH_2CH_2$-SS-pyridine, leading to the glycopeptide: Manα2Manα6(Manα3)Manα6(Manα2Manα2Manα3)Manβ-4GlcNAcβ-4GlcNAcβ-pyroglutamyl-amido-ethyldithiopyridine according to the procedure described in the above patent application: The oligosylpyroglutamyl amido-ethyldithiopyridine was then linked to a partially gluconoylated polylysine containing in average 190 lysyl residues and 60 gluconoyle residues under the conditions described to prepare the gluconoylated polylysine substituted with Lewis$^x$ oligosaccharides. The average number of oligomannoside motifs bound per polymer molecule was determined by a resorcinol sulfuric acid micromethod (Monsigny et al, 1988 Colorimetric determination of neutral sugars by a resorcinol sulfuric acid micromethod. Anal. Biochem., Vol. 175, pp. 525–530). The average number of oligomannoside motifs was 4.2 (oligomannoside$_{4.2}$-GlcA$_{60}$-pLK).

b) Linkage of oligomannoside motifs to partially gluconoylated polylysine through a thiourea link.

An oligomannoside containing 8 mannoses and two N-acetyl-glucosamines Manα2Manα6(Manα3)Manα6(Manα2Manα2Manα3)Manβ-4GlcNAcβ4GlcNAc was linked to the amino group of glutamic acid derivative such as glutamyl-para-nitroanilide $CO_2H—CH_2CH_2(NH_2)CHCONHC_6H_4NO_2$, leading to the glycopeptide: Manα2Manα6(Manα3)Manα6(Manα2Manα2Manα3)Manβ-4GlcNAcβ-4GlcNAcβ-pyrogutamyl-para-nitroanilide according to the procedure described in the above patent application. The oligosyl-pyroglutamyl-para-nitroanilide was then linked to a partially gluconoylated polylysine containing in average 190 lysyl residues and 60 gluconoyle residues under the conditions described to prepare the gluconoylated polylysine substituted with Lewis$^x$ oligosaccharides. The average number of oligomannoside motifs bound per polymer molecule was determined by a resorcinol sulfuric acid micromethod (Monsigny et al, 1988 Colorimetric determination of neutral sugars by a resorcinol sulfuric acid micromethod. Anal. Biochem., Vol. 175, pp. 525–530). The average number of oligomannoside motifs was 3.5 (oligomannoside$_{3.5}$-, GLcA$_{60}$-pLK)$.

IV. Oligolactosamine saccharides

Oligosaccharides containing three or more antennae ended with the N-acetyl lactosamine motif (Galβ4GlcNAcβ) are recognized by human liver parenchymal cell lectins and by many of the so called galactose specific lectins. An oligosaccharide containing three lactosamine motifs Galβ4GlcNAcβ4(Galβ4GlcNAcβ2)Manα3-(Galβ4GlcNAcβ2Manα6)Manβ4GlcNAcβ4GlcNAc was treated as an oligomannoside leading to the glycopeptide. Galβ4GlcNAcβ4(Galβ4GlcNAcβ2)Manα3-(Galβ4GlcNAcβ2Manα6)Manβ4GlcNAcβ4GlcNAcβ-pyroglutamyl-amido-ethyldithiopyridine or to the glycopeptide: Galβ4GlcNAcβ4(Galβ4GlcNAcβ2)Manα3-(Galβ4GlcNAcβ2Manα6)Manβ4GlcNAcβ4GlcNAcβ-pyrogutamyl-para-nitroanilide. Both types of glycopeptides have been linked to partially gluconoylated polylysine containing in average 190 lysyle resides and 60 gluconoyle residues under the conditions described to prepare the gluconoylated polylysine substituted with Lewis$^x$ oligosaccharies. The average number of oligolactosamine saccharides bound per polymer molecule was determined by a resorcinol sulfuric acid micromethod (Monsigny et al, 1988 Colorimetric determination of neutral sugars by a resorcinol sulfuric acid micromethod. Anal. Biochem., Vol. 175, pp. 525–530). The average number of oligolactosamine saccharides was 5 (oligolactosamine saccharides$_5$-GlcA$_{60}$-pLK).

3.) Peptide

Preparation of gluconoylated polylysine substituted with atrial natriuretic peptide (also called ANP):

preparation of gluconoylated polylysine substituted with dithiopyridinyl groups

Polylysine (50 mg; 0.91 µmol) being an average number of 60 gluconoyl residues per pLK molecule dissolved in 2 ml of dimethylsulfoxide was stirred for 12 hours at 20° C. with 4-succinimidyloxycarbonyl-α-methyl-α-(2-pyridinyldithio)-toluene (SMPT, Pierce, USA) (53 mg; 13.6 µmol). The polymer (MPT-GlcA$_{60}$-pLK) was precipitated by adding 10 volumes of isopropanol and spun down by centrifugation (1800 g for 15 min). The pellet was washed with isopropanol, collected by centrifugation (1800 g for 15 min), solubilized in distilled water and freeze-dried. The average number of MPT residues bound per polymer molecule was determined from absorbance at 343 nm ($\epsilon$=8080 M−1×cm−1) of pyridine thione released after reaction with tris (carboxyethyl)phosphine (TCEP). The average number of MPT resides was 10. (MPT$_{10}$-,GlcA$_{60}$-pLK).

ANP peptide reduction

The thiol group of the cysteinyl residue of the ANP peptide (CYSLRRSSAFGGRIDRIGAQSA) (SEQ. ID. NO: 8) (5 mg; 1.7 µmol) protected by reaction with dithiodipyridine was reacted for 15 min at 20° C. with TCEP (0.45 mg; 1.6 µmol) in 1 mol of 0.1M NaCl 0 1.M tris/HCL buffer, pH 7.6.

preparation of gluconoylated polylysine substituted with the ANP peptide

Gluconoylated polylysine bearing an average number of 10 MPT residues (MPT$_{10}$-GLcA$_{60}$pLK) (10 mg ; 0.18 µmol) in 1 ml 0.1M Nacl. 0.1M tris/HCl buffer, pH 7.6 was stirred for 24 hours at 20° C. with reduced ANP peptide (1.5 mg ; 0.51 µmol). The polymer (ANP-S-GlcA$_{60}$-pLK) was precipitated by adding 10 volumes of isopropanol and spun down by centrifugation (1800 g for 15 min). The pellet was washed with isopropanol, collected by centrifugation (1800 g for 15 min), solubilized in distilled water and freeze-dried. The average number of ANP residues bound per polymer molecule was determined by an HPLC reverse phase (C18 column, Supelcosil LC-18S-DB, Supelco, Bellefonte, Pa., USA) amino-acid analysis after 5.6N HCl hydrolysis at 105° C. for 72 hours. The average number of ANP residues was 2.

Gene transfer into rabbit smooth muscle (Rb1) cells (FIG. 13)

Rb1 cells (2×105) (Nachtigal et al (1989) In Vitro Cellular Developmental Biology 25, 892–898) were incubated at 37° C. in 1 ml DMEM containing 1% FBS, 100 µM chloroquine and pSV2LUC (5 µg) complexed with either polylysine (2.5 µg), gluconoylated polylysine (GlcA$_{60}$pLK) (7.5 µg) or gluconoylated polylysine substituted with the ANP peptide (ANP$_2$-GlcA$_{60}$-pLK) (10 µg). The DNA/polymer complexes were formed with the lowest polymer to DNA molar ratio inducing a complete retardation of all the DNA in electrophoresis as described (Erbacher et al (1995) Glycosylated polylysine/DNA complexes: gene transfer efficiency in relation with the size and the sugar substitution level of glycosylated polylysines and with the plasmid size. Bioconjugate Chem., Vol 6 pp. 401–410). After 4 hours of incubation, the medium was removed and cells were incubated in 2 ml RPMI 1640 containing 10% FBS in the absence of any other additive. The gene expression was determined 24 hours later by measuring the luciferase activity in cell lysates. RLU, the number of relative light units, represents the luciferase activity in $10^6$ Rb1 cells.

Summary of genes which have been transfected by using glyconoylated polylysines including ribonoylated and heptanoylated polylysines and which have been described thereafter Ribonoylated and heptonoylated polylysine
  Genes encoding therapeutic RNA
  antisense RNA: pAR6
  ribozyme: pKSRVaR8
  Laboratory reagents and Genetic Markers
  luciferase: pSV2LUC
  CAT: chloramphenicol acetyl transferase
  Nuclear β-galactosidase: pKSRVaR8
  Genes encoding endogenous proteins and biological modulators
  Stable Clones: HOS CAT/TAT: pLTR$_{HIV}$-TAT; pLTR$_{HIV}$-CAT(pROF4)
  tat: transactivation protein of the HIV retrovirus
  MR60: pCDNA$_3$MR
  Sialoadhesin: pCDNA$_1$SA
  Genetic vaccination
  Antigens: nucleocapsid of the influenza virus: pCMVNP Various glyconoylated polylysines have been used in addition to the gluconoylated ones, the ribonoylated ones and the heptonoylated ones are exemplified below Preparation of ribonoylated polylysines (RibApLK):

Poly-L-lysine, HBr (pLK, average Mr=40,000; average degree of polymerization DP=190) (Bachem Feinchemikalien, Bubendorf, Switzerland) was partially substituted with ribonoyl residues (RibA) as follows: polylysine in p-toluene sulfonate form (50 mg; 0.86 µmol) in 3 ml DMSO (dimethylsulfoxide) in the presence of diisopropylethylamine (37 µl; 205 µmol) and 1% water, was allowed to react for 24 h at 20° C. with quantities of D-ribonolactone (D-ribonic acid γ-lactone) ranging from 9 mg (61 µmol) to 30 mg (194 µmol) (Aldrich, Strasbourg, France). The ribonoylated polylysine was precipitated by adding 10 volumes of isopropanol. After centrifugation (1800 g for 15 min), the pellet was washed with isopropanol and collected after another centrifugation. The pellet was dissolved in distilled water and was freeze-dried. The mean number of fixed ribonoyl residues per molecule of polylysine (FIG. 14) was determined by 1H-NMR spectroscopy: 1H-NMR (300 MHz, D$_2$O) δ7.75 (2H, d, Jortho=7.79 Hz, C3 and C5 p-toluene sulfonate aromatic protons); 7.42 (2H, d, Jortho=7.61 Hz, C2 and C6 p-toluene sulfonate aromatic protons); 4.34 (1H, C2-proton and 1H, C8-proton); 4.13 (1H, C9-proton); 3.68 3.72, 3.84 and 3.88 (1H, C10-protons); 3.79 (2H, C11-methylene protons); 3.26 (2H, C6-methylene protons of a ribonoylated lysine residue); 2.97 (2H, C6-methylene protons of a lysine residue); 2.42 (3H, tosyl methyl protons); 1.77, 1.68, 1.56 and 1.43 (6H, C3-, C4- and C5-methylene protons). The mean number of RibA molecules bound per pLK molecule was determined from: x=2. (hRibA/hLys).DP, where hRibA was the value of the integration in the range 3.6 to 3.9 ppm of the 3 protons (1H C10 and 2H C11) of RibA, hLys that in the range of 1.3 to 1.9 ppm of the 6 methylene protons (C3, C4 and C5) of lysine residues and DP was the degree of polymerization of pLK.

Gene transfer into HepG2 cells using ribonoylated polylysine (RibA-pLK)

The DNA/polymer complexes formed between the pSV2LUC plasmid and the polylysine substituted with different quantities of ribonoyle residues (from 10 to 80%) were determined by electrophoresis on agarose gel. The HepG2 cells were incubated at 37° C. for 4 hours at 37° C. in humidified atmosphere (95% air, 5% $CO_2$) in culture medium containing FBS in the presence of 100 µM of chloroquine with 1.5 nM of plasmid complexed with each conjugate. The medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed per mg of protein which corresponds to 1.2 million of HepG2 cells, as a function of the molar ratio RibA/pLK and the degree of substitution of polylysine (%). The efficiency of the transfection was close to that obtained when the gluconylated polylysines were used instead of the ribonoylated polylysines within a variability lower than 10%.

Preparation of heptonoylated polylysines (HepApLK)

Poly-L-lysine, HBr (pLK, average Mr=40,000; average degree of polymerization DP=190) (Bachem Feinchemikalien, Bubendorf, Switzerland) was partially substituted with heptonoyl residues (HepA) as follows: polylysine in p-toluene sulfonate form 50 mg; 0.86 µmol) in 3 ml DMSO (dimethylsulfoxide) in the presence of diisopropylethylamine (37 µl; 205 µmol) and 1% water, was allowed to react for 24 h at 20° C. with quantities of D-glucoheptono-1,4-lactone (D-glycero-D-guloheptono γ-lactone) ranging from 13 mg (61 µmol) to 40 mg (194 µmol) (Aldrich, Strasbourg, France). The heptonoylated polylysine was precipitated by adding 10 volumes of isopropanol. After centrifugation (1800 g for 15 min), the pellet was washed with isopropanol and collected after another centrifugation. The pellet was dissolved in distilled water and was freeze-dried. The mean number of fixed heptonoyl residues per molecule of polylysine (FIG. 15) was determined by 1H-NMR spectroscopy: 1H-NMR (300 MHz, $D_2O$) δ7.75 (2H, d, Jortho=7.79 Hz, C3 and C5 p-toluene sulfonate aromatic protons); 7.42 (2H, d, Jortho=7.61 Hz, C2 and C6 p-toluene sulfonate aromatic protons); 4.34 (1H, C2-proton and 1H, s, C8-proton); 4.06 (1H, C9-proton); 4.00 (1H, C10-proton); 3.68, 3.72, 3.84 and 3.88 (2H, C11- and C12-protons); 3.79 (2H, C13-methylene protons); 3.26 (2H, C6-methylene protons of a heptonoylated lysine residue); 2.97 (2H, C6-methylene protons of a lysine residue); 2.42 (3H, tosyl methyl protons); 1.77, 1.68, 1.56 and 1.43 (6H,C3-, C4- and C5-methylene protons). The mean number of HepA molecules bound per pLK molecule was determined from: x=3/2. (hHepA/hLys).DP, where hHepA was the value of the integration in the range of 3.6 to 3.9 ppm of the 4 protons (1H C11, 1H C12 and 2H C13) of HepA, hLys that in the range of 1.3 to 1.9 ppm of the 6 methylene protons (C3, C4 and C5) of lysine residues and DP was the degree of polymerization of pLK.

Gene transfer into HepG2 cells using heptonoylated polylysine (HepA-pLK)

The DNA/polymer complexes formed between the pSV2LUC plasmid and the polylysine substituted with different quantities of heptonoyle residues (from 10 to 80%) were determined by electrophoresis on agarose gel. The HepG2 cells were incubated at 37° C. for 4 hours in humidified atmosphere (95% air, 5% $CO_2$) in culture medium containing FBS in the presence of 100 µM of chloroquine with 1.5 nM of plasmid complexed with each conjugate. The medium was discarded and the cells were incubated in the absence of both chloroquine and plasmid. Expression of the gene of luciferase was determined 48 hours later by measuring the activity of luciferase in the cellular lysates. The relative light units (RLU) emitted were expressed per mg of protein which corresponds to 1.2 million of HepG2 cells, as a function of the molar ratio HepA/pLK and the degree of substitution of polylysine (%). The efficiency of the transfection was close to that obtained when the gluconylated polylysines were used instead of the heptonoylated polylysines within a variability lower than 10%.

Genes encoding therapeutic RNA

RNA antisense:

Inhibition of HIV Tat protein expression by gene transfer using lactosylated and gluconoylated polylysine ($Lact_{30}GlcA_{50}$-pLK) and pAR6 plasmid A pAR6/GlcApLK complex was prepared by adding dropwise and with constant mixing, 22.5 µg $Lact_{30}GlcA_{50}$-pLK in 0.45 ml serum-free DMEM to 1.05 ml serum-free DMEM containing 15 µg pAR6 plasmid (encoding an antisense RNA targeted to $Tat_{HIV}$ region. Sczakiel, G., Oppenlander, M., Rittner, K. and Pawlita, M. (1992) Tat- and rev-directed antisense RNA expression inhibits and abolishes replication of human immunodeficiency virus type 1: a temporal analysis. J. Virol. 66, 5576–5581). The solution was kept for 30 min at 20° C., then diluted with 1.5 ml serum-free DMEM, supplemented with 1% FBS and made 100 µM in chloroquine and used to transfect a stably $LTR_{HIV}$-CAT, $LTR_{HIV}$-Tat-transfected HOS (B3C cells) clone. B3C cells ($2\times10^5$ cells plated in 8 cm$^2$ culture dish) were transfected on $D_0$ (D=day) with 5 µg/ml pAR6 complexed with $Lact_{30}GlcA_{50}$-pLK. After a 4h incubation at 37° C., the medium was removed and cells were further incubated at 37° C. in humidified atmosphere (95% air, 5% $CO_2$) in 4 ml culture medium containing 10% FBS in the absence of any other additive. The cells were further transfected on D+1 with 5 µg/ml pAR6 complexed with $Lact_{30}GlcA_{50}$-pLK. After a 4 h incubation at 37° C., the medium was removed and cells were further incubated at 37° C. in humidified atmosphere (95% air, 5% $CO_2$) in 4 ml culture medium containing 10% FBS in the absence of any other additive. The cells were harvested 24 h following transfection for CAT measurement by an immunofluorescence assay using rabbit anti-CAT immunoglobulins and FITC-goat anti-rabbit immunoglobulin. The results are presented in FIG. 16: 3:1 and 3:2 are negative control histograms; 3:3 is a positive control histogram; 3.4 shows that the antisense RNA expressed upon transfection with a DNA complexed with the gluconoylated polylysine efficiently inhibits the expression of the marker protein CAT, chloramphenicol acetyl transferase.

Inhibition of HIV Tat protein expression by gene transfer using gluconoylated polylysine ($GlcA_{74}$-pLK) and pAR6 plasmid A pAR6/GlcApLK complex was prepared by adding dropwise and with constant mixing, 2.25 µg $GlcA_{74}$-pLK in 0.45 ml serum-free DMEM to 1.05 ml serum-free DMEM containing 15 µg pAR6 plasmid (encoding an antisense RNA targeted to $Tat_{HIV}$ region. Sczakiel, G., Oppenlander, M., Rittner, K. and Pawlita, M. (1992) Tat- and rev-directed antisense RNA expression inhibits and abolishes replication of human immunodeficiency virus type 1: a temporal analysis J. Virol. 66, 5576–5581). The solution was kept for 30 minutes at 20° C., then diluted with 1.5 ml serum-free DMEM, supplemented with 1% FBS and made 100 µM in chloroquine and used to transfect a stably $LTR_{HIV}$-CAT, $LTR_{HIV}$-TAT-transfected HOS (B3C cells) clone. B3C cells ($2\times10^5$ cells plated in 8 cm² culture dish) were transfected on $D_0$ with 5 µg/ml pAR6 complexed with $GlcA_{74}$-pLK. After a 4 h incubation at 37° C., the medium was removed and cells were further incubated at 37° C. in humidified atmosphere (95% air, 5% $CO_2$) in 4 ml culture medium containing 10% FBS in the absence of any other additive. The cells were further transfected on D+1 with 5 µg/ml pAR6 complexed with $GlcA_{74}$-pLK. After a 4 h incubation at 37° C., the medium was removed and cells were further incubated at 37° C. in humidified atmosphere (95% air, 5% $CO_2$) in 4 ml culture medium containing 10% FBS in the absence of any other additive. The cells were harvested 24 h following transfection for CAT measurement by an immunofluorescence assay using rabbit anti-CAT immunoglobulins and FITC-goat anti-rabbit immunoglobulin.

Ribozyme: Inhibition of CAT protein expression by gene transfer using lactosylated and gluconoylated polylysine ($Lact_{30}GlcA_{50}$-pLK) and pKSRV aR8 plasmid encoding a ribozyme A pKSRVaR8/GlcApLK complex was prepared by adding, dropwise and with constant mixing, 22.5 µg $Lact_{30}GlcA_{50}$-pLK in 0.45 ml serum-free DMEM to 1.05 ml serum-free DMEM containing 15 µg pKSRVaR8 plasmid (encoding a ribozyme targeted to HIV LTR region. Ventura, M., Wang, P., Franck, N. and Saragosti, S. (1994) Ribozyme targeting of HIV-1 LTR. Biochem-Biophys-Res-Commun. 203.889–898). The solution was kept for 30 min at 20° C., then diluted with 1.5 ml serum-free DMEM, supplemented with 1% FBS and made 100 µM in chloroquine and used to transfect a stably $LTR_{HIV}$-CAT, $LTR_{HIV}$-TAT-transfected HOS (B3C cells) clone. B3C cells ($2\times10^5$ cells plated in 8 cm² culture dish) were transfected on $D_0$, with 5 µg/ml pAR6 complexed with $Lact_{30}GlcA_{50}$-pLK. After a 4 h incubation at 37° C., the medium was removed and cells were further incubated at 37° C. in humidified atmosphere (95% air, 5% $CO_2$) in 4 ml culture medium containing 10% FBS in the absence of any other additive. The cells were further transfected on D+1 with 5 µg/ml pAR6 complexed with $Lact_{30}GlcA_{50}$-pLK. After a 4 h incubation at 37° C., the medium was removed and cells were further incubated at 37° C. in humidified atmosphere (95% air, 5% $CO_2$) in 4 ml culture medium containing 10% FBS in the absence of any other additive. The cells were harvested for CAT measurement 24 h following transfection by an immunofluorescence assay using rabbit anti-CAT immunoglobulins and FITC-goat anti-rabbit immunoglobulin.

Laboratory reagents and gene markers

Gene markers: Nuclear Galactosidase in addition to the luciferase and the chloramphenicol acetyl transferase: Gene transfer in HepG2 cells using lactosylated and gluconoylated polylysine ($Lact_{30}GlcA_{50}$-pLK) and pCMV nlsLacZ plasmid.

A DNA/$Lact_{30}GlcA_{50}$-pLK complex was formed between the pCMV nlsLacZ plasmid and $Lact_{30}GlcA_{50}$-pLK. HepG2 cells were incubated at 37° C. for 4 hours in humidified atmosphere (95% air, 5% $CO_2$) in culture medium containing FBS in the presence of 100 µM of chloroquine with 1.5 nM of pKSRVaR8 (pUT651, CAYLA, Toulouse, France) complexed with $Lact_{30}GlcA_{50}$-pLK. pCMV nlsLacZ plasmid was a plasmid encoding the β-galactosidase of E. Coli containing a nuclear localization signal (nls). The medium was discarded and the cells were incubated in the absence of both chloroquine and plasmid. Expression of E. Coli β-galactosidase gene was determined 48 hours later by the colorimetric method using 4-chloro-3-indolyl-β-D-galactoside. The efficacy of the transfection is shown as colored dots on the FIG. 17.

Generation of stable transfectants expressing CAT under the control of the TAR sequence specifically activated by the $tat_{HIV}$:: $LTR_{HIV}$-CAT, TAT-transfected HOS cells (B3C clone) using lactosylated and gluconoylated polylysine ($Lact_{30}GlcA_{50}$-pLK)

The stably $LTR_{HIV}$-CAT, $LTR_{HIV}$-TAT-transfected HOS clones were generated by co-transfection with $pLTR_{HIV}$-TAT (Ventura, M., Wang P., Franck, N. and Saragosti, S. (1994) Ribozyme targeting of HIV-1 LTR. Biochem. Biophys. Res. Commun. 203, 889–898) and $pLTR_{HIV}$-CAT plasmids complexed with using lactosylated and gluconoylated polylysine ($Lact_{30}GlcA_{50}$-pLK). $pLTR_{HIV}$-CAT (pROF4, J. Raimond, CBM, Orléans) is a bifunctional vector in which the $LTR_{RSV}$ promoter drives the express of Tn5 aminoglycoside phosphotransferase (neo) dominant selectable marker in eukaryotic cells, and the human immunodeficiency virus type-1 $LRT_{HIV}$ as promoter directs the CAT reporter gene. A ($pLTR_{HIV}$-TAT, $pLTR_{HIV}$-CAT)/$Lact_{30}GlcA_{50}$-pLK complex was prepared by adding, dropwise and with constant mixing, 200 µg $Lact_{30}GlcA_{50}$-pLK in 2.4 ml serum-free DMEM to 5.6 ml serum-free DMEM containing 40 µg $pLTR_{HIV}$-CAT and 40 µg $pLTR_{HIV}$-TAT plasmids. The solution was kept for 30 min. at 20° C., then diluted one time with serum-free DMEM, supplemented with 1% FBS and made 100 µM in chloroquine. The medium of HOS cells ($2\times10^6$ cells) plated on day 0 into 25 cm² Petri culture dishes was removed on day 1 and the cells were incubated at 37° C. in 5.5 ml of the above solution containing the plasmids/$Lact_{30}GlcA_{50}$-pLK complex in humidified atmosphere (95% air, 5% $CO_2$). After 4 h incubation at 37° C., the medium was removed and cells were further incubated at 37° C. in humidified atmosphere (95% air, 5% $CO_2$) in 10 ml culture medium containing 10% FBS in the absence of any other additive. The cells were harvested 48 h following transfection upon incubation at 37° C. in PET, washed 2 times in PBS and $1\times10^6$ cells were plated in 25 cm² Petri culture dishes in culture medium with 10% FBS without streptomycin and penicillin. After 48 h, transduced cells were then selected with 300 µg/ml of a neomycin analog (G418 sulfate). G418 resistant clones were obtained upon 2–3 weeks and their CAT expression were measured. CAT assay: the culture medium was discarded and adherent cells were washed in PBS. The cells were then harvested after incubation at 37° C. in PET, washed 2 times in PBS, resuspended in 1 ml PBS, transferred in a 1.5 ml Eppendorf tube and spun down at 800 g for 5 min. The pellet was resuspended on 60 µl of homogenization buffer (100 mM Tris-phosphate buffer, pH 7.8 with 1% Triton X100). The suspension was mixed with a vortex, kept for 10 min at 4° C., centrifuged at 20.000 g for 5 min., and the supernatant was warmed at 60° C. for 10 min. For CAT assay, 200 µl of a 10 ml 100 mM Tris-phosphate buffer pH 7.8 containing $1.85\times10^5$ Bq ³H-Acetyl Coenzyme A (Amersham), 1 mg Acetyl Coenzyme A (Sigma) and 4 mg chloramphenicol (Sigma) were added to 50 µl of the cell lysate, followed by incubation at 37° C. for 1 h. The solution was then mixed with 7 ml non-aqueous counting scintillant Lipofluor (Baker Chemicals B. V., Deventer, The Netherlands) to solubilize tritiated forms of acetyl chloramphenicol (³H-Acetyl Coenzyme A is not soluble in Lipofluor) and radioactivity was measured 1 h later in a liquid scintillation analyzer (Packard). The efficiency of the expression in stable transfectants is exemplified in FIG. 18.

A transactivating factor: tat as biological response modifier Gene transfer in HOS cells using lactosylated and gluconoylated polylysine ($Lact_{30}GlcA_{50}$-pLK) and $pLTR_{HIV}$-TAT plasmid A DNA/Lact$_{30}$GlcA$_{50}$-pLK complex was formed between the plasmid and Lact$_{30}$GlcA$_{50}$-pLK. pLTR$_{HIV}$-TAT is a plasmid encoding the transactivation factor of the HIV virus. The cells were incubated at 37° C. for 4 hours in humidified atmosphere (95% air, 5% CO$_2$) in culture medium containing FBS in the presence of 100 µM of chloroquine with 1.5 nM of plasmid complexed with Lact$_{30}$GLcA$_{50}$-pLK. The medium was discarded and the cells were incubated in humidified atmosphere (95% air, 5% CO$_2$) in culture medium containing FBS in the absence of both chloroquine and plasmid. The expression of tat gene was achieved by using an immunofluorescence assay and observation by confocal microscopy. Cells (2.10$^5$/well) plated on glass coverslips were cultured for 48 h after transfection. Then, they were processed for immunolabelling using an anti-tat antibody. After extensive washing in PBS containing 10 mg/ml BSA, cells were fixed by inubatio in 30 mg/ml p-formaldehyde and 0.1% glutaraldehyde (Merck Darmstadt, Germany) PBS for 1 h at 37° C., followed by incubation 10 min at room temperature in 50 mM NH$_4$Cl and then permeabilized with 1 mg/ml saponin in PBS for 15 min at room temperature. Cells were incubated 1 h with a specific anti-tat antibody, then with a secondary anti-isotype antibody labelled with a fluorophore (Sigma, St. Louis, Mo., USA). The overexpression of tat in the nucleus is exemplified in FIG. 19b.

A mannose specific lectin: MR60, an intracellular recycling sugar-binding protein Gene transfer in HOS cells using lactosylated and gluconoylated polylysine (Lact$_{30}$GlcA$_{50}$-pLK) and pCDNA$_3$MR plasmid A DNA/Lact$_{30}$GlcA$_{50}$-pLK complex was formed between the pcDNA$_3$MR plasmid and Lact$_{30}$GlcA$_{50}$-pLK- pcDNA$_3$MR is a plasmid encoding the intracellular mannose-specific lectin MR60 (Arar C, Carpentier V, Le Caer J. P., Monsigny M, Legrand A and Roche AC. (1995) ERGIC-53, a membrane protein of the ER-Golgi intermediate compartment is identical to MR60 an intracellular mannose specific lectin of myelomonocytic cells. J. Biol. Chem., 270, 3551–3553). The cells were incubated at 37° C. for 4 hours in humidified atmosphere (95% air, 5% CO$_2$) in culture medium containing FBS in the presence of 100 µM of chloroquine with 1.5 nM of plasmid complexed with Lact$_{30}$GlcA$_{50}$-pLK. The medium was discarded and the cells were incubated in the absence of both chloroquine and plasmid. The expression of MR60 gene was achieved by using an immunofluorescence assay and observation by confocal microscopy. Cells (2.10$^5$/well) plated on glass coverslips were cultured for 48 h after transfection. Then, they were processed for immunolabelling using an anti-ERGIC-53 antibody (a marker of the intermediate compartment between the ER and the Golgi apparatus kindly provided by Dr. H. P. Hauri, Biozentrum, Basel, Switzerland) (Schweizer, A., Fransen, J. A., Matter, K., Kreis, T. E., Ginsel, L. and Hauri, H. P. (1990). Identification of an intermediate compartment involved in protein transport from ER to Golgi apparatus. Eur. J. Cell Biol. 53: 185–196). After extensive washing in PBS containing 10 mg/ml BSA, cells were fixed by incubation in 30 mg/ml p-formaldehyde and 0.1% glutaraldehyde (Merck Darmstadt, Germany) PBS for 1 h at 37° C., followed by incubation 10 min at room temperature in 50 mM NH$_4$Cl and then permeabilized with 1 mg/ml saponin in PBS for 15 min. at room temperature. Cells were incubated 1 h with a specific antibody, then with a secondary anti-isotype antibody labelled with a fluorophore (Simga, St. Louis, Mo., USA); alternatively the overexpression of MR60 was assessed by using fluorescein-labelled mannosylated serum albumin, a fluorescent neoglycoprotein suitable to visualize endogenous lectins. The overexpression of MR60 is exemplified in FIG. 20.

Gene transfer in COS cells using Lactosylated and gluconoylated polylysine (Lact$_{30}$GLcA$_{50}$-pLK) and pCDNA$_3$MR plasmid A DNA/Lact$_{30}$GlcA$_{50}$-pLK complex was formed between the pDNA$_3$MR plasmid and Lact$_{30}$GlcA$_{50}$-pLK. pcDNA$_3$MR is a plasmid encoding the Intracellular mannose-specific lectin MR60 (Arar C, Carpentier V, Le Caer J. P., Monsigny M, Legrand A and Roche A. C. (1995) ERGIC-53, a membrane protein of the ER-Golgi intermediate compartment is identical to MR60 an intracellular mannose specific lectin of myelomonocytic cells. J. Biol. Chem., 270, 3551–3553). The cells were incubated at 37° C. for 4 hours in humidified atmosphere (95% air, 5% CO$_2$) in culture medium containing FBS in the presence of 100 µM of chloroquine with 1.5 nM of plasmid complexed with Lact$_{30}$GlcA$_{50}$-pLK. The medium was discarded and the cells were incubated in the absence of both chloroquine and plasmid. The expression of MR60 gene was achieved by using an immunofluorescence assay and observation by confocal microscopy. Cells (2.10$^5$/well) plated on glass coverslips, were processed for immunolabelling using an anti-ERGIC-53 antibody (a marker of the intermediate compartment between the ER and the Golgi apparatus kindly provided by Dr. H. P. Hauri, Biozentrum, Basel, Switzerland) (Schweizer, A., Fransen, J. A., Matter, K., Kreis, T. E., Ginsel, L. and Hauri, H. P. (1990). Identification of an intermediate compartment involved in protein transport from ER to Golgi apparatus. Eur. J. Cell Biol. 53: 185–196). After extensive washing in PBS containing 10 mg/ml BSA, cells were fixed by incubation in 30 mg/ml p-formaldehyde and 0.1% glutaraldehyde (Merck Darmstadt, Germany) PBS for 1 h at 37° C., followed by incubation 10 min at room temperature in 50 mM NH$_4$Cl and then permeabilized with 1 mg/ml saponin in PBS for 15 min. at room temperature. Cells were incubated 1 h with a specific antibody, then with a secondary anti-isotype antibody labelled with a fluorophore (Simga, St. Louis, Mo., USA); alternatively the overexpression of MR60 was assessed by using fluorescein-labelled mannosylated serum albumin, a fluorescent neoglycoprotein suitable to visualize endogenous lectins. The overexpression of MR60 is exemplified in FIG. 20.

A neuraminic acid specific lectin: sialoadhesin

Gene transfer in HepG2 cells using Lactosylated and gluconoylated polylysine (Lact$_{30}$GlcA$_{50}$-pLK) and pCDNA$_1$SA plasmid.

A DNA/Lact$_{30}$GlcA$_{50}$-pLK complex was formed between the pcDNA$_1$SA plasmid and Lact$_{30}$GlcA$_{50}$-pLK. pcDNA$_1$SA is a plasmid encoding the full-length sialoadhesion provided by Paul R. Crocker, University of Oxford, OXFORD, UK (Crocker P. R., Mucklow S., Bouckson V., McWilliam A., Willis A. C., Gordon S., Milon G., Kelm S. and Bradfield P. (1994) Sialoadhesin, a macrophage sialic acid binding receptor for hemopoietic cells with 17 immunoglobulin-like domains. Embo J. 13, 4490–4503). The cells were incubated at 37° C. for 4 hours in humidified atmosphere (95% air, 5% CO$_2$) in culture medium containing FBS in the presence of 100 µM of chloroquine with 1.5 nM of plasmid complexed with Lact$_{30}$GlcA$_{50}$-pLK. The medium was discarded and the cells were incubated in the absence of both chloroquine and plasmid. The expression of sialoadhesin gene expression was achieved by using an immunofluorescence assay and FACS analysis. Cells (2.10$^5$/ well) were processed for immunolabelling using monoclonal antibodies 3D6 and SER-4 (provided by P. Crocker). After extensive washing in PBS containing 10 mg/ml BSA, cells were analyzed by flow cytometry, showing that about 30% of them did overexpress the lectin, sialoadhesin.

Genetic vaccines: Transfer of genes encoding antigenic proteins such as viral proteins Gene transfer in HepG2 cells using lactosylated and gluconoylated polylysine ($Lact_{30}GlcA_{50}$-pLK) pCMVNP plasmid encoding an influenza virus antigen A DNA/$Lact_{30}GlcA_{50}$-pLK complex was formed between the pCMVNP plasmid and $Lact_{30}GlcA_{50}$-pLK. pCMVNP (PM914) is a plasmid encoding the nucleoprotein of influenza virus provided from Pasteur Mérieux, Sérums & Vaccins (Marcy l'Etoile, France). The cells were incubated at 37° C. for 4 hours in humidified atmosphere (95% air, 5% $CO_2$) in culture medium containing FBS in the presence of 100 µM of chloroquine with 1.5 nM of plasmid complexed with $Lact_{30}GlcA_{50}$-pLK. The medium was discarded and the cells were incubated in the absence of both chloroquine and plasmid. The expression of MR60 gene expression was achieved by using an immunofluorescence assay and observation by confocal microscopy. Cells ($2.10^5$/well) plated on glass coverslips, were processed for immunolabelling using a rabbit polyclonal antibody directed against the nucleoprotein, NP of the influenza virus, strain A:N1B16. After extensive washing in PBS containing 10 mg/ml BSA, cells were fixed by incubation in 30 mg/ml p-formaldehyde and 0.1% glutaraldehyde (Merck Darmstadt, Germany) PBS for 1 h at 37° C., followed by incubation 10 min. at room temperature in 50 mM $NH_4Cl$ and then permeabilized with 1 mg/ml saponin in PBS for 15 min. at room temperature. Cells were incubated 1 h with specific rabbit polyclonal antibody, then with a secondary antibody labelled with a fluorophore (Sigma, St. Louis, Mo., USA). The expression of the viral antigen is exemplified in FIG. 21.

FIG. 14 Structure of ribonoylated polylysine

FIG. 15 Structure of heptonoylated polylysine

FIG. 16 Flow cytometry analysis of the inhibition of the expression of the marker protein CAT by transfection with a plasmid encoding a specific antisense RNA.

FIG. 17 The nucleus of cells expressing a large amount of galactosidase is blue.

FIG. 18 Stable transfected cells express a large amount of CAT.

FIG. 19 The cells expressing tat are strongly labelled. HepG2 cells were mock-transfected (a) or transfected with $pLTR_{HIV}$-tat (b).

Figure 20B:
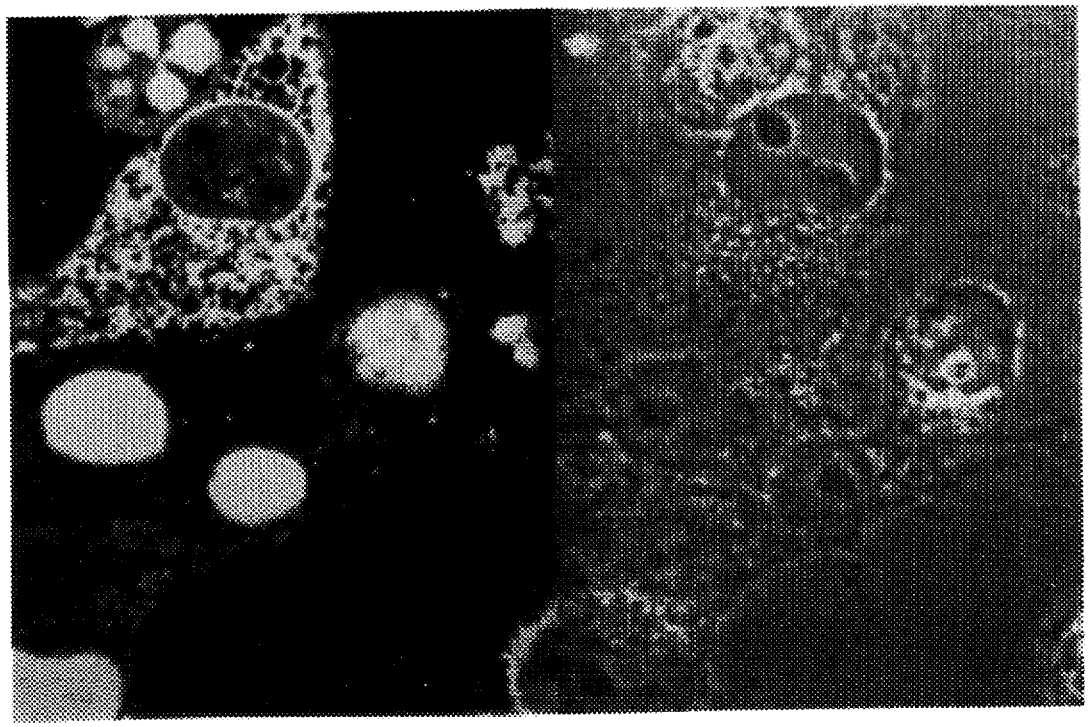

FIG. 20 The cells overexpressing MR60 are strongly labelled in their cytoplasm. COS cells were mock-transfected (a) with p $CDNA_3MR$(b). Left: confocal fluorescence image; Right: phase-contrast image.

FIG. 21 Cells expressing the viral antigen are specifically labelled with anti-nucleoprotein antibodies.

Various modifications of the compounds and method of the invention may be made without departing from the spirit or scope thereof and it is to be understood that the invention is intended to be limited only as defined in the appended claims.

What is claim is:

1. A compound consisting of polylysine conjugated to non-charged residues and to recognition signals:
    wherein at least one free amino function of said polylysine is substituted with said non-charged residues, at least one free amino function of said polylysine is substituted with said recognition signal, and the conjugated polylysine contains at least 30% unsubstituted free amino functions;
    wherein said non-charged residues are selected from the group consisting of gluconolactone, ribonolactone, and heptonolactone; and
    wherein said recognition signals comprise a peptide; an oligosaccharide selected from the group consisting of Lewis$^a$, Lewis$^b$, Lewis$^x$, oligomannosides, and oligolactosaminides; or a monosaccharide selected from the group consisting of alpha or beta conformers of neutral monosaccharides; alpha or beta conformers of 2-deoxy, 2-amino or 2-deoxy, 2-acetamido neutral monosaccharides; alpha or beta conformers of glycuronic acid derivatives of neutral monosaccharides; alpha or beta conformers of L-iduronic acid, keto-deoxy-octonic acid, N-acetyl-neuraminic acid, or N-glycoloyl-neuraminic acid; and neutral 6-deoxy monosaccharides;
    which monosaccharide optionally comprises at least one modification selected from the group consisting of isopropylydene, pyruvilydene, acetyl, propionyl, phosphoryl, sulfate, lactyl, and butanoyl; and
    the reducing function of said monosaccharide is optionally substituted with a phenol, an alcohol, an aromatic amine, an aliphatic amine, an aromatic thiol, an aliphatic thiol.

2. The compound of claim 1 wherein said monosaccharide is selected from the group consisting of galactose, mannose, fucose, glucose, ribose, arabinose, xylose, and rhamnose.

3. The compound of claim 1 wherein the recognition signal is Lewis$^a$.

4. The compound of claim 1 wherein the recognition signal is Lewis$^x$.

5. The compound of claim 1 wherein the recognition signal is Lewis$^b$.

6. The compound of claim 1 wherein the recognition signal is an oligomannoside.

7. The compound of claim 1 wherein the recognition signal is an oligolactosaminide.

8. The compound of claim 1 wherein the recognition signal is atrial natiuretic peptide (ANP).

9. A composition comprising the compound of claim 1 and a nucleic acid.

10. The composition of claim 9 wherein the nucleic acid encodes a genetic marker selected from the group consisting of luciferase, β-galactosidase, hygromycin resistance, neomycin resistance, and chloramphenicol acetyl transferase.

11. The composition of claim 9 wherein the nucleic acid encodes a protein selected from the group consisting of p16, p53, thymidine kinase, IL2, IL4, and TNFα.

12. The composition of claim 9 wherein the nucleic acid encodes a viral antigen.

13. The composition of claim 9 wherein the nucleic acid encodes an RNA selected from the group consisting of a sense RNA, an antisense RNA, and a ribozyme.

14. The composition of claim 9 wherein the nucleic acid encodes a lectin, a mannose receptor, a sialoadhesin, or a retroviral transactiviating factor (TAT).

15. A method of transfecting cultured cells comprising incubating said cells in the presence of the composition of claim 9 under conditions wherein said composition enters said cells, and the nucleic acid of said composition is released.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 28
        ( B ) TYPE: Amino Acid
        ( C ) STRANDEDNESS: Unknown
        ( D ) TOPOLOGY: Unknown ( i i ) MOLECULE TYPE: PEPTIDE ( x i ) SEQUENCE DESCRIPTION: SEQ ID NO:1:

```
His Ser Asp Ala Val Phe Thr Asp Asn Tyr Thr Arg Leu Arg
 1               5                  10
Lys Gln Met Ala Val Lys Lys Tyr Leu Asn Ser Ile Leu Asn
15                  20                  25
```

( 2 ) INFORMATION FOR SEQ ID NO:2:

( i ) SEQUENCE CHARACTERISTICS:
        ( A ) LENGTH: 28
        ( B ) TYPE: Amino Acid
        ( C ) STRANDEDNESS: Unknown
        ( D ) TOPOLOGY: Unknown ( i i ) MOLECULE TYPE: PEPTIDE ( x i ) SEQUENCE DESCRIPTION: SEQ ID NO:2:

```
Ser Leu Arg Arg Ser Ser Cys Phe Gly Gly Arg Met Asp Arg
 1               5                  10
```

```
Ile  Gly  Ala  Gln  Ser  Gly  Leu  Gly  Cys  Asn  Ser  Phe  Arg  Tyr
 15                  20                  25
```

( 2 ) INFORMATION FOR SEQ ID NO:3:

( i ) SEQUENCE CHARACTERISTICS:
        ( A ) LENGTH: 9
        ( B ) TYPE: Amino Acid
        ( C ) STRANDEDNESS: Unknown
        ( D ) TOPOLOGY: Unknown ( i i ) MOLECULE TYPE: PEPTIDE ( x i ) SEQUENCE DESCRIPTION: SEQ ID NO:3:

```
His  Asp  Met  Asn  Lys  Val  Leu  Asp  Leu
 1                   5
```

( 2 ) INFORMATION FOR SEQ ID NO:4:

( i ) SEQUENCE CHARACTERISTICS:
        ( A ) LENGTH: 9
        ( B ) TYPE: Amino Acid
        ( C ) STRANDEDNESS: Unknown
        ( D ) TOPOLOGY: Unknown ( i i ) MOLECULE TYPE: PEPTIDE ( x i ) SEQUENCE DESCRIPTION: SEQ ID NO:4:

```
Arg  Pro  Pro  Gly  Phe  Ser  Pro  Phe  Arg
 1                   5
```

( 2 ) INFORMATION FOR SEQ ID NO:5:

( i ) SEQUENCE CHARACTERISTICS:
        ( A ) LENGTH: 3
        ( B ) TYPE: Amino Acid
        ( C ) STRANDEDNESS: Unknown
        ( D ) TOPOLOGY: Unknown ( i i ) MOLECULE TYPE: PEPTIDE ( x i ) SEQUENCE DESCRIPTION: SEQ ID NO:5:

```
Arg  Gly  Asp
 1
```

( 2 ) INFORMATION FOR SEQ ID NO:6:

( i ) SEQUENCE CHARACTERISTICS:
        ( A ) LENGTH: 3
        ( B ) TYPE: Amino Acid
        ( C ) STRANDEDNESS: Unknown
        ( D ) TOPOLOGY: Unknown ( i i ) MOLECULE TYPE: PEPTIDE ( i x ) FEATURE:
        ( D ) OTHER INFORMATION: The Met at the first
        position is N-formyl-Met ( x i ) SEQUENCE DESCRIPTION: SEQ ID NO:6:

```
Met  Leu  Phe
 1
```

( 2 ) INFORMATION FOR SEQ ID NO:7:

( i ) SEQUENCE CHARACTERISTICS:
        ( A ) LENGTH: 13
        ( B ) TYPE: Amino Acid
        ( C ) STRANDEDNESS: Unknown
        ( D ) TOPOLOGY: Unknown -continued (ii) MOLECULE TYPE: PEPTIDE (ix) FEATURE:
    (D) OTHER INFORMATION: The serine in the
        1st position is acetylated (xi) SEQUENCE DESCRIPTION: SEQ ID NO:7:

Ser Tyr Ser Met Glu His Phe Arg Trp Gly Lys Pro Val
 1               5                   10

(2) INFORMATION FOR SEQ ID NO:8:

(i) SEQUENCE CHARACTERISTICS:
        (A) LENGTH: 22
        (B) TYPE: Amino Acid
        (C) STRANDEDNESS: Unknown
        (D) TOPOLOGY: linear (ii) MOLECULE TYPE: PEPTIDE (xi) SEQUENCE DESCRIPTION: SEQ ID NO:8:

Cys Tyr Ser Leu Arg Arg Ser Ser Ala Phe Gly Gly Arg
 1               5                   10

Ile Asp Arg Ile Gly Ala Gln Ser Ala
 15                  20